(12) United States Patent
Obika et al.

(10) Patent No.: US 9,127,280 B2
(45) Date of Patent: Sep. 8, 2015

(54) OLIGONUCLEOTIDE, AND THERAPEUTIC AGENT FOR DYSLIPIDEMIA CONTAINING OLIGONUCLEOTIDE AS ACTIVE INGREDIENT

(75) Inventors: Satoshi Obika, Osaka (JP); Takeshi Imanishi, Osaka (JP); Tsuyoshi Yamamoto, Osaka (JP); Keisuke Narukawa, Osaka (JP); Mariko Shiba, Osaka (JP); Tetsuji Yamaoka, Osaka (JP); Hidetaka Torigoe, Tokyo (JP); Atsushi Yamashita, Osaka (JP); Yoichi Tachibana, Osaka (JP); Sachiro Kakinoki, Osaka (JP); Kiyomi Sasaki, Tokyo (JP)

(73) Assignees: Osaka University, Osaka (JP); National Cerebral and Cardiovascular Center, Osaka (JP); Tokyo University of Science Education Foundation Administrative Organization, Tokyo (JP)

( * ) Notice: Subject to any disclaimer, the term of this patent is extended or adjusted under 35 U.S.C. 154(b) by 80 days.

(21) Appl. No.: 13/819,722

(22) PCT Filed: Aug. 31, 2011

(86) PCT No.: PCT/JP2011/069818
§ 371 (c)(1),
(2), (4) Date: Mar. 13, 2013

(87) PCT Pub. No.: WO2012/029870
PCT Pub. Date: Mar. 8, 2012

(65) Prior Publication Data
US 2013/0172402 A1  Jul. 4, 2013

(30) Foreign Application Priority Data
Aug. 31, 2010  (JP) ................................. 2010-195187

(51) Int. Cl.
| | |
|---|---|
| C07H 21/04 | (2006.01) |
| A61K 31/70 | (2006.01) |
| C12N 15/113 | (2010.01) |
| A61K 9/00 | (2006.01) |
| A61K 9/06 | (2006.01) |
| A61K 31/712 | (2006.01) |
| C12Q 1/68 | (2006.01) |

(52) U.S. Cl.
CPC .......... *C12N 15/1137* (2013.01); *A61K 9/0019* (2013.01); *A61K 9/0021* (2013.01); *A61K 9/06* (2013.01); *A61K 31/712* (2013.01); *C12N 2310/11* (2013.01); *C12N 2310/3231* (2013.01); *C12N 2310/351* (2013.01); *C12Y 304/21* (2013.01)

(58) Field of Classification Search
None
See application file for complete search history.

(56) References Cited

U.S. PATENT DOCUMENTS

| | | | | |
|---|---|---|---|---|
| 8,143,230 | B2 * | 3/2012 | Bhanot et al. | 514/44 A |
| 8,541,562 | B2 * | 9/2013 | Obika et al. | 536/23.1 |
| 2007/0167387 | A1 | 7/2007 | Imanishi et al. | |
| 2009/0306005 | A1 * | 12/2009 | Bhanot et al. | 514/44 |
| 2009/0318536 | A1 * | 12/2009 | Freier et al. | 514/44 A |
| 2012/0208991 | A1 | 8/2012 | Obika et al. | |

FOREIGN PATENT DOCUMENTS

| | | |
|---|---|---|
| WO | 2005021570 | 3/2005 |
| WO | 2008043753 | 4/2008 |
| WO | 2009127680 | 10/2009 |
| WO | 2010000665 | 1/2010 |
| WO | 2011052436 | 5/2011 |

OTHER PUBLICATIONS

Hanai et al., Annals New York Academy of Sciences vol. 1082:9-17, 2006.*
S. Obika et al., Tetrahedron Letters, 1997, vol. 38, p. 8735-8738.
S. Obika et al., Tetrahedron Letters, 1998, vol. 39, p. 5401-5404.
S. K. Singh et al., Chem. Commun., 1998, vol. 4, p. 455-456.
A. A. Koshkin et al., Tetrahedron, 1998, vol. 54, p. 3607-3630.
S. Obika et al., Bioorganic Medicinal Chemistry, 2001, vol. 9, p. 1001-1011.
S. M. A. Rahman et al., Angew. Chem. Int. Ed., 2007, vol. 46, p. 4306-4309.
S. M. A. Rahman et al., Nucleosides Nucleotides Nucleic Acids, 2007, vol. 2, 6, p. 1625-1628.
K. Miyashita et al., Chem. Commun., 2007, vol. 36, p. 3765-3767.

(Continued)

*Primary Examiner* — Sean McGarry
(74) *Attorney, Agent, or Firm* — Renner, Otto, Boisselle & Sklar, LLP

(57) ABSTRACT

An object of the present invention is to provide an oligonucleotide useful as a therapeutic agent for dyslipidemia that has excellent binding affinity to the PCSK9 gene as well as stability and safety. The oligonucleotide of the present invention contains a sugar-modified nucleoside, the sugar-modified nucleoside has a bridging structure between 4'-position and 2'-position, and the oligonucleotide can bind to the human PCSK9 gene. Also, the present invention provides a therapeutic agent for dyslipidemia containing the oligonucleotide as an active ingredient, and the therapeutic agent preferably contains a bioabsorbable material as a carrier. The bioabsorbable material is preferably atelocollagen or peptide gel.

10 Claims, 21 Drawing Sheets

(56) References Cited

OTHER PUBLICATIONS

Gupta, N. et al., A locked nucleic acid antisense oligonucleotide (LNA) silences PCSK9 and enhances LDLR expression in vitro and in vivo., PLoS One, May 2010, vol. 5 No. 5, e10682.

Koizumi, M., 2'-0,4'-C-Ethylene-Bridged Nucleic Acids (ENA™) as next-generation antisense and antigene agents., Biological & Pharmaceutical Bulletin, 2004, vol. 27 No. 4, p. 453-456.

Prakash, T.P. et al., Antisense oligonucleotides containing conformationally constrained 2',4'-(N-methoxy) aminomethylene and 2',4'-aminooxymethylene and 2'-0,4'-C• aminomethylene bridged nucleoside analogues show improved potency in animal models., J. Med. Chem., Feb. 2010, vol. 53 No. 4, p. 1636-1650.

Rahman, S.M.A. et al., Design, synthesis, and properties of 2', 4'-BNANC: a bridged nucleic acid analogue., J. Am. Chem. Soc., vol. 130 No. 14, 2008, p. 4886-4896.

Graham, M.J. et al., Antisense inhibition of proprotein convertase subtilisin/kexin type 9 reduces serum LDL in hyperlipidemic mice., J. Lipid Res., 2007, vol. 48 No. 4, p. 763-767.

Chan, J.H.P. et al., Antisense oligonucleotides: from design to therapeutic application., Clin. Exp. Pharmacal. Physiol., 2006, vol. 33 No. 5-6, p. 533-540.

Aartsma-Rus, A. et al., Guidelines for antisense oligonucleotide design and insight into splice-modulating mechanisms., Mol. Therapy, 2009, vol. 17 No. 3, p. 548-553.

Gray, D.M. et al., Antisense DNA parameters derived from next-nearest-neighbor analysis of experimental data., BMC Bioinformatics, May 2010, vol. 11 No. 252, p. 1-14.

Yahara, A. et al, Synthesis and properties of a novel 2', 4'-BNA bearing a urea bridged structure, Nucleic Acids Symposium Series, 2009, vol. 53, p. 11-12.

Nishida, M. et al, Synthesis and chemical properties of a novel 2', 4'-bridged nucleic acid analog with a seven-membered, Nucleic Acids Symposium Series, 2007, No. 51, p. 157-158.

Nishida, M. et al., Synthesis, RNA selective hybridization and high nuclease resistance of an oligonucleotide containing novel bridged nucleic acid with cyclic urea structure., Chemical Communications, Jun. 2010, vol. 46 No. 29, p. 5283-5285.

Frank-Kamenetsky, M. et al., Therapeutic RNAi targeting PCSK9 acutely lowers plasma cholesterol in rodents and LDL cholesterol in nonhuman primates., Proc. Natl. Acad. Sci. USA., 2008, vol. 105 No. 33, p. 11915-11920.

Rahman, S.M.A., et al, RNA interference with 2',4'-bridged nucleic acid analogues., Bioorganic & Medicinal Chemistry, Apr. 3, 2010, vol. 18 No. 10, p. 3474-3480.

PCT/JP2011/069818; PCT International Search Report dated Sep. 27, 2011.

Seidah; "PCSK9 as a therapeutic target of dyslipidemia"; Expert Opinion on Therapeutic Targets, vol. 13, No. 1, 2009, pp. 19-28.

Lindholm et al.; "PCSK9 LNA Antisense Oligonucleotides Induce Sustained Reduction of LDL Cholesterol in Nonhuman Primates"; Molecular Therapy, vol. 20, No. 2, 2012, pp. 376-381.

Yamamoto; "Cholesterol-lowering Action of BNA-based Antisense Oligonucleotides Targeting PCSK9 in Atherogenic Diet-induced Hypercholesterolemic Mice"; Molecular Therapy—Nucleic Acids, vol. 1, No. 1, 2012, p. e22.

* cited by examiner

FIG. 1

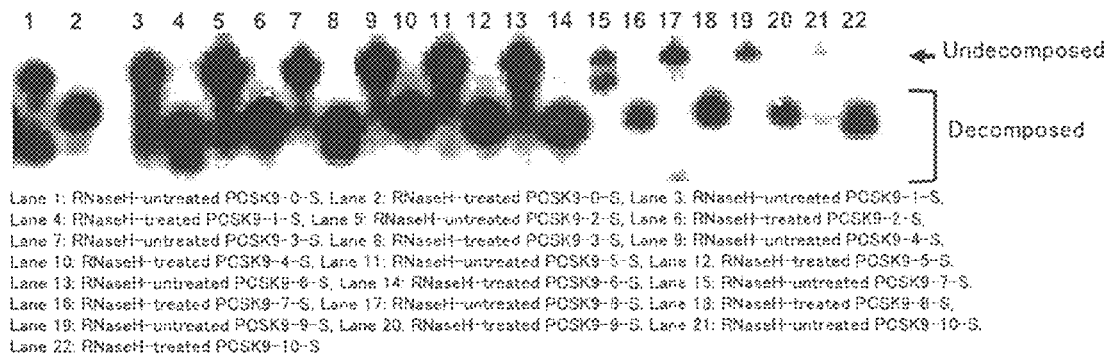

Lane 1: RNaseH-untreated PCSK9-0-S, Lane 2: RNaseH-treated PCSK9-0-S, Lane 3: RNaseH-untreated PCSK9-1-S,
Lane 4: RNaseH-treated PCSK9-1-S, Lane 5: RNaseH-untreated PCSK9-2-S, Lane 6: RNaseH-treated PCSK9-2-S,
Lane 7: RNaseH-untreated PCSK9-3-S, Lane 8: RNaseH-treated PCSK9-3-S, Lane 9: RNaseH-untreated PCSK9-4-S,
Lane 10: RNaseH-treated PCSK9-4-S, Lane 11: RNaseH-untreated PCSK9-5-S, Lane 12: RNaseH-treated PCSK9-5-S,
Lane 13: RNaseH-untreated PCSK9-6-S, Lane 14: RNaseH-treated PCSK9-6-S, Lane 15: RNaseH-untreated PCSK9-7-S,
Lane 16: RNaseH-treated PCSK9-7-S, Lane 17: RNaseH-untreated PCSK9-8-S, Lane 18: RNaseH-treated PCSK9-8-S,
Lane 19: RNaseH-untreated PCSK9-9-S, Lane 20: RNaseH-treated PCSK9-9-S, Lane 21: RNaseH-untreated PCSK9-10-S,
Lane 22: RNaseH-treated PCSK9-10-S

FIG. 2

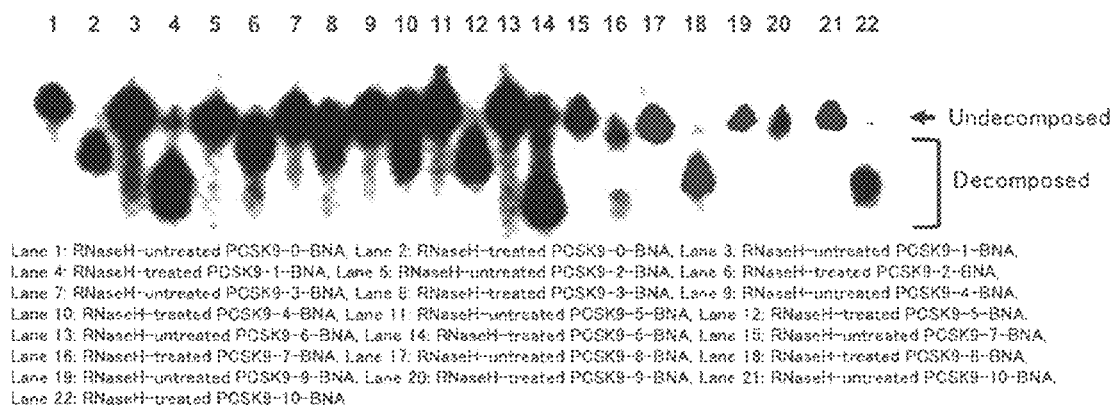

Lane 1: RNaseH-untreated PCSK9-0-BNA, Lane 2: RNaseH-treated PCSK9-0-BNA, Lane 3: RNaseH-untreated PCSK9-1-BNA,
Lane 4: RNaseH-treated PCSK9-1-BNA, Lane 5: RNaseH-untreated PCSK9-2-BNA, Lane 6: RNaseH-treated PCSK9-2-BNA,
Lane 7: RNaseH-untreated PCSK9-3-BNA, Lane 8: RNaseH-treated PCSK9-3-BNA, Lane 9: RNaseH-untreated PCSK9-4-BNA,
Lane 10: RNaseH-treated PCSK9-4-BNA, Lane 11: RNaseH-untreated PCSK9-5-BNA, Lane 12: RNaseH-treated PCSK9-5-BNA,
Lane 13: RNaseH-untreated PCSK9-6-BNA, Lane 14: RNaseH-treated PCSK9-6-BNA, Lane 15: RNaseH-untreated PCSK9-7-BNA,
Lane 16: RNaseH-treated PCSK9-7-BNA, Lane 17: RNaseH-untreated PCSK9-8-BNA, Lane 18: RNaseH-treated PCSK9-8-BNA,
Lane 19: RNaseH-untreated PCSK9-9-BNA, Lane 20: RNaseH-treated PCSK9-9-BNA, Lane 21: RNaseH-untreated PCSK9-10-BNA,
Lane 22: RNaseH-treated PCSK9-10-BNA

FIG. 3

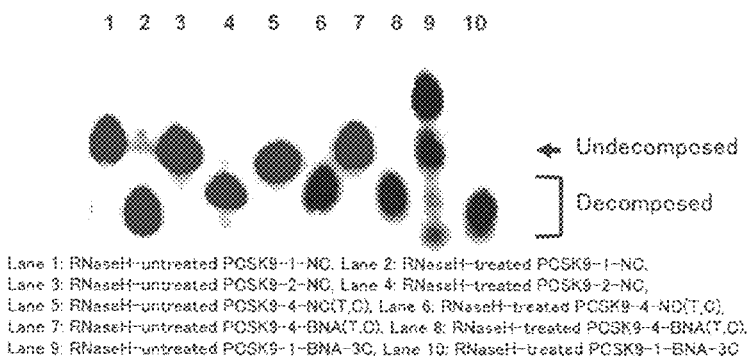

Lane 1: RNaseH-untreated PCSK9-1-NC, Lane 2: RNaseH-treated PCSK9-1-NC,
Lane 3: RNaseH-untreated PCSK9-2-NC, Lane 4: RNaseH-treated PCSK9-2-NC,
Lane 5: RNaseH-untreated PCSK9-4-NC(T,C), Lane 6: RNaseH-treated PCSK9-4-NC(T,C),
Lane 7: RNaseH-untreated PCSK9-4-BNA(T,C), Lane 8: RNaseH-treated PCSK9-4-BNA(T,C),
Lane 9: RNaseH-untreated PCSK9-1-BNA-3C, Lane 10: RNaseH-treated PCSK9-1-BNA-3C

FIG. 4

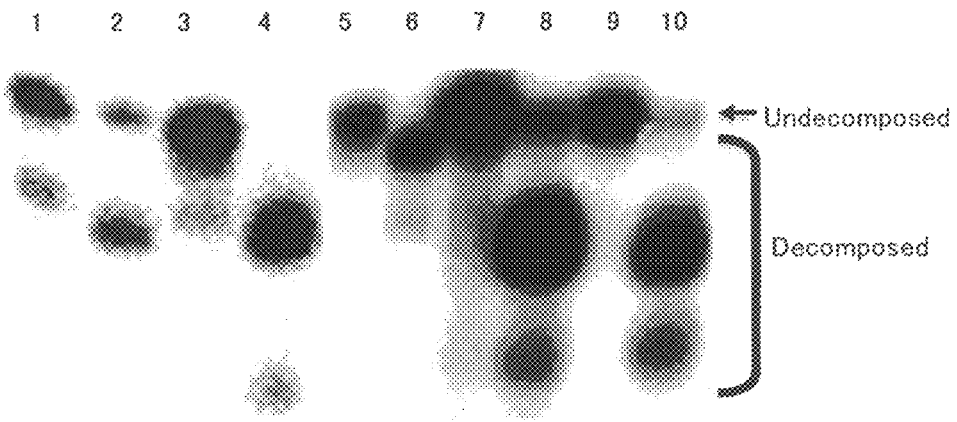

Lane 1: RNaseH-untreated PCSK9-5-NC(T,C), Lane 2: RNaseH-treated PCSK9-5-NC(T,C),
Lane 3: RNaseH-untreated PCSK9-6-NC(T,C), Lane 4: RNaseH-treated PCSK9-6-NC(T,C),
Lane 5: RNaseH-untreated PCSK9-7-NC(T,C), Lane 6: RNaseH-treated PCSK9-7-NC(T,C),
Lane 7: RNaseH-untreated PCSK9-8-NC(T,C), Lane 8: RNaseH-treated PCSK9-8-NC(T,C),
Lane 9: RNaseH-untreated PCSK9-10-NC(T,C), Lane 10: RNaseH-treated PCSK9-10-NC(T,C)

FIG. 5

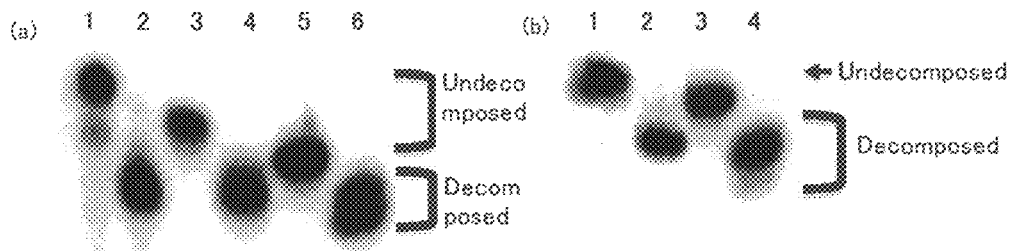

(a) Lane 1: RNaseH-untreated PCSK9-4-i-BNA, Lane 2: RNaseH-treated PCSK9-4-i-BNA,
Lane 3: RNaseH-untreated PCSK9-4-ii-BNA, Lane 4: RNaseH-treated PCSK9-4-ii-BNA,
Lane 5: RNaseH-untreated PCSK9-4-iii-BNA, Lane 6: RNaseH-treated PCSK9-4-iii-BNA,
(b) Lane 1: RNaseH-untreated PCSK9-4-ii-BNA-A, Lane 2: RNaseH-treated PCSK9-4-ii-BNA-A,
Lane 3: RNaseH-untreated PCSK9-4-iii-BNA-A, Lane 4: RNaseH-treated PCSK9-4-iii-BNA-A FIG. 18
(A)
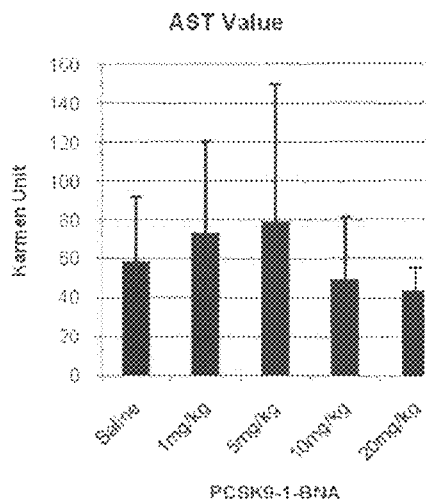
(B)
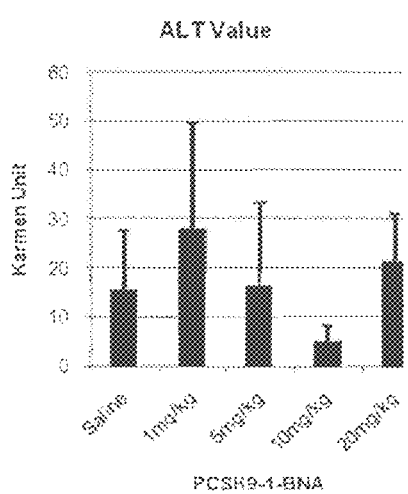
(C)
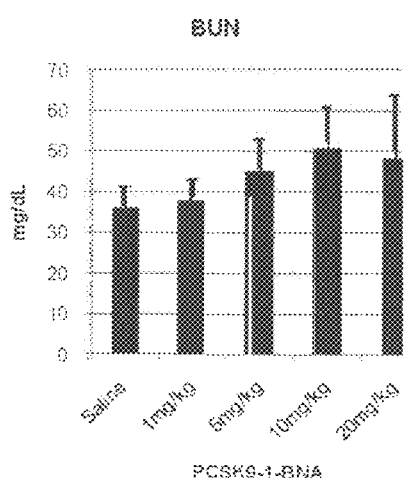

FIG. 21
(A)
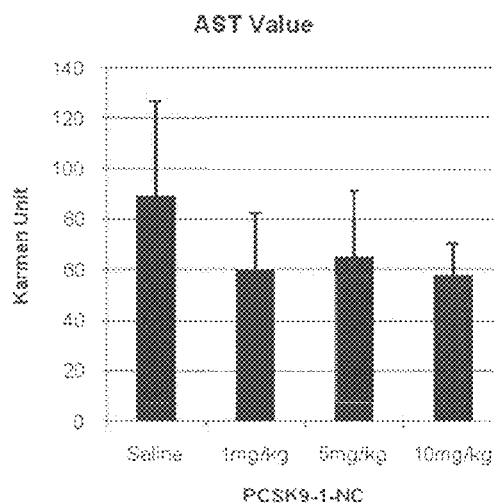
(B)
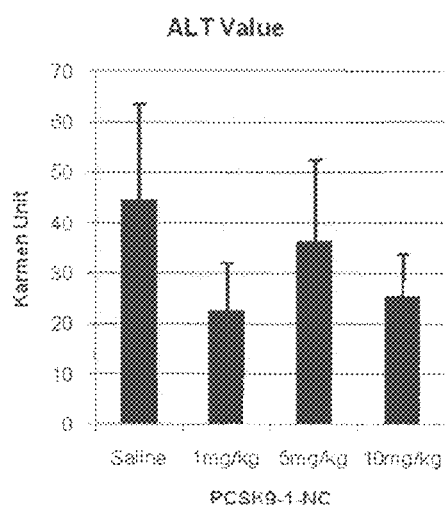
(C)
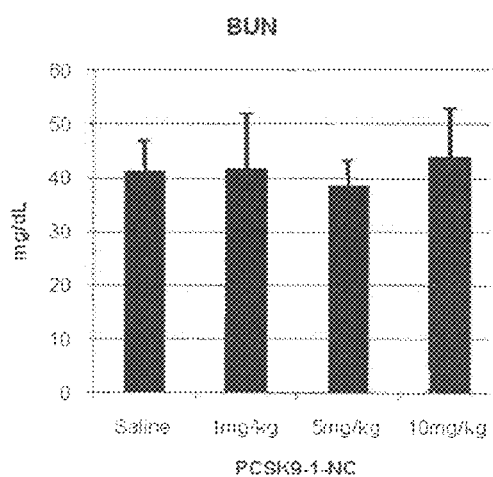

SEQUENCE LISTING

<160> NUMBER OF SEQ ID NOS: 39

<210> SEQ ID NO 1
<211> LENGTH: 2079
<212> TYPE: DNA
<213> ORGANISM: Homo sapiens
<220> FEATURE:
<221> NAME/KEY: CDS
<222> LOCATION: (1)..(2079)

<400> SEQUENCE: 1

```
atg ggc acc gtc agc tcc agg cgg tcc tgg tgg ccg ctg cca ctg ctg     48
Met Gly Thr Val Ser Ser Arg Arg Ser Trp Trp Pro Leu Pro Leu Leu
1               5                   10                  15 ctg ctg ctg ctg ctg ctc ctg ggt ccc gcg ggc gcc cgt gcg cag gag     96
Leu Leu Leu Leu Leu Leu Leu Gly Pro Ala Gly Ala Arg Ala Gln Glu
                20                  25                  30 gac gag gac ggc gac tac gag gag ctg gtg cta gcc ttg cgt tcc gag    144
Asp Glu Asp Gly Asp Tyr Glu Glu Leu Val Leu Ala Leu Arg Ser Glu
            35                  40                  45 gag gac ggc ctg gcc gaa gca ccc gag cac gga acc aca gcc acc ttc    192
Glu Asp Gly Leu Ala Glu Ala Pro Glu His Gly Thr Thr Ala Thr Phe
        50                  55                  60 cac cgc tgc gcc aag gat ccg tgg agg ttg cct ggc acc tac gtg gtg    240
His Arg Cys Ala Lys Asp Pro Trp Arg Leu Pro Gly Thr Tyr Val Val
65                  70                  75                  80 gtg ctg aag gag gag acc cac ctc tcg cag tca gag cgc act gcc cgc    288
Val Leu Lys Glu Glu Thr His Leu Ser Gln Ser Glu Arg Thr Ala Arg
                85                  90                  95 cgc ctg cag gcc cag gct gcc cgc cgg gga tac ctc acc aag atc ctg    336
Arg Leu Gln Ala Gln Ala Ala Arg Arg Gly Tyr Leu Thr Lys Ile Leu
            100                 105                 110 cat gtc ttc cat ggc ctt ctt cct ggc ttc ctg gtg aag atg agt ggc    384
His Val Phe His Gly Leu Leu Pro Gly Phe Leu Val Lys Met Ser Gly
        115                 120                 125 gac ctg ctg gag ctg gcc ttg aag ttg ccc cat gtc gac tac atc gag    432
Asp Leu Leu Glu Leu Ala Leu Lys Leu Pro His Val Asp Tyr Ile Glu
    130                 135                 140 gag gac tcc tct gtc ttt gcc cag agc atc ccg tgg aac ctg gag cgg    480
Glu Asp Ser Ser Val Phe Ala Gln Ser Ile Pro Trp Asn Leu Glu Arg
145                 150                 155                 160 att acc cct cca cgg tac cgg gcg gat gaa tac cag ccc ccc gac gga    528
Ile Thr Pro Pro Arg Tyr Arg Ala Asp Glu Tyr Gln Pro Pro Asp Gly
                165                 170                 175 ggc agc ctg gtg gag gta tat ctc cta gac acc agc ata cag agt gac    576
Gly Ser Leu Val Glu Val Tyr Leu Leu Asp Thr Ser Ile Gln Ser Asp
            180                 185                 190
```

```
cac cgg gaa atc gag ggc agg gtc atg gtc acc gac ttc gag aat gtg        624
His Arg Glu Ile Glu Gly Arg Val Met Val Thr Asp Phe Glu Asn Val
        195                 200                 205 ccc gag gag gac ggg acc cgc ttc cac aga cag gcc agc aag tgt gac        672
Pro Glu Glu Asp Gly Thr Arg Phe His Arg Gln Ala Ser Lys Cys Asp
    210                 215                 220 agt cat ggc acc cac ctg gca ggg gtg gtc agc ggc cgg gat gcc ggc        720
Ser His Gly Thr His Leu Ala Gly Val Val Ser Gly Arg Asp Ala Gly
225                 230                 235                 240 gtg gcc aag ggt gcc agc atg cgc agc ctg cgc gtg ctc aac tgc caa        768
Val Ala Lys Gly Ala Ser Met Arg Ser Leu Arg Val Leu Asn Cys Gln
                245                 250                 255 ggg aag ggc acg gtt agc ggc acc ctc ata ggc ctg gag ttt att cgg        816
Gly Lys Gly Thr Val Ser Gly Thr Leu Ile Gly Leu Glu Phe Ile Arg
            260                 265                 270 aaa agc cag ctg gtc cag cct gtg ggg cca ctg gtg gtg ctg ctg ccc        864
Lys Ser Gln Leu Val Gln Pro Val Gly Pro Leu Val Val Leu Leu Pro
        275                 280                 285 ctg gcg ggt ggg tac agc cgc gtc ctc aac gcc gcc tgc cag cgc ctg        912
Leu Ala Gly Gly Tyr Ser Arg Val Leu Asn Ala Ala Cys Gln Arg Leu
    290                 295                 300 gcg agg gct ggg gtc gtg ctg gtc acc gct gcc ggc aac ttc cgg gac        960
Ala Arg Ala Gly Val Val Leu Val Thr Ala Ala Gly Asn Phe Arg Asp
305                 310                 315                 320 gat gcc tgc ctc tac tcc cca gcc tca gct ccc gag gtc atc aca gtt       1008
Asp Ala Cys Leu Tyr Ser Pro Ala Ser Ala Pro Glu Val Ile Thr Val
                325                 330                 335 ggg gcc acc aat gcc caa gac cag ccg gtg acc ctg ggg act ttg ggg       1056
Gly Ala Thr Asn Ala Gln Asp Gln Pro Val Thr Leu Gly Thr Leu Gly
            340                 345                 350 acc aac ttt ggc cgc tgt gtg gac ctc ttt gcc cca ggg gag gac atc       1104
Thr Asn Phe Gly Arg Cys Val Asp Leu Phe Ala Pro Gly Glu Asp Ile
        355                 360                 365 att ggt gcc tcc agc gac tgc agc acc tgc ttt gtg tca cag agt ggg       1152
Ile Gly Ala Ser Ser Asp Cys Ser Thr Cys Phe Val Ser Gln Ser Gly
    370                 375                 380 aca tca cag gct gct gcc cac gtg gct ggc att gca gcc atg atg ctg       1200
Thr Ser Gln Ala Ala Ala His Val Ala Gly Ile Ala Ala Met Met Leu
385                 390                 395                 400 tct gcc gag ccg gag ctc acc ctg gcc gag ttg agg cag aga ctg atc       1248
Ser Ala Glu Pro Glu Leu Thr Leu Ala Glu Leu Arg Gln Arg Leu Ile
                405                 410                 415 cac ttc tct gcc aaa gat gtc atc aat gag gcc tgg ttc cct gag gac       1296
His Phe Ser Ala Lys Asp Val Ile Asn Glu Ala Trp Phe Pro Glu Asp
            420                 425                 430 cag cgg gta ctg acc ccc aac ctg gtg gcc gcc ctg ccc ccc agc acc       1344
Gln Arg Val Leu Thr Pro Asn Leu Val Ala Ala Leu Pro Pro Ser Thr
        435                 440                 445 cat ggg gca ggt tgg cag ctg ttt tgc agg act gta tgg tca gca cac       1392
His Gly Ala Gly Trp Gln Leu Phe Cys Arg Thr Val Trp Ser Ala His
    450                 455                 460 tcg ggg cct aca cgg atg gcc aca gcc gtc gcc cgc tgc gcc cca gat       1440
Ser Gly Pro Thr Arg Met Ala Thr Ala Val Ala Arg Cys Ala Pro Asp
465                 470                 475                 480 gag gag ctg ctg agc tgc tcc agt ttc tcc agg agt ggg aag cgg cgg       1488
Glu Glu Leu Leu Ser Cys Ser Ser Phe Ser Arg Ser Gly Lys Arg Arg
                485                 490                 495 ggc gag cgc atg gag gcc caa ggg ggc aag ctg gtc tgc cgg gcc cac       1536
Gly Glu Arg Met Glu Ala Gln Gly Gly Lys Leu Val Cys Arg Ala His
```

```
                          500                 505                 510
aac gct ttt ggg ggt gag ggt gtc tac gcc att gcc agg tgc tgc ctg      1584
Asn Ala Phe Gly Gly Glu Gly Val Tyr Ala Ile Ala Arg Cys Cys Leu
        515                 520                 525 cta ccc cag gcc aac tgc agc gtc cac aca gct cca cca gct gag gcc      1632
Leu Pro Gln Ala Asn Cys Ser Val His Thr Ala Pro Pro Ala Glu Ala
530                 535                 540 agc atg ggg acc cgt gtc cac tgc cac caa cag ggc cac gtc ctc aca      1680
Ser Met Gly Thr Arg Val His Cys His Gln Gln Gly His Val Leu Thr
545                 550                 555                 560 ggc tgc agc tcc cac tgg gag gtg gag gac ctt ggc acc cac aag ccg      1728
Gly Cys Ser Ser His Trp Glu Val Glu Asp Leu Gly Thr His Lys Pro
            565                 570                 575 cct gtg ctg agg cca cga ggt cag ccc aac cag tgc gtg ggc cac agg      1776
Pro Val Leu Arg Pro Arg Gly Gln Pro Asn Gln Cys Val Gly His Arg
        580                 585                 590 gag gcc agc atc cac gct tcc tgc tgc cat gcc cca ggt ctg gaa tgc      1824
Glu Ala Ser Ile His Ala Ser Cys Cys His Ala Pro Gly Leu Glu Cys
    595                 600                 605 aaa gtc aag gag cat gga atc ccg gcc cct cag gag cag gtg acc gtg      1872
Lys Val Lys Glu His Gly Ile Pro Ala Pro Gln Glu Gln Val Thr Val
610                 615                 620 gcc tgc gag gag ggc tgg acc ctg act ggc tgc agt gcc ctc cct ggg      1920
Ala Cys Glu Glu Gly Trp Thr Leu Thr Gly Cys Ser Ala Leu Pro Gly
625                 630                 635                 640 acc tcc cac gtc ctg ggg gcc tac gcc gta gac aac acg tgt gta gtc      1968
Thr Ser His Val Leu Gly Ala Tyr Ala Val Asp Asn Thr Cys Val Val
            645                 650                 655 agg agc cgg gac gtc agc act aca ggc agc acc agc gaa ggg gcc gtg      2016
Arg Ser Arg Asp Val Ser Thr Thr Gly Ser Thr Ser Glu Gly Ala Val
        660                 665                 670 aca gcc gtt gcc atc tgc tgc cgg agc cgg cac ctg gcg cag gcc tcc      2064
Thr Ala Val Ala Ile Cys Cys Arg Ser Arg His Leu Ala Gln Ala Ser
    675                 680                 685 cag gag ctc cag tga                                                   2079
Gln Glu Leu Gln
    690

<210> SEQ ID NO 2
<211> LENGTH: 692
<212> TYPE: PRT
<213> ORGANISM: Homo sapiens

<400> SEQUENCE: 2

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110
```

```
His Val Phe His Gly Leu Leu Pro Gly Phe Leu Val Lys Met Ser Gly
            115                 120                 125
Asp Leu Leu Glu Leu Ala Leu Lys Leu Pro His Val Asp Tyr Ile Glu
130                 135                 140
Glu Asp Ser Ser Val Phe Ala Gln Ser Ile Pro Trp Asn Leu Glu Arg
145                 150                 155                 160
Ile Thr Pro Pro Arg Tyr Arg Ala Asp Glu Tyr Gln Pro Pro Asp Gly
                165                 170                 175
Gly Ser Leu Val Glu Val Tyr Leu Leu Asp Thr Ser Ile Gln Ser Asp
            180                 185                 190
His Arg Glu Ile Glu Gly Arg Val Met Val Thr Asp Phe Glu Asn Val
        195                 200                 205
Pro Glu Glu Asp Gly Thr Arg Phe His Arg Gln Ala Ser Lys Cys Asp
    210                 215                 220
Ser His Gly Thr His Leu Ala Gly Val Val Ser Gly Arg Asp Ala Gly
225                 230                 235                 240
Val Ala Lys Gly Ala Ser Met Arg Ser Leu Arg Val Leu Asn Cys Gln
                245                 250                 255
Gly Lys Gly Thr Val Ser Gly Thr Leu Ile Gly Leu Glu Phe Ile Arg
            260                 265                 270
Lys Ser Gln Leu Val Gln Pro Val Gly Pro Leu Val Val Leu Leu Pro
275                 280                 285
Leu Ala Gly Gly Tyr Ser Arg Val Leu Asn Ala Ala Cys Gln Arg Leu
    290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
            340                 345                 350
Thr Asn Phe Gly Arg Cys Val Asp Leu Phe Ala Pro Gly Glu Asp Ile
        355                 360                 365
Ile Gly Ala Ser Ser Asp Cys Ser Thr Cys Phe Val Ser Gln Ser Gly
370                 375                 380
Thr Ser Gln Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
            420                 425                 430
Gln Arg Val Leu Thr Pro Asn Leu Val Ala Ala Leu Pro Pro Ser Thr
        435                 440                 445
His Gly Ala Gly Trp Gln Leu Phe Cys Arg Thr Val Trp Ser Ala His
    450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
            500                 505                 510
Asn Ala Phe Gly Gly Glu Gly Val Tyr Ala Ile Ala Arg Cys Cys Leu
        515                 520                 525
Leu Pro Gln Ala Asn Cys Ser Val His Thr Ala Pro Pro Ala Glu Ala
```

```
                     530                 535                 540
Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 3
<211> LENGTH: 20
<212> TYPE: DNA
<213> ORGANISM: Homo sapiens

<400> SEQUENCE: 3
cggcaccctc ataggcctgg                                                 20

<210> SEQ ID NO 4
<211> LENGTH: 13
<212> TYPE: DNA
<213> ORGANISM: Homo sapiens

<400> SEQUENCE: 4
gcaccctcat agg                                                        13

<210> SEQ ID NO 5
<211> LENGTH: 20
<212> TYPE: DNA
<213> ORGANISM: Homo sapiens

<400> SEQUENCE: 5
gtggtcagcg gccgggatgc                                                 20

<210> SEQ ID NO 6
<211> LENGTH: 13
<212> TYPE: DNA
<213> ORGANISM: Homo sapiens

<400> SEQUENCE: 6
ggtcagcggc cgg                                                        13

<210> SEQ ID NO 7
<211> LENGTH: 20
<212> TYPE: DNA
<213> ORGANISM: Homo sapiens

<400> SEQUENCE: 7
```

```
gcctgcctct actccccagc                                               20

<210> SEQ ID NO 8
<211> LENGTH: 13
<212> TYPE: DNA
<213> ORGANISM: Homo sapiens

<400> SEQUENCE: 8
gcctgcctct act                                                      13

<210> SEQ ID NO 9
<211> LENGTH: 20
<212> TYPE: DNA
<213> ORGANISM: Homo sapiens

<400> SEQUENCE: 9
caggctgctg cccacgtggc                                               20

<210> SEQ ID NO 10
<211> LENGTH: 16
<212> TYPE: DNA
<213> ORGANISM: Homo sapiens

<400> SEQUENCE: 10
caggctgctg cccacg                                                   16

<210> SEQ ID NO 11
<211> LENGTH: 14
<212> TYPE: DNA
<213> ORGANISM: Homo sapiens

<400> SEQUENCE: 11
ggctgctgcc cacg                                                     14

<210> SEQ ID NO 12
<211> LENGTH: 13
<212> TYPE: DNA
<213> ORGANISM: Homo sapiens

<400> SEQUENCE: 12
ctgctgccca cgt                                                      13

<210> SEQ ID NO 13
<211> LENGTH: 20
<212> TYPE: DNA
<213> ORGANISM: Homo sapiens

<400> SEQUENCE: 13
ggcctggttc cctgaggacc                                               20

<210> SEQ ID NO 14
<211> LENGTH: 20
<212> TYPE: DNA
<213> ORGANISM: Homo sapiens

<400> SEQUENCE: 14
ctgaccccca acctggtggc                                               20

<210> SEQ ID NO 15
<211> LENGTH: 20
<212> TYPE: DNA
<213> ORGANISM: Homo sapiens
```

```
<400> SEQUENCE: 15
gagctgctga gctgctccag                                          20

<210> SEQ ID NO 16
<211> LENGTH: 20
<212> TYPE: DNA
<213> ORGANISM: Homo sapiens

<400> SEQUENCE: 16
tttgggggtg agggtgtcta                                          20

<210> SEQ ID NO 17
<211> LENGTH: 20
<212> TYPE: DNA
<213> ORGANISM: Homo sapiens

<400> SEQUENCE: 17
tcctgctgcc atgccccagg                                          20

<210> SEQ ID NO 18
<211> LENGTH: 20
<212> TYPE: DNA
<213> ORGANISM: Homo sapiens

<400> SEQUENCE: 18
catctgctgc cggagccggc                                          20

<210> SEQ ID NO 19
<211> LENGTH: 20
<212> TYPE: DNA
<213> ORGANISM: Artificial
<220> FEATURE:
<223> OTHER INFORMATION: PCSK9 Fw primer 0

<400> SEQUENCE: 19
tcagttctgc acacctccag                                          20

<210> SEQ ID NO 20
<211> LENGTH: 20
<212> TYPE: DNA
<213> ORGANISM: Artificial
<220> FEATURE:
<223> OTHER INFORMATION: PCSK9 Rv primer 0

<400> SEQUENCE: 20
gggtaaggtg cggtaagtcc                                          20

<210> SEQ ID NO 21
<211> LENGTH: 20
<212> TYPE: DNA
<213> ORGANISM: Artificial
<220> FEATURE:
<223> OTHER INFORMATION: PCSK9 Fw primer 1

<400> SEQUENCE: 21
cacgcttcca cagacaggcg                                          20

<210> SEQ ID NO 22
<211> LENGTH: 20
<212> TYPE: DNA
<213> ORGANISM: Artificial
<220> FEATURE:
<223> OTHER INFORMATION: PCSK9 Rv primer 1

<400> SEQUENCE: 22
```
cgttgaggat gcggctatac                                            20

<210> SEQ ID NO 23
<211> LENGTH: 20
<212> TYPE: DNA
<213> ORGANISM: Artificial
<220> FEATURE:
<223> OTHER INFORMATION: PCSK9 Fw primer 2

<400> SEQUENCE: 23
gccggcacct ggcgaggact                                            20

<210> SEQ ID NO 24
<211> LENGTH: 20
<212> TYPE: DNA
<213> ORGANISM: Artificial
<220> FEATURE:
<223> OTHER INFORMATION: PCSK9 Rv primer 2

<400> SEQUENCE: 24
ccactctgtg acatgaagca                                            20

<210> SEQ ID NO 25
<211> LENGTH: 20
<212> TYPE: DNA
<213> ORGANISM: Artificial
<220> FEATURE:
<223> OTHER INFORMATION: PCSK9 Fw primer 3

<400> SEQUENCE: 25
gtgactgcag cacatgcttc                                            20

<210> SEQ ID NO 26
<211> LENGTH: 20
<212> TYPE: DNA
<213> ORGANISM: Artificial
<220> FEATURE:
<223> OTHER INFORMATION: PCSK9 Rv primer 3

<400> SEQUENCE: 26
cgtcctacag agcagctgcc                                            20

<210> SEQ ID NO 27
<211> LENGTH: 20
<212> TYPE: DNA
<213> ORGANISM: Artificial
<220> FEATURE:
<223> OTHER INFORMATION: PCSK9 Fw primer 4

<400> SEQUENCE: 27
gctctgtagg acggtgtggt                                            20

<210> SEQ ID NO 28
<211> LENGTH: 20
<212> TYPE: DNA
<213> ORGANISM: Artificial
<220> FEATURE:
<223> OTHER INFORMATION: PCSK9 Rv primer 4

<400> SEQUENCE: 28
ggtgttgtgg atgctgcagt                                            20

<210> SEQ ID NO 29
<211> LENGTH: 20
<212> TYPE: DNA

```
<213> ORGANISM: Artificial
<220> FEATURE:
<223> OTHER INFORMATION: PCSK9 Fw primer 5

<400> SEQUENCE: 29
ccagaaggac catgttctca                                              20

<210> SEQ ID NO 30
<211> LENGTH: 20
<212> TYPE: DNA
<213> ORGANISM: Artificial
<220> FEATURE:
<223> OTHER INFORMATION: PCSK9 Rv primer 5

<400> SEQUENCE: 30
gcacattgca tccagtcagg                                              20

<210> SEQ ID NO 31
<211> LENGTH: 20
<212> TYPE: DNA
<213> ORGANISM: Artificial
<220> FEATURE:
<223> OTHER INFORMATION: PCSK9 Fw primer 6

<400> SEQUENCE: 31
ggatctcagg tccttcagag                                              20

<210> SEQ ID NO 32
<211> LENGTH: 20
<212> TYPE: DNA
<213> ORGANISM: Artificial
<220> FEATURE:
<223> OTHER INFORMATION: PCSK9 Rv primer 6

<400> SEQUENCE: 32
gcctgaggct gtcactgaac                                              20

<210> SEQ ID NO 33
<211> LENGTH: 20
<212> TYPE: DNA
<213> ORGANISM: Artificial
<220> FEATURE:
<223> OTHER INFORMATION: GAPDH Fw primer

<400> SEQUENCE: 33
gtgtgaacgg atttggccgt                                              20

<210> SEQ ID NO 34
<211> LENGTH: 20
<212> TYPE: DNA
<213> ORGANISM: Artificial
<220> FEATURE:
<223> OTHER INFORMATION: GAPDH Rv primer

<400> SEQUENCE: 34
gacaagcttc ccattctcgg                                              20

<210> SEQ ID NO 35
<211> LENGTH: 20
<212> TYPE: DNA
<213> ORGANISM: Artificial
<220> FEATURE:
<223> OTHER INFORMATION: PCSK9 Fw primer 7

<400> SEQUENCE: 35
gctcaactgt caagggaagg                                              20
```

```
<210> SEQ ID NO 36
<211> LENGTH: 16
<212> TYPE: PRT
<213> ORGANISM: Artificial
<220> FEATURE:
<223> OTHER INFORMATION: 2-microglobulin mimic peptide 1

<400> SEQUENCE: 36

Arg Val Asp Ile Arg Val Asp Ile Arg Val Asp Ile Arg Val Asp Ile
1               5                   10                  15

<210> SEQ ID NO 37
<211> LENGTH: 16
<212> TYPE: PRT
<213> ORGANISM: Artificial
<220> FEATURE:
<223> OTHER INFORMATION: 2-microglobulin mimic peptide 2

<400> SEQUENCE: 37

Arg Val Glu Ile Arg Val Glu Ile Arg Val Glu Ile Arg Val Glu Ile
1               5                   10                  15

<210> SEQ ID NO 38
<211> LENGTH: 16
<212> TYPE: PRT
<213> ORGANISM: Artificial
<220> FEATURE:
<223> OTHER INFORMATION: 2-microglobulin mimic peptide 3

<400> SEQUENCE: 38

Arg Val Lys Val Glu Ile Asp Ile Arg Val Lys Val Glu Ile Asp Ile
1               5                   10                  15

<210> SEQ ID NO 39
<211> LENGTH: 16
<212> TYPE: PRT
<213> ORGANISM: Artificial
<220> FEATURE:
<223> OTHER INFORMATION: 2-microglobulin mimic peptide 4

<400> SEQUENCE: 39

Arg Val Glu Ile Lys Val Asp Ile Arg Val Glu Ile Lys Val Asp Ile
1               5                   10                  15
```

OLIGONUCLEOTIDE, AND THERAPEUTIC AGENT FOR DYSLIPIDEMIA CONTAINING OLIGONUCLEOTIDE AS ACTIVE INGREDIENT

TECHNICAL FIELD

The present invention relates to an oligonucleotide and a therapeutic agent for dyslipidemia containing the oligonucleotide as an active ingredient.

BACKGROUND ART

Familial hypercholesterolemia resulting from mutations in the LDL receptor gene is a disease that appears 1 out of 500 people (250000 people domestically), and is the most common disease among the hereditary metabolic disorders. Patients' serum total cholesterol levels show 230 to 500 mg/dL (healthy person: 200 mg/dl or less), and symptoms such as xanthoma of the skin and tendon and coronary artery disease resulting from juvenile arteriosclerosis are observed. The average life expectancy of the patients is 54 years for male and 69 years for female, being much shorter than the average life expectancy of the entire population. A typical therapeutic method may be LDL apheresis treatment, but this therapeutic method is problematic in that the method imposes a large burden on the patient. An example of drug therapy may be administration of statins, but there is a problem in that statins do not show sufficient effects on familial hypercholesterolemia.

Meanwhile, hyperlipidemia is a lifestyle-induced disease that causes cardiac infarction and apoplexy, which are causes of death next to cancer.

In therapeutic development for such hypercholesterolemia, a strategy targeting PCSK9, which regulates the metabolism of an LDL (low-density lipoprotein) receptor, has recently been attracting attention (Non Patent Literature 1). It aims at lowering the blood LDL concentration by suppressing the expression of the PCSK9 gene, which decomposes the LDL receptor, and thus increasing the level of LDL receptor expression and facilitating the cellular uptake and metabolism of LDL. Therapeutic experiments using an antisense method that is one technique involving nucleic acid medicines are also in progress.

Most of the conventional nucleic acid medicines that are effective in the in vitro cellular system are, however, not effective in vivo. Possible causes may be that conventional nucleic acid medicines are immediately decomposed when introduced into the body and that the affinity and specificity of conventional nucleic acid medicines to the target gene are poor, and therefore an antisense technique has been attracting attention as a technique to suppress the PCSK9 gene expression.

The 2'-MOE (2'-O-methoxyethyl)-modified oligonucleotide described in Non Patent Literature 2 has excellent stability in the living body but has a poor binding affinity to the target RNA, and is thus problematic in that a very high dose is required to demonstrate a pharmaceutical effect. The oligonucleotide containing a locked nucleic acid (LNA) described in Non Patent Literature 1 has a superior binding affinity to the target RNA, and an effect of suppressing the mRNA of PCSK9 in vivo also is shown, but there is still room for improvement in stability, safety, and the like in the living body.

CITATION LIST

| | |
|---|---|
| [Non Patent Literature 1] | N. Gupta et al., PLoS ONE, 2010, Vol. 5, e10682 |
| [Non Patent Literature 2] | M. J. Graham et al., J. Lipid. Res., 2007, Vol. 48, p. 763 |
| [Non Patent Literature 3] | S. Obika et al., Tetrahedron Lett., 1997, Vo. 38, p. 8735-8738 |
| [Non Patent Literature 4] | S. Obika et al., Tetrahedron Lett., 1998, Vol39, p. 5401-5404 |
| [Non Patent Literature 5] | S. K. Singh et al., Chem. Commun., 1998, Vol. 4, p. 455-456 |
| [Non Patent Literature 6] | A. A. Koshkin et al., Tetrahedron, 1998, Vol. 54, p. 3607-3630 |
| [Non Patent Literature 7] | S. Obika et al., Bioorg. Med. Chem., 2001, Vol. 9, p. 1001-1011 |
| [Non Patent Literature 8] | S. M. A. Rahman et al., Angew. Chem. Int. Ed., 2007, Vol. 46, p. 4306-4309 |
| [Non Patent Literature 9] | S. M. A. Rahman et al., Nucleosides Nucleotides Nucleic Acids, 2007, Vol. 26, p. 1625-1628 |
| [Non Patent Literature 10] | K. Miyashita et al., Chem. Commun., 2007, Vol. 36, p. 3765-3767 |
| [Non Patent Literature 11] | S. M. A. Rahman et al., J. Am. Chem. Soc., 2008, Vol. 130, p. 4886-4896 |

SUMMARY OF INVENTION

Technical Problem

An object of the present invention is to provide an oligonucleotide useful as a therapeutic agent for dyslipidemia that has excellent binding affinity to the PCSK9 gene as well as stability and safety.

Solution to Problem

As a result of having conducted diligent research to solve the foregoing problems, the inventors found that allowing a bridged artificial nucleic acid to be contained in an oligonucleotide that can bind to a specific target sequence of the PCSK9 gene makes it possible to provide an oligonucleotide useful as a therapeutic agent for dyslipidemia that has excellent binding affinity to the PCSK9 gene as well as stability and safety, and then the inventors accomplished the present invention. Moreover, the inventors found that formulating a sustained-release preparation that contains a bioabsorbable material as a carrier makes it possible to use the pharmaceutical agent in a low dose, and thus the inventors accomplished the present invention.

The present invention provides an oligonucleotide containing a sugar-modified nucleoside, the sugar-modified nucleoside has a bridging structure between 4'-position and 2'-position, and the oligonucleotide can bind to the human PCSK9 gene.

In one embodiment, the human PCSK9 gene is a DNA or RNA composed of a base sequence containing any of the following base sequences: base sequence of SEQ ID NO. 3; base sequence of SEQ ID NO. 4; base sequence of SEQ ID NO. 5; base sequence of SEQ ID NO. 6; base sequence of SEQ ID NO. 7; base sequence of SEQ ID NO. 8; base sequence of SEQ ID NO. 9; base sequence of SEQ ID NO. 10; base sequence of SEQ ID NO. 11; base sequence of SEQ ID NO. 12; base sequence of SEQ ID NO. 13; base sequence of SEQ ID NO. 14; base sequence of SEQ ID NO. 15; base sequence of SEQ ID NO. 16; base sequence of SEQ ID NO. 17; base sequence of SEQ ID NO. 18; or base sequences complementary to these.

In one embodiment, the bridging structure is represented by —CH$_2$—O—, —(CH$_2$)$_2$—O—, —CH$_2$—NR$^1$—O—, or —(CH$_2$)$_2$—NR$^1$—O—, wherein R$^1$ is a hydrogen atom;

a C$_{1-7}$ alkyl group that may form a branch or ring;

a C$_{2-7}$ alkenyl group that may form a branch or ring;

a C$_{3-12}$ aryl group that may have any one or more substituents selected from an α group consisting of a hydroxyl group, C$_{1-6}$ linear alkyl group, C$_{1-6}$ linear alkoxy group, mercapto group, C$_{1-6}$ linear alkylthio group, amino group, C$_{1-6}$ linear alkylamino group, and halogen atom, and that may contain a hetero atom; or an aralkyl group having a C$_{3-12}$ aryl portion that may have any one or more substituents selected from the α group and that may contain a hetero atom.

In one embodiment, the bridging structure is represented by —CO—NR$^1$—, —CH$_2$—CO—NR$^1$—, —(CH$_2$)$_2$—CO—NR$^1$—, —CO—NR$^1$—X—, or —CH$_2$—CO—NR$^1$—X—, wherein R$^1$ is a hydrogen atom;

a C$_{1-7}$ alkyl group that may form a branch or ring;

a C$_{2-7}$ alkenyl group that may form a branch or ring;

a C$_{3-12}$ aryl group that may have any one or more substituents selected from an α group consisting of a hydroxyl group, C$_{1-6}$ linear alkyl group, C$_{1-6}$ linear alkoxy group, mercapto group, C$_{1-6}$ linear alkylthio group, amino group, C$_{1-6}$ linear alkylamino group, and halogen atom, and that may contain a hetero atom; or an aralkyl group having a C$_{3-12}$ aryl portion that may have any one or more substituents selected from the α group and that may have a hetero atom; and X is an oxygen atom, sulfur atom, amino group, or methylene group.

In one embodiment, the oligonucleotide has a base sequence length of 10 to 25 bases.

In one embodiment, at least one selected from the group consisting of an intercalator, reporter molecule, polyamine, polyamide, polyethylene glycol, thioether, polyether, cholesterol, thiocholesterol, cholic acid portion, folic acid, lipid, phospholipid, biotin, phenazine, phenanthridine, anthraquinone, adamantane, acridine, fluorescein, rhodamine, coumarin, and pigment is bound to a 5'-end or 3'-end of the oligonucleotide.

Also, the present invention provides a therapeutic agent for dyslipidemia containing the oligonucleotide as an active ingredient.

In one embodiment, the therapeutic agent is a sustained-release preparation that contains a bioabsorbable material as a carrier.

In one embodiment, the bioabsorbable material is atelocollagen or peptide gel.

Advantageous Effects of Invention

According to the present research, an oligonucleotide useful as a therapeutic agent for dyslipidemia that has excellent binding affinity to the PCSK9 gene as well as stability and safety can be provided.

BRIEF DESCRIPTION OF DRAWINGS

FIG. 1 is an image showing the results of analyzing the RNase H sensitivity of a double-strand nucleic acid composed of [γ-$^{32}$P]-labeled mRNA of PCSK9 and DNA-oligonucleotide.

FIG. 2 is an image showing the results of analyzing the RNase H sensitivity of a double-strand nucleic acid composed of [γ-$^{32}$P]-labeled mRNA of PCSK9 and BNA-oligonucleotide.

FIG. 3 is an image showing the results of analyzing the RNase H sensitivity of a double-strand nucleic acid composed of [γ-$^{32}$P]-labeled mRNA of PCSK9 and BNA-oligonucleotide or NC-oligonucleotide.

FIG. 4 is an image showing the results of analyzing the RNase H sensitivity of a double-strand nucleic acid composed of [γ-$^{32}$P]-labeled mRNA of PCSK9 and NC-oligonucleotide.

FIG. 5 is an image showing the results of analyzing the RNase H sensitivity of a double-strand nucleic acid composed of [γ-$^{32}$P]-labeled mRNA of PCSK9 and BNA-oligonucleotide.

FIG. 18 includes graphs showing serum AST levels (A), serum ALT levels (B), and serum BUN levels (C) after 6-week mouse intraperitoneal administration of PCSK9-1-BNA.

FIG. 21 includes graphs showing serum AST levels (A), serum ALT levels (B), and serum BUN levels (C) after 6-week mouse intraperitoneal administration of PCSK9-1-NC.

DESCRIPTION OF EMBODIMENTS

Figure 6A:
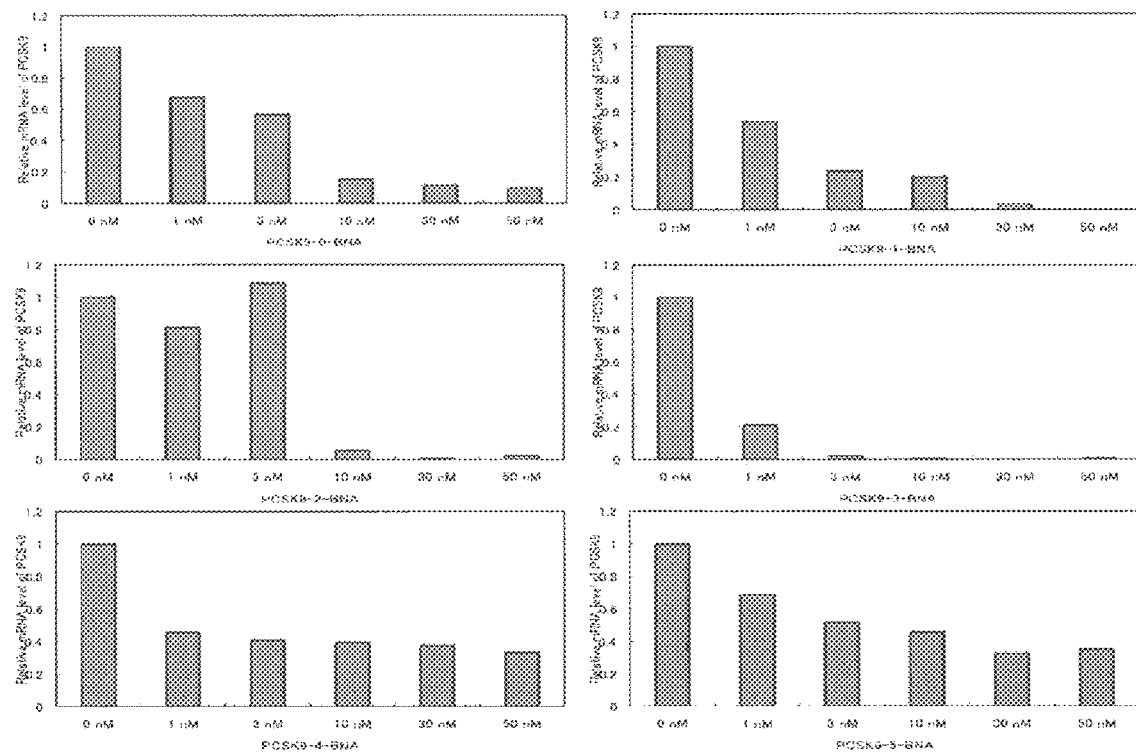
FIG. 6A includes graphs showing the PCSK9 mRNA expression levels of NMuLi cells treated with BNA-oligonucleotide.

First, the terms used herein will now be defined.

Herein, the term "$C_{1-6}$ linear alkyl group" refers to any $C_{1-6}$ linear alkyl group, or specifically, a methyl group, ethyl group, n-propyl group, n-butyl group, n-pentyl group, or n-hexyl group.

Herein, the term "$C_{1-6}$ linear alkoxy group" includes an alkoxy group that has any $C_{1-6}$ linear alkyl group. Examples include a methoxy group, ethoxy group, n-propoxy group, and the like.

Herein, the term "$C_{1-6}$ linear alkylthio group" includes an alkylthio group that has any $C_{1-6}$ linear alkyl group. Examples include a methylthio group, ethylthio group, n-propylthio group, and the like.

Herein, the term "$C_{1-6}$ linear alkylamino group" includes an alkylamino group that has one or two alkylamino groups having any $C_{1-6}$ linear alkyl group. Examples include a methylamino group, dimethylamino group, ethylamino group, methylethylamino group, diethylamino group, and the like.

Herein, the term "$C_{1-7}$ alkyl group that may form a branch or ring" includes any $C_{1-7}$ linear alkyl group, any $C_{3-7}$ branched alkyl group, and any $C_{3-7}$ cyclic alkyl group. It may be simply referred to as a "lower alkyl group". Examples of the $C_{1-7}$ linear alkyl group include a methyl group, ethyl group, n-propyl group, n-butyl group, n-pentyl group, n-hexyl group, and n-heptyl group; examples of the $C_{3-7}$ branched alkyl group include an isopropyl group, isobutyl group, tert-butyl group, isopentyl group, and the like; and examples of the $C_{3-7}$ cyclic alkyl group include a cyclobutyl group, cyclopentyl group, cyclohexyl group, and the like.

Herein, the term "$C_{2-7}$ alkenyl group that may form a branch or ring" includes any $C_{2-7}$ linear alkenyl group, any $C_{3-7}$ branched alkenyl group, and any $C_{3-7}$ cyclic alkenyl group. It may be simply referred to as a "lower alkenyl group". Examples of the $C_{2-7}$ linear alkenyl group include an ethenyl group, 1-propenyl group, 2-propenyl group, 1-butenyl group, 2-butenyl group, 1-pentenyl group, 2-pentenyl group, 3-pentenyl group, 4-pentenyl group, 1-hexenyl group, and the like; examples of the $C_{3-7}$ branched alkenyl group include an isopropenyl group, 1-methyl-1-propenyl group, 1-methyl-2-propenyl group, 2-methyl-1-propenyl group, 2-methyl-2-propenyl group, 1-methyl-2-butenyl group, and the like; and examples of the $C_{3-7}$ cyclic alkenyl group include a cyclobutenyl group, cyclopentenyl group, cyclohexenyl group, and the like.

Herein, the term "$C_{3-12}$ aryl group that may contain a hetero atom" includes any $C_{6-12}$ aromatic hydrocarbon composed solely of a hydrocarbon and any $C_{3-12}$ heteroaromatic compound containing a hetero atom (a nitrogen atom, oxygen atom, or sulfur atom) in the ring structure. Examples of the $C_{6-12}$ aromatic hydrocarbon composed solely of a hydrocarbon include a phenyl group, naphthyl group, indenyl group, azulenyl group, and the like; and examples of the $C_{3-12}$ heteroaromatic compound containing a hetero atom in the ring structure include a pyridyl group, pyrrolyl group, quinolyl group, indolyl group, imidazolyl group, furyl group, thienyl group, and the like.

Examples of the term "aralkyl group having a $C_{3-12}$ aryl portion that may have a hetero atom" include a benzyl group, phenethyl group, naphthylmethyl group, 3-phenylpropyl group, 2-phenylpropyl group, 4-phenylbutyl group, 2-phenylbutyl group, pyridylmethyl group, indolylmethyl group, furylmethyl group, thienylmethyl group, pyrrolylmethyl group, 2-pyridylethyl group, 1-pyridylethyl group, 3-thienylpropyl group, and the like.

Herein, examples of the term "halogen atom" include a fluorine atom, chlorine atom, bromine atom, and iodine atom. A fluorine atom or chlorine atom is preferable.

Herein, the term "nucleoside" refers to a glycosylamine that contains a nucleobase and a sugar. Examples of the nucleoside include, but are not limited to, naturally occurring nucleosides, abasic nucleosides, modified nucleosides, and nucleosides having a pseudo base and/or sugar group.

Herein, the term "nucleotide" refers to a glycosomine that contains a nucleobase and a sugar in which a sugar and a phosphate group are covalently bonded. The nucleotide may be optionally modified with various substituents.

Herein, the term "deoxyribonucleotide" refers to a nucleotide that has hydrogen at 2'-position of the sugar portion of the nucleotide. The deoxyribonucleotide may be optionally modified with various substituents.

Herein, the term "deoxyribonucleic acid (DNA)" refers to a nucleic acid that contains a deoxyribonucleotide.

Herein, the term "ribonucleotide" refers to a nucleotide that has hydroxy at 2'-position of the sugar portion of the nucleotide. The ribonucleotide may be optionally modified with various substituents.

Herein, the term "ribonucleic acid (RNA)" refers to a nucleic acid that contains a ribonucleotide.

Herein, the term "modified nucleoside" refers to a non-naturally occurring nucleoside among the "nucleosides" in which a purine or pyrimidine base and a sugar are bonded and to a nucleoside in which an aromatic hetero ring or aromatic hydrocarbon ring that is neither a purine nor pyrimidine and that can be used in place of a purine or pyrimidine and a sugar are bonded. Preferable examples include sugar-modified nucleosides in which the sugar portion is modified.

Herein, the term "oligonucleotide" refers to an "oligonucleotide" in which 2 to 50 identical or different "nucleosides" are bonded via a phosphodiester link. It also includes a non-naturally occurring derivative of the "oligonucleotide". Preferable examples of such derivatives include sugar derivatives in which the sugar portion is modified; thioate derivatives in which the phosphate diester portion is thioated; phosphorothioate derivatives in which the oxygen atom of the phosphate group in the phosphodiester link is replaced with a sulfur atom; esters in which the terminal phosphate portion is esterified; and amides in which the amino group on the purine base is amidated, and more preferable examples include sugar derivatives in which the sugar portion is modified.

Below, the present invention will now be described in detailed.

The oligonucleotide of the present invention contains at least one sugar-modified nucleoside at any position. The position and the number thereof are not particularly limited, and may be suitably configured according to the object. Two or more sugar-modified nucleosides may be mutually the same or may be different.

The oligonucleotide of the present invention includes an oligonucleotide in which a naturally occurring DNA or RNA is chemically modified. Such modification changes the activity of the oligonucleotide. For example, it enhances affinity to the target nucleic acid, enhances resistance to a nucleolytic enzyme (nuclease), and changes the pharmacokinetics or histological distribution of the oligonucleotide. Enhancing the affinity of the oligonucleotide to the target can make it possible to use a shorter oligonucleotide.

The oligonucleotide of the present invention can bind to the human PCSK9 gene.

Here, the term "can bind" means that a plurality of different single-strand oligonucleotides or nucleic acids can form a nucleic acid having two or more strands due to the complementarity of the nucleobase. Preferably, the term means that a double-strand nucleic acid can be formed. The melting temperature ($T_m$) of the nucleic acid having two or more strands is not particularly limited. For example, in two different single-strand oligonucleotides or nucleic acids that form a double-strand nucleic acid, it is not necessary that the base sequences of the double-strand forming regions are completely complementary to each other.

The human PCSK9 gene contains the base sequence of SEQ ID NO. 1 (GenBank accession number: NM_174936; a coding region, 2079 bases), and encodes the amino acid sequence of SEQ ID NO. 2. The PCSK9 gene is involved in decomposition of the LDL receptor.

The region of the human PCSK9 gene to which the oligonucleotide of the present invention can bind is preferably a region composed of a base sequence containing any of the following base sequences: base sequence of SEQ ID NO. 3; base sequence of SEQ ID NO. 4; base sequence of SEQ ID NO. 5; base sequence of SEQ ID NO. 6; base sequence of SEQ ID NO. 7; base sequence of SEQ ID NO. 8; base sequence of SEQ ID NO. 9; base sequence of SEQ ID NO. 10; base sequence of SEQ ID NO. 11; base sequence of SEQ ID NO. 12; base sequence of SEQ ID NO. 13; base sequence of SEQ ID NO. 14; base sequence of SEQ ID NO. 15; base sequence of SEQ ID NO. 16; base sequence of SEQ ID NO. 17; base sequence of SEQ ID NO. 18; or base sequences complementary to these. More preferably, it is a DNA or RNA composed of these base sequences.

The sugar-modified nucleoside contained in the oligonucleotide of the present invention has a bridging structure between 4'-position and 2'-position.

One example of the bridging structure is represented by —$CH_2$—O— or —$(CH_2)_2$—O—. Hereinafter, such a bridging structure may be referred to as BNA.

Examples of the BNA include, but are not limited to, α-L-methyleneoxy (4'-$CH_2$—O-2'), β-D-methyleneoxy (4'-$CH_2$—O-2'), and ethyleneoxy (4'-$(CH_2)_2$—O-2'). The BNA nucleoside (monomer) and an oligonucleotide containing it can be synthesized by methods described in, for example, Non Patent Literatures 3 to 7.

Another example of the bridging structure is represented by —$CH_2$—$NR^1$—O— or —$(CH_2)_2$—NR'-O—, wherein $R^1$ is a hydrogen atom;

a $C_{1-7}$ alkyl group that may form a branch or ring;

a $C_{2-7}$ alkenyl group that may form a branch or ring;

a $C_{3-12}$ aryl group that may form any one or more substituents selected from an α group consisting of a hydroxyl group, $C_{1-6}$ linear alkyl group, $C_{1-6}$ linear alkoxy group, mercapto group, $C_{1-6}$ linear alkylthio group, amino group, $C_{1-6}$ linear alkylamino group, and halogen atom, and that may contain a hetero atom; or an aralkyl group having a $C_{3-12}$ aryl portion that may have any one or more substituents selected from the α group and that may contain a hetero atom. Hereinafter, such a bridging structure may be referred to as NC.

Examples of NC include, but are not limited to, oxyamino (4'-$CH_2$—NH—O-2') and N-methyloxyamino (4'-$CH_2$—$NCH_3$–O-2'). The NC nucleoside (monomer) and an oligonucleotide containing it can be synthesized by methods described in, for example, Non Patent Literatures 8 to 11.

Another example of the bridging structure is represented by —CO—$NR^1$—, —$CH_2$—CO—$NR^1$—, —$(CH_2)_2$—CO—$NR^1$—, —CO—$NR^1$—X—, or —$CH_2$—CO—$NR^1$—X —, wherein $R^1$ is a hydrogen atom;

a $C_{1-7}$ alkyl group that may form a branch or ring;

a $C_{2-7}$ alkenyl group that may form a branch or ring;

a $C_{3-12}$ aryl group that may have any one or more substituents selected from an α group consisting of a hydroxyl group, $C_{1-6}$ linear alkyl group, $C_{1-6}$ linear alkoxy group, mercapto group, $C_{1-6}$ linear alkylthio group, amino group, $C_{1-6}$ linear alkylamino group, and halogen atom, and that may contain a hetero atom; or an aralkyl group having a $C_{3-12}$ aryl portion that may have any one or more substituents selected from the α group and that may contain a hetero atom; and X is an oxygen atom, sulfur atom, amino group, or methylene group. Hereinafter, such a bridging structure may be referred to as CON.

Examples of CON include, but are not limited to, unsubstituted amide (4'-CO—NH-2'), N-methylamide (4'-CO—$NCH_3$-2'), acetamide (4'-$CH_2$—CO—NH-2'), N-methylacetamide (4'$CH_2$—CO—$NCH_3$-2'), N-oxyacetamide (4'-$CH_2$—CO—NH—O-2'), and N-methyl-N-oxyacetamide (4'-$CH_2$—CO—$NCH_3$—O-2'). The CON nucleoside (monomer) and an oligonucleotide containing it can be synthesized by methods described in, for example, the examples below.

The length of the base sequence of the oligonucleotide of the present invention is not particularly limited, and it is preferably 10 to 25 bases, and more preferably 13 to 20 bases.

The structure of the 5'-end or 3'-end of the oligonucleotide of the present invention is not particularly limited. For example, at least one selected from the group consisting of an intercalator, reporter molecule, polyamine, polyamide, polyethylene glycol, thioether, polyether, cholesterol, thiocholesterol, cholic acid portion, folic acid, lipid, phospholipid, biotin, phenazine, phenanthridine, anthraquinone, adamantane, acridine, fluorescein, rhodamine, coumarin, and pigment is bound. Preferably, cholesterol is bound to the 5'-end or 3'-end. Due to the binding of cholesterol, it can be expected that the in vivo stability of the oligonucleotide is enhanced and the uptake thereof into the liver, which is the target organ, is enhanced. The method for binding cholesterol to the 5'-end or 3'-end is not particularly limited. Examples include a method in which cholesterol is introduced as an amidite, a method in which cholesterol is introduced as a solid-phase carrier for oligonucleotide synthesis, and a method in which cholesterol is conjugated after an oligonucleotide is synthesized.

The oligonucleotide containing a sugar-modified nucleoside, or in particular, a sugar-modified nucleoside in which sugar modification is CON, is fixed by the bridging structure, or in particular, a bridging structure containing an amide bond, between 4'-position and 2'-position as described above, is therefore unlikely to be decomposed by various nucleases, and can exist in a living body for a long period of time after being administered into the living body. For example, the oligonucleotide forms a stable double strand with the mRNA and inhibits biosynthesis of the pathogenic protein (an antisense method), or forms a triple strand with a double-strand DNA in the genome and inhibits transcription to the mRNA. Also, the oligonucleotide makes it possible to suppress proliferation of a virus that has infected. Also, it is expected that the bridging structure containing an amide bond has a high level of biocompatibility, and thus it can be expected that the oligonucleotide also functions as an aptamer for recognizing a biogenic substance such as protein.

Accordingly, it is expected that the oligonucleotide of the present invention is useful as a pharmaceutical agent (antisense nucleic acid), such as an antitumor agent or an antiviral agent, that treats the disease by inhibiting the function of a specific gene.

In particular, the antisense method requires both binding affinity to the mRNA of the target human PCSK9 and resistance to nucleases in the living body. Generally, it is known that the structure of the sugar portion of a nucleic acid in a single-strand state continuously fluctuate between a form that is similar to a DNA double strand and a form that is similar to a DNA-RNA double strand or RNA double strand. When a single-strand nucleic acid forms a double strand with a complementary RNA chain, the structure of its sugar portion is fixed. The oligonucleotide of the present invention has a sugar portion that is fixed in advance into a state for forming a double strand, and is therefore likely to form a double strand with the target RNA chain and can stably exist. Also, it is known that the nucleic acid double strand is stabilized by hydrated water that is connected into a chain called a water molecule network. The bridging structure containing an amide bond of the present invention is highly hydrophilic and therefore can be more stabilized. Moreover, the amide bond that bridges the sugar portion is unlikely to be recognized by a biological enzyme and can greatly contribute to the nuclease resistance of the oligonucleotide.

The oligonucleotide of the present invention binds to the mRNA of human PCSK9, for example, as an antisense nucleic acid and can suppress the expression of the human PCSK9 gene. Suppression of the expression of the human PCSK9 gene increases the level of LDL receptor protein expression and facilitates the cellular uptake and metabolism of LDL, and thereby the blood LDL concentration can be lowered. In this way, the oligonucleotide of the present invention demonstrates an effect as a therapeutic agent for dyslipidemia.

The therapeutic agent for dyslipidemia that contains the oligonucleotide of the present invention as an active ingredient may be blended with, for example, an auxiliary agent that is usually used in the technical field of pharmaceutical formulations, such as an excipient, binder, preservative, oxidation stabilizer, disintegrator, lubricant, or corrigent, and formulated into a parenteral preparation or liposomal preparation. Also, the therapeutic agent for dyslipidemia may be blended with a pharmaceutical carrier that is usually used in this technical field and formulated into a topical preparation such as a solution, cream, or ointment. Preferably, the therapeutic agent may be formulated into a sustained-release preparation. The carrier for the sustained-release preparation is not particularly limited, and preferably it is a bioabsorbable material. The bioabsorbable material is not particularly limited, and examples include atelocollagen, peptide gel, hyaluronic acid gel, fibrin adhesive, alginic acid gel, and poly(α-hydroxy acid). Atelocollagen and peptide gel are preferable. For example, kneading the oligonucleotide of the present invention and the bioabsorbable material can give a sustained-release preparation.

EXAMPLES

The present invention will now be described below using examples. However, it goes without saying that the present invention is not limited to the following examples.

Example 1

Synthesis of CON Monomer (Amidite)

Synthesis of nucleoside analog: 2'-amino-3'-O-[2-cyanoethoxy(diisopropylamino)phosphino]-5'-O-dimethoxytrityl-2'-N,4'-C-oxomethylenethymidine (compound 16)

[Formula 1]

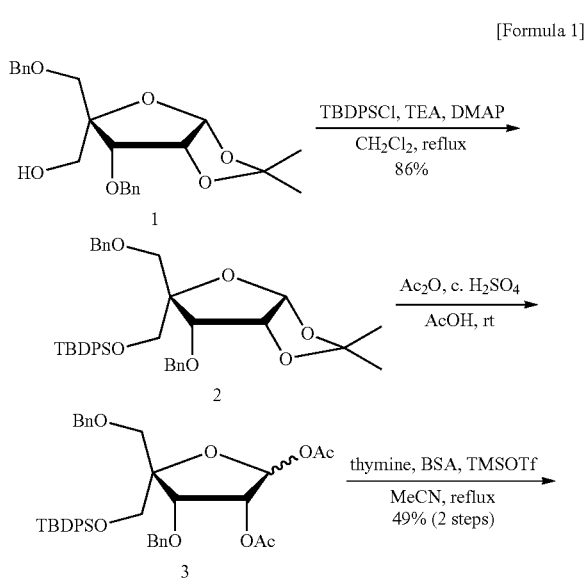

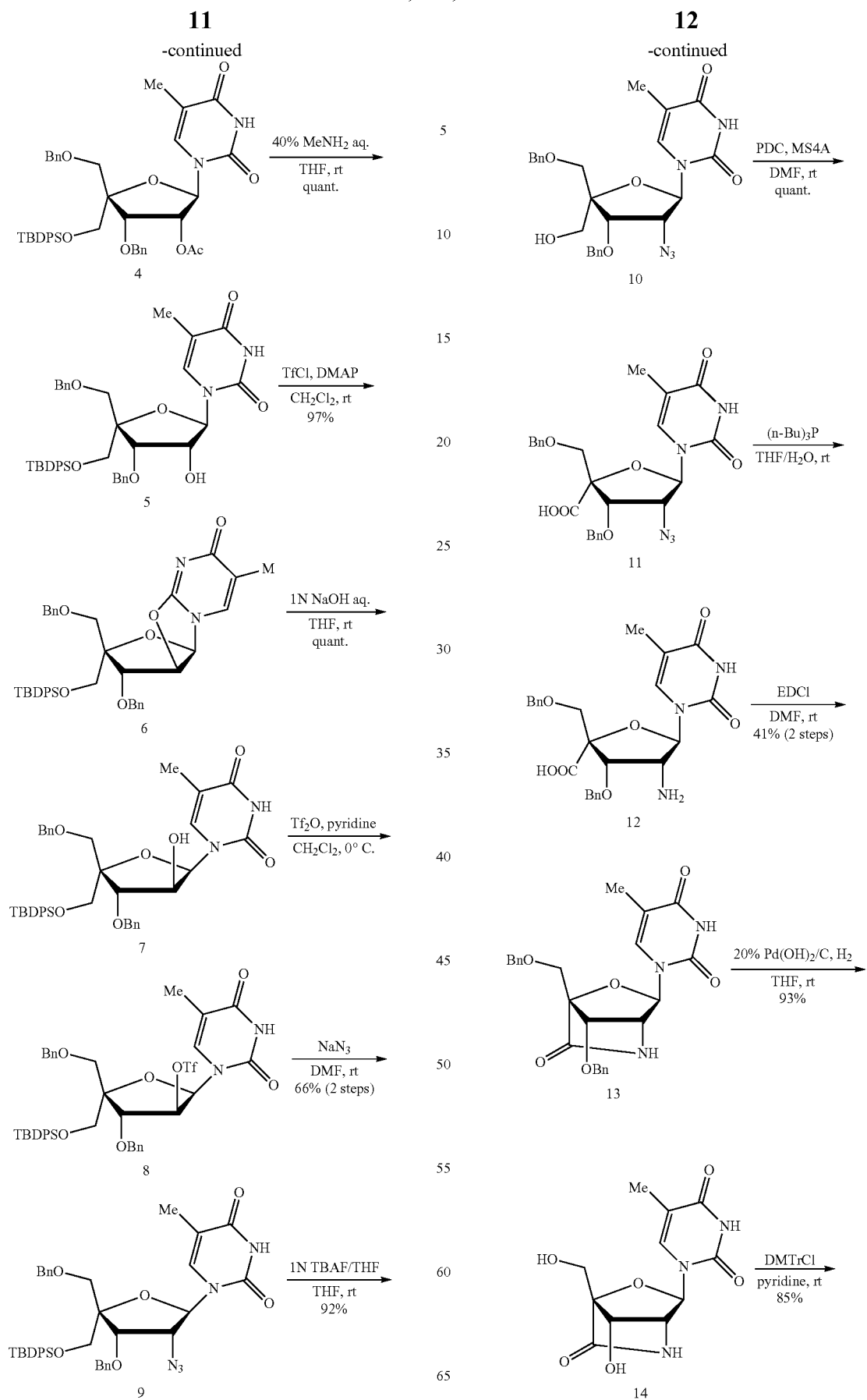

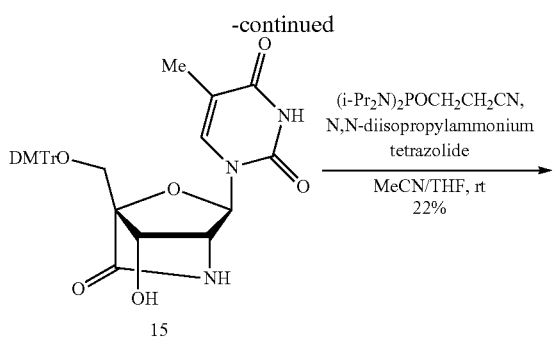

(1) Synthesis of Compound 2

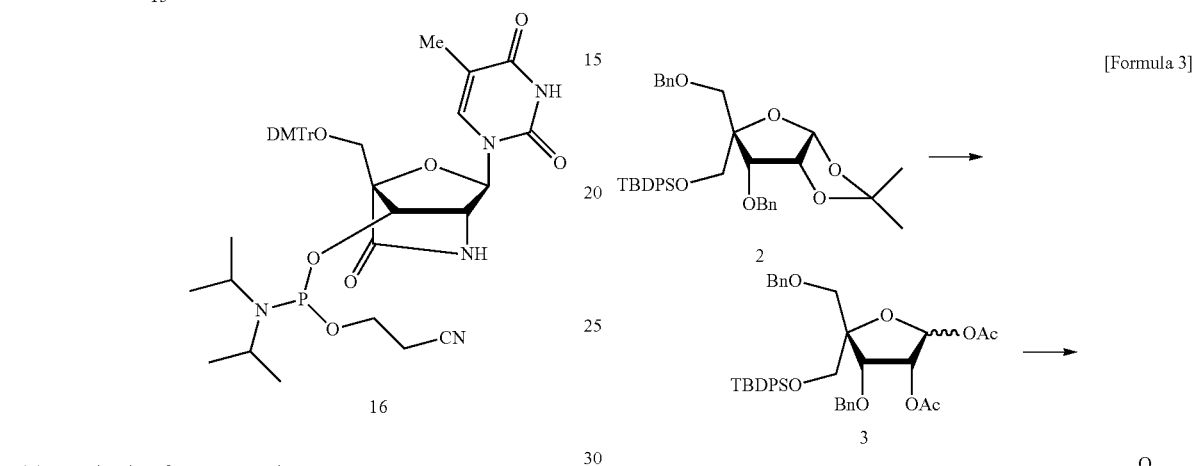

Under a nitrogen stream, triethylamine (15.1 mL, 110 mmol) was added to a dichloromethane solution (80 mL) of compound 1 (14.7 g, 36.8 mmol), then dimethyl aminopyridine (0.90 g, 7.36 mmol) and tert-butyldimethylsilyl chloride (15.1 mL, 58.9 mmol) were added under ice-cooling, and the solution was refluxed. Note that compound 1 can be prepared according to A. A. Koshkin et al., Tetrahedron, 1998, vol. 54, pp. 3607-3630 and S. K Singh et al., Chem. Commun., 1998, pp. 455-456. After 20 hours, water was added, the solution was extracted with methylene chloride, and then the organic layer was washed with water and saturated brine and dried over anhydrous sodium sulfate. The obtained crude product was purified by silica gel chromatography (n-hexane:ethyl acetate=9:1 (v/v)), thus giving compound 2 (20.4 g, yield 85.9%) as oil.

The physical property data of the obtained compound 2 is as follows: $[\alpha]_D^{25}$ +84.8 (c 1.00, CHCl$_3$); IR (KBr): 1457, 1372, 1105, 1025 cm$^{-1}$; $^1$H-NMR (270 MHz, CDCl$_3$): δ1.03 (9H, s), 1.29 (6H, s), 3.62, 3.73 (2H, AB, J=10.5 Hz), 4.03, 4.08 (2H, AB, J=11.3 Hz), 4.20 (1H, d, J=5.1 Hz), 4.45, 4.55 (2H, AB, J=11.9 Hz), 4.49, 4.66 (2H, AB, J=12.2 Hz), 4.58 (1H, dd, J=5.1 Hz, 4.1 Hz), 5.76 (1H, d, J=4.1 Hz), 7.21-7.70 (20H, m); $^{13}$C-NMR (75.45 MHz, CDCl$_3$): δ19.9, 26.9, 27.2, 27.5, 65.3, 72.6, 73.0, 74.2, 78.8, 80.2, 88.2, 104.8, 113.8, 128.2, 128.2, 128.3, 128.3, 128.8, 128.9, 130.1, 133.9, 134.1, 135.4, 136.3, 136.4, 138.5, 138.7; MS (FAB): m/z 661 (MNa$^+$): calculated C$_{39}$H$_{46}$O$_6$Si: C, 73.32; H, 7.26, measured C, 73.44; H, 7.32.

(2) Synthesis of Compound 4

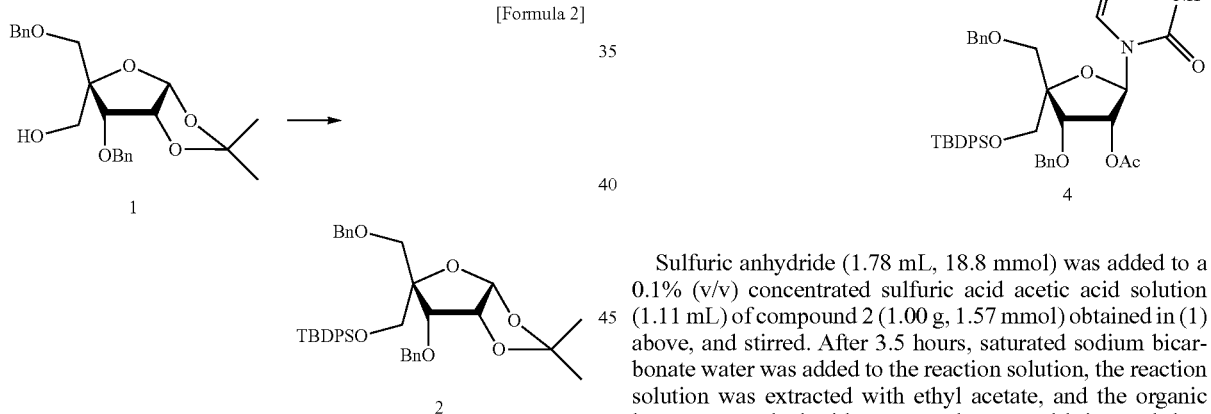

Sulfuric anhydride (1.78 mL, 18.8 mmol) was added to a 0.1% (v/v) concentrated sulfuric acid acetic acid solution (1.11 mL) of compound 2 (1.00 g, 1.57 mmol) obtained in (1) above, and stirred. After 3.5 hours, saturated sodium bicarbonate water was added to the reaction solution, the reaction solution was extracted with ethyl acetate, and the organic layer was washed with water and saturated brine and then dried over anhydrous sodium sulfate. After distilling off the solvent, the crude product (1.07 g) of compound 3 was obtained as oil, and used for the subsequent thymine introduction.

Under a nitrogen stream, thymine (297 mg, 2.36 mmol) was added to an acetonitrile solution (5 mL) of the crude product of compound 3 and dissolved in a 40° C. oil bath, then N,O-bistrimethylsilylacetamide (1.34 mL, 5.50 mmol) and trimethylsilyl trifluoromethanesulfonate (0.28 mL, 1.57 mmol) were added at room temperature, and the solution was refluxed and stirred for 1 hour. Saturated sodium bicarbonate water was added, the solution was extracted with ethyl acetate, and the organic layer was washed with water and saturated brine and then dried over anhydrous sodium sulfate. After distilling off the solvent, the obtained crude product was purified by silica gel chromatography (n-hexane:ethyl acetate=10:1→1:1 (v/v)), thus giving compound 4 (367 mg, yield 49%) as white amorphous.

The physical property data of the obtained compound 4 was as follows: melting point: 55-59° C.; $[\alpha]_D^{24}$-11.7 (c 0.800, CHCl$_3$); IR (KBr): 1747, 1693, 1232, 1113 cm$^{-1}$; $^1$H-NMR (300 MHz, CDCl$_3$): δ1.04 (9H, s), 1.52 (3H, s), 1.96 (3H, s), 3.71, 3.76 (2H, AB, J=10.5 Hz), 3.69, 3.94, (2H, AB, J=10.8 Hz), 4.41 (1H, d, J=6.0 Hz), 4.54, 4.58 (2H, AB, J=12.6 Hz), 4.54, 4.58 (2H, AB, J=12.6 Hz), 5.38 (1H, t, J=6.0 Hz), 6.16 (1H, d, J=6.0 Hz), 7.18-7.63 (20H, m), 7.87 (1H, s); $^{13}$C-NMR (75.45 MHz, CDCl$_3$): δ12.0, 19.2, 20.6, 26.9, 63.8, 72.2, 73.7, 74.6, 74.9, 77.7, 85.5, 87.9, 111.3, 127.6, 127.7, 127.7, 127.8, 128.1, 128.3, 128.6, 129.7, 129.9, 132.6, 132.9, 135.5, 135.7, 135.7, 137.2, 137.5, 150.4, 163.6, 170.2; MS (FAB): m/z 749 (MH$^+$), calculated C$_{43}$H$_{48}$N$_2$O$_8$Si: C, 68.96; H, 6.46; N, 3.74. measured C, 68.92; H, 6.45; N, 3.74.

(3) Synthesis of Compound 5

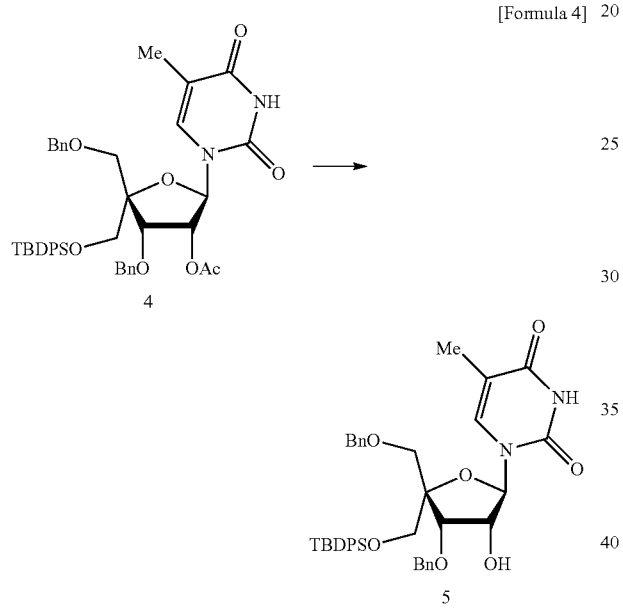

[Formula 4]

A 40% (v/v) methylamine solution (1.1 mL, 13 mmol) was added to a tetrahydrofuran solution (2.4 mL) of compound 4 (326 mg, 0.435 mmol) obtained in (2) above, and stirred for 30 minutes at room temperature. After distilling off the solvent, the solution was extracted with ethyl acetate, and the organic layer was dried over anhydrous sodium sulfate. After distilling off the solvent, the obtained crude product was purified by flash column chromatography (n-hexane:ethyl acetate=1:1 (v/v)), thus giving compound 5 (312 mg, yield 100%) as white amorphous.

The physical property data of the obtained compound 5 was as follows: melting point: 61-63° C.; $[\alpha]_D^{25}$-12.2 (c 0.750, CHCl$_3$); IR (KBr): 3403, 3175, 1688, 1468, 1272, 1113 cm$^{-1}$; $^1$H-NMR (270 MHz, CDCl$_3$): δ1.06 (9H, s), 1.60 (3H, s), 3.54, 3.63 (2H, AB, J=10.5 Hz), 3.64 (1H, d, J=10.8 Hz), 3.73, 3.83 (2H, AB, J=10.5 Hz), 4.31 (1H, d, J=4.9 Hz), 4.41 (1H, ddd, J=4.9 Hz, 4.9 Hz, 10.8 Hz), 4.50 (2H, s), 4.67, 4.73 (2H, AB, J=11.1 Hz), 5.95 (1H, d, J=4.9 Hz), 7.21-7.66 (20H, m), 8.12 (1H, s); $^{13}$C-NMR (67.80 MHz, CDCl$_3$): δ12.1, 19.1, 26.8, 64.2, 72.2, 73.8, 74.2, 74.5, 77.2, 78.5, 88.1, 90.9, 110.9, 127.7, 127.8, 127.9, 128.0, 128.1, 128.2, 128.6, 130.0, 132.2, 132.2, 135.6, 135.7, 136.5, 137.2, 150.3, 163.4; MS (FAB): m/z 707 (MH$^+$). calculated C$_{41}$H$_{46}$N$_2$O$_7$Si: C, 69.66; H, 6.56; N, 3.96. measured C, 69.59; H, 6.59; N, 3.93.

(4) Synthesis of Compound 6

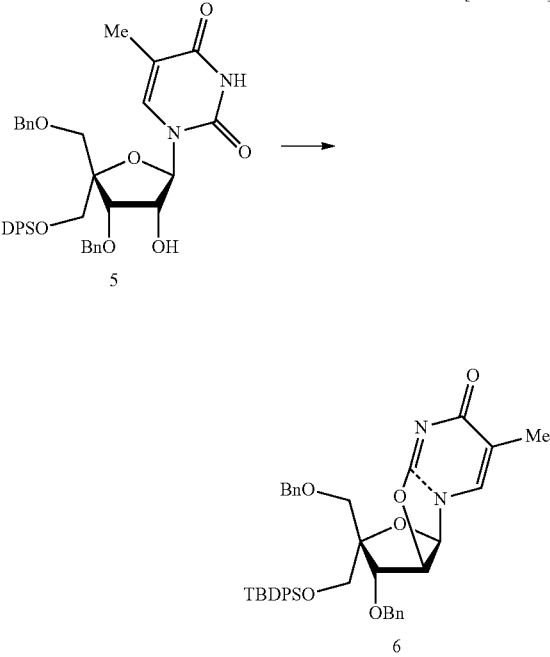

[Formula 5]

Under a nitrogen stream, dimethylaminopyridine (181 mg, 1.48 mmol) was added to a dichloromethane solution (7 mL) of compound 5 (262 mg, 0.37 mmol) obtained in (3) above. Trifluoromethanesulfonyl chloride (0.12 mL, 1.11 mmol) was added under ice-cooling, the temperature was gradually increased to room temperature, and then the solution was stirred for 1 hour. Saturated sodium bicarbonate water was added, the solution was extracted with dichloromethane, and the organic layer was washed with saturated brine and then dried over anhydrous sodium sulfate. After distilling off the solvent, compound 6 (248 mg, yield 97%) was obtained as white amorphous.

The physical property data of the obtained compound 6 was as follows: melting point: 51-54° C.; $[\alpha]_D^{26}$-33.5 (c 1.000, CHCl$_3$); IR (KBr): 1667, 1650, 1563, 1482, 1112 cm$^{-1}$; $^1$H-NMR (300 MHz, CDCl$_3$): δ1.03 (9H, s), 1.99 (3H, s), 3.29, 3.34 (2H, AB, J=10.8 Hz), 3.68, 3.82 (2H, AB, J=10.5 Hz), 4.31 (1H, d, J=3.9 Hz), 4.32, 4.38 (2H, AB, J=12 Hz), 4.60, 4.81 (2H, AB, J=11.4 Hz), 5.50 (1H, dd, J=6.3, 3.9 Hz), 6.23 (1H, d, J=6.3 Hz), 7.08-7.66 (21H, m); $^{13}$C-NMR (75.45 MHz, CDCl$_3$): δ14.0, 18.9, 26.7, 64.0, 69.4, 73.4, 84.0, 87.1, 88.7, 89.9, 119.0, 127.4, 127.6, 127.7, 127.8, 128.1, 128.3, 128.4, 128.5, 129.8, 129.8, 130.1, 131.9, 132.3, 135.3, 135.5, 136.4, 137.0, 159.2, 172.3; MS (FAB): m/z 689 (MH$^+$), calculated C$_{41}$H$_{44}$N$_2$O$_6$Si: C, 71.48; H, 6.44; N, 4.07. measured C, 71.38; H, 6.49; N, 4.08.

(5) Synthesis of Compound 7

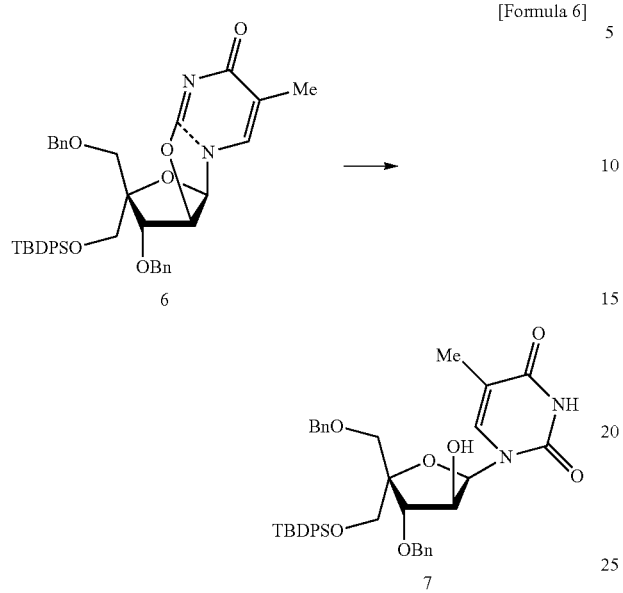

[Formula 6]

A 1 N aqueous sodium hydroxide solution (1.90 mL) was added to a tetrahydrofuran solution (11 mL) of compound 6 (510 mg, 0.74 mmol) obtained in (4) above, and stirred for 11.5 hours at room temperature. After neutralization with an aqueous ammonium chloride solution, the solvent was distilled off, the solution was extracted with dichloromethane, and the organic layer was washed with saturated sodium bicarbonate water and then dried over anhydrous sodium sulfate. After distilling off the solvent, the obtained crude product was purified by flash column chromatography (n-hexane:ethyl acetate=1:1 (v/v)), thus giving compound 7 (524 mg, yield 100%) as white amorphous.

The physical property data of the obtained compound 7 was as follows: melting point: 67-70° C.; $[\alpha]_D^{26}$+24.5 (c 0.840, CHCl$_3$); IR (KBr): 3347, 3184, 1690, 1471 cm$^{-1}$; $^1$H-NMR (270 MHz, CDCl$_3$): δ1.02 (9H, s), 1.65 (3H, s), 3.48, 3.70 (2H, AB, J=10.3 Hz), 3.50 (1H, d, J=7.0 Hz), 3.62, 3.76 (2H, AB, J=10.8 Hz), 4.22 (1H, d, J=7.0 Hz), 4.51, 4.78 (2H, AB, J=7.6 Hz), 4.54 (1H, d, J=11.6 Hz), 4.69 (1H, ddd, J=5.1, 7.0, 7.6 Hz), 6.15 (1H, d, J=5.1 Hz), 7.29-7.64 (20H, m), 8.10 (1H, s); $^{13}$C-NMR (67.80 MHz, CDCl$_3$): δ12.0, 18.8, 26.5, 63.9, 69.7, 72.6, 73.6, 75.3, 81.9, 85.3, 85.5, 109.5, 127.5, 127.6, 127.8, 128.0, 128.2, 128.5, 129.5, 129.6, 132.4, 135.4, 135.5, 136.8, 137.2, 137.9, 151.1, 164.3; MS (FAB): m/z 707 (MH$^+$), calculated C$_{41}$H$_{46}$N$_2$O$_7$Si: C, 69.66; H, 6.56; N, 3.96. measured C, 69.42; H, 6.54; N, 3.97.

(6) Synthesis of Compound 9

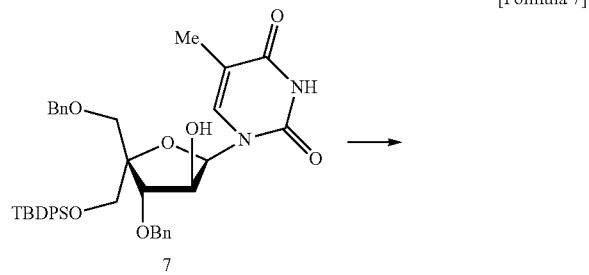

[Formula 7]

Under a nitrogen stream, pyridine (1.65 mL, 20.5 mmol) and trifluoromethanesulfonic anhydride (1.37 mL, 8.20 mmol) were added to a dichloromethane solution (40 mL) of compound 7 (2.86 g, 4.10 mmol) obtained in (5) above under ice-cooling, and stirred for 1 hour under ice-cooling conditions. After the acid anhydride was decomposed by adding water, the solution was extracted with dichloromethane, and the organic layer was dried over anhydrous sodium sulfate. After distilling off the solvent, the obtained crude product was obtained as yellow oil, and briefly purified by flush column chromatography (n-hexane:ethyl acetate=3:1→2:1 (v/v)), thus giving a crude product of compound 8 as pale yellow amorphous.

Next, under a nitrogen stream, sodium azide (0.23 g, 3.60 mmol) was added to a dimethylformamide solution (80 mL) of compound 8 (1.96 g, 2.34 mmol) and stirred. After 48 hours, the solvent was distilled off, water was added, the solution was extracted with dichloromethane, and the organic layer was washed with saturated brine and then dried over anhydrous sodium sulfate. After distilling off the solvent, the obtained crude product was purified by flash column chromatography (n-hexane:ethyl acetate=3:1), thus giving compound 9 (1.71 g, yield 100%) as white amorphous.

The physical property data of the obtained compound 9 was as follows: melting point: 53-56° C.; $[\alpha]_D^{27}$−32.7 (c 0.840, CHCl$_3$); IR (KBr): 3175, 2109, 1686, 1268, 1111 cm$^{-1}$; $^1$H-NMR (300 MHz, CDCl$_3$): δ0.99 (9H, s), 1.58 (3H, s), 3.63, 3.69 (2H, AB, J=10.5 Hz), 3.69, 3.91 (2H, AB, J=10.5 Hz), 3.91 (1H, dd, J=7.2 Hz, 5.4 Hz), 4.23 (1H, d, J=5.4 Hz), 4.47, 4.53 (2H, AB, J=11.4 Hz), 4.57, 4.75 (2H, AB, J=11.4 Hz), 6.03 (1H, d, J=7.2 Hz), 7.23-7.60 (20H, m), 8.70 (1H, s); $^{13}$C-NMR (75.45 MHz, CDCl$_3$): δ12.1, 19.1, 26.9, 64.0, 64.6, 72.4, 73.8, 74.6, 79.5, 85.2, 87.9, 111.3, 127.7, 127.7, 127.8, 128.0, 128.2, 128.4, 128.7, 129.7, 129.9, 132.5, 132.8, 135.1, 135.5, 135.7, 136.6, 136.9, 150.2, 163.4; MS (FAB): m/z 732 (MH$^+$), calculated C$_{41}$H$_{45}$N$_5$O$_6$Si: C, 67.28; H, 6.20; N, 9.57. measured C, 67.25; H, 6.27; N, 9.45.

(7) Synthesis of Compound 10

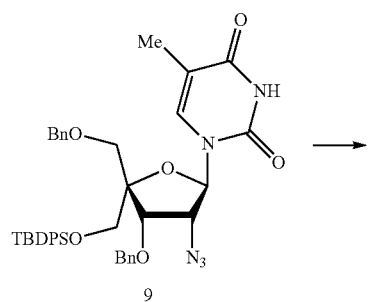

[Formula 8]

9

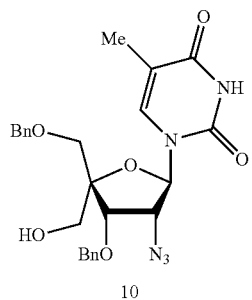

10

Under a nitrogen stream, a tetrahydrofuran solution (2.20 mL, 2.20 mmol) of 1 N tetrabutylammonium fluoride was added to a tetrahydrofuran solution (30 mL) of compound 9 (1.10 g, 1.50 mmol) obtained in (6) above, and stirred for 12.5 hours. After distilling off the solvent, water and ethyl acetate were added in sequence, and the organic layer was dried over anhydrous sodium sulfate. After distilling off the solvent, the crude product was purified by flash column chromatography (hexane:ethyl acetate=10:1 (v/v)→ethyl acetate only), thus giving compound 10 (682.2 mg, yield 92%) as oil.

The physical property data of the obtained compound 10 was as follows: melting point 41-45° C.; $[\alpha]_D^{25}$+13.3 (c 0.950, CHCl$_3$); IR (KBr): 3435, 2113, 1694, 1459, 1268, 1097 cm$^{-1}$; $^1$H-NMR (300 MHz, CDCl$_3$): δ1.63 (3H, s), 2.09 (1H, br), 3.73 (1H, s), 4.04 (1H, t, J=6.3 Hz), 4.39 (1H, d, J=6.3 Hz), 4.51, 4.55 (2H, AB, J=10.2 Hz), 4.56, 4.91 (2H, AB, J=11.4 Hz), 6.18 (1H, d, J=6.3 Hz), 7.26-7.44 (10H, m), 8.50 (1H, s); $^{13}$C-NMR (75.45 Hz, CDCl$_3$): δ12.2, 63.4, 64.9, 71.8, 73.8, 74.8, 79.4, 86.4, 87.5, 111.5, 127.7, 128.2, 128.2, 128.6, 128.7, 128.8, 135.2, 136.5, 137.0, 150.3, 163.5; MS (FAB): m/z 494 (MH$^+$), high resolution MS (FAB): calculated C$_{25}$H$_{28}$N$_5$O$_6$ (MH$^+$): 494.2040. measured 494.2045.

(8) Synthesis of Compound 11

[Formula 9]

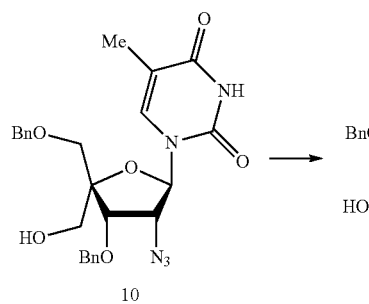 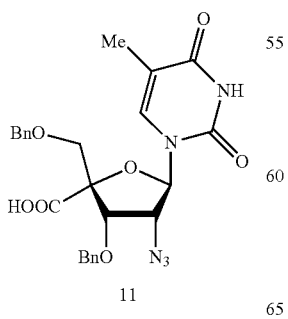

10    11

Under a nitrogen stream, powder molecular sieves 4 Å (0.31 g) and pyridinium dichromate (1.50 g, 4.00 mmol) were added in sequence to a dimethylformamide suspension (3.1 mL) of compound 10 (0.20 g, 0.40 mmol) obtained in (7) above, and stirred under room temperature conditions. After 4.5 hours, water was added and stirred for several minutes, and then acetic acid (2 mL) was added and further stirred for 1 hour. After the suspension was diluted with ethyl acetate, filtered through Celite®, and extracted with ethyl acetate. The organic layer was washed with a 0.4 M aqueous oxalic acid solution (30 mL) and a 0.3 M aqueous ammonium oxalate solution (30 mL), and then dried over anhydrous sodium sulfate. After distilling off the solvent, compound 11 (0.20 g, yield 100%) was obtained as a pale yellow solid.

The physical property data of the obtained compound 11 was as follows: $^1$H-NMR (300 MHz, CDCl$_3$): δ1.64 (3H, s), 3.83 (1H, dd, J=8.4, 5.4 Hz), 3.84, 4.12 (2H, AB, J=10.5 Hz), 4.45 (1H, d, J=5.4 Hz), 4.59, 4.65 (2H, AB, J=11.4 Hz), 4.75, 4.82 (2H, AB, J=10.5 Hz), 5.89 (1H, br), 6.54 (1H, d, J=8.4 Hz), 7.28-7.44 (10H, m), 7.99 (1H, s), 9.31 (1H, br); MS (FAB): m/z 508 (MH$^+$), high resolution MS (FAB): calculated C$_{25}$H$_{25}$N$_5$O$_7$ (MH$^+$): 508.1832. measured 508.1825.

(9) Synthesis of Compound 13

[Formula 10]

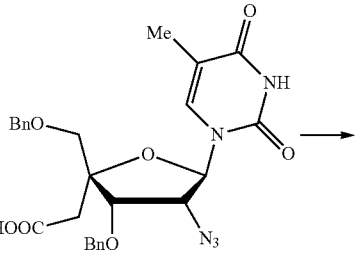

11

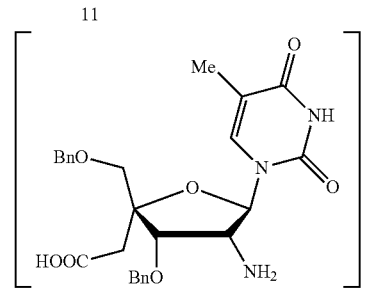

12

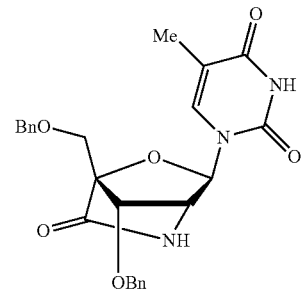

13

Compound 11 (389.7 mg, 0.77 mmol) obtained in (8) above was dissolved in a mixed solution (0.8 mL) of water: tetrahydrofuran=1:3, and tributyl phosphine (0.96 mL, 3.85 mmol) was added and stirred at room temperature. After 3.5 hours, the product from which the solvent had been distilled off was dissolved in methanol and washed with hexane. After distilling off the solvent, a crude product (380 mg) of compound 12 was obtained as oil, and used for the subsequent ring-closing reaction.

Under a nitrogen stream, 1-ethyl-3-(3-dimethylaminopropyl)carbodiimide hydrochloride (221 mg, 1.16 mmol) was added to a DMF solution (11 mL) of compound 12 under ice-cooling, and stirred for 21.5 hours at room temperature. After distilling off the solvent, the solution was extracted with ethyl acetate, and the organic layer was dried over anhydrous sodium sulfate. After distilling off the solvent, the crude product was purified by column chromatography (hexane:ethyl acetate=5:1 (v/v)→ethyl acetate only), thus giving compound 13 (191.3 mg, yield 53.6%) as oil.

The physical property data of the obtained compound 13 was as follows: $[\alpha]_D^{25}$+62.1 (c 0.400, CHCl$_3$); IR (KBr): 3186, 1692, 1469, 1455, 1272, 1112 cm$^{-1}$; $^1$H-NMR (300 MHz, CDCl$_3$): δ1.61 (3H, s), 3.96, 4.11 (2H, AB, J=11.4 Hz), 4.13 (1H, s), 4.22 (1H, s), 4.56 (2H, s), 4.60, 4.67 (2H, AB, J=11.4 Hz), 5.45 (1H, s), 6.58 (1H, br), 7.21-7.56 (10H, m), 7.57 (1H, s), 9.24 (1H, br); $^{13}$C-NMR (67.80 Hz, CDCl$_3$): 12.3, 58.4, 63.0, 72.4, 74.0, 78.3, 86.2, 86.6, 110.9, 127.8, 127.8, 128.1, 128.3, 128.5, 128.6, 135.1, 136.2, 137.4, 142.0, 150.5, 163.8, 174.3; MS (FAB): m/z 464 (MH$^+$).

(10) Synthesis of Compound 14

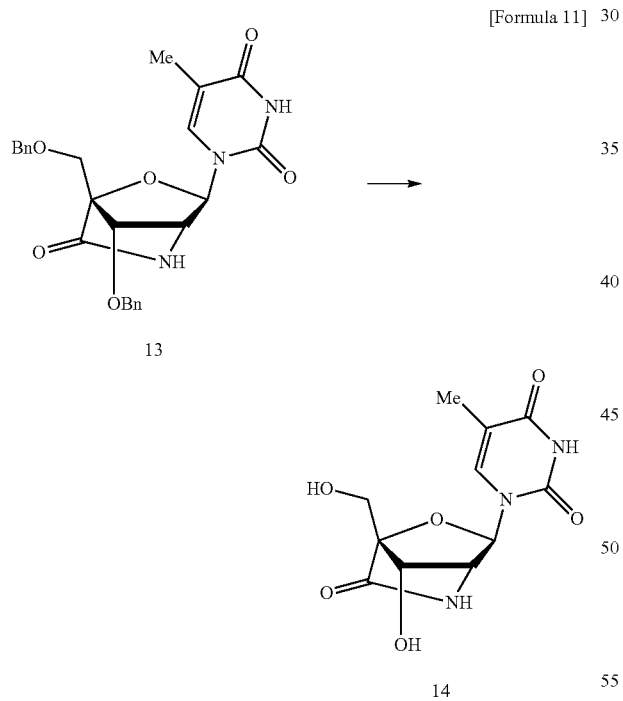

Under a nitrogen stream, 20% (v/v) palladium hydroxide on carbon (100 mg) was added to 2.2 mL of a tetrahydrofuran solution of compound 13 (101 mg, 0.22 mmol) obtained in (9) above, and stirred for 3 hours. The compound was hot-filtered and washed with hot methanol (150 mL), and then the solvent was distilled off, thus giving a crude product. Recrystallization was carried out using methanol, thus giving compound 14 (57.2 mg, yield 93%) as white solids.

The physical property data of the obtained compound 14 was as follows: $[\alpha]_D^{25}$+31.6 (c 0.700, CH$_3$OH); IR (KBr): 3255, 2925, 2852, 1692, 1466, 1231, 1065 cm$^{-1}$; $^1$H-NMR (300 MHz, CD$_3$OD): δ1.89 (3H, s), 3.88, 4.04 (2H, AB, J=12.9 Hz), 4.12 (1H, s), 4.30 (1H, s), 5.38 (1H, s), 7.86 (1H, s).

(11) Synthesis of Compound 15

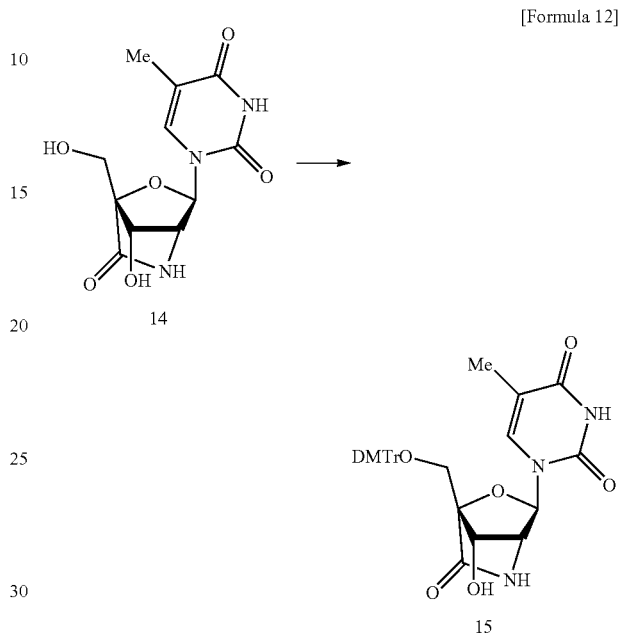

Under a nitrogen stream, 4,4'-dimethoxytrityl chloride (48.8 mg, 0.14 mmol) was added to 0.8 mL of an anhydrous pyridine solution of compound 14 (27.3 mg, 0.10 mmol) obtained in (10) above, and stirred for 3 hours. After saturated sodium bicarbonate water was added and stirred for several minutes and the solvent was distilled off, the solution was extracted with saturated sodium bicarbonate water/ethyl acetate, and the organic layer was recovered and dried over anhydrous sodium sulfate. After distilling off the solvent, the crude product was purified by flash column chromatography (n-hexane:ethyl acetate=10:1 (v/v)→ethyl acetate only), thus giving compound 15 (47.6 mg, yield 85%) as white foam.

The physical property data of the obtained compound 15 was as follows: melting point: 79-81° C.; IR (KBr): 3342, 3063, 2928, 1690, 1509, 1270, 1253, 1177, 1035 cm$^{-1}$; $^1$H-NMR (300 MHz, CDCl$_3$): δ1.66 (3H, s), 3.61, 3.92 (2H, AB, J=12.8 Hz), 3.78 (6H, s), 4.26 (1H, s), 4.46 (1H, s), 5.42 (1H, s), 6.86-7.45 (13H, m), 7.78 (1H, s); MS (FAB): m/z 586 (MH$^+$).

(12) Synthesis of Compound 16

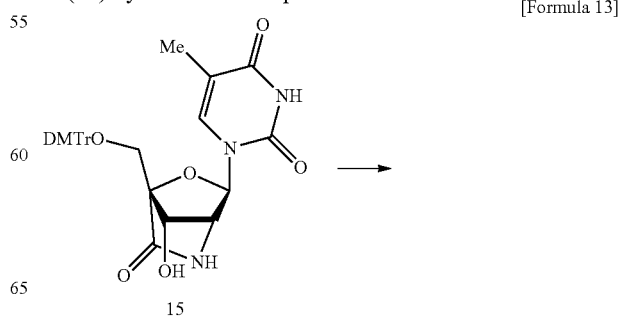

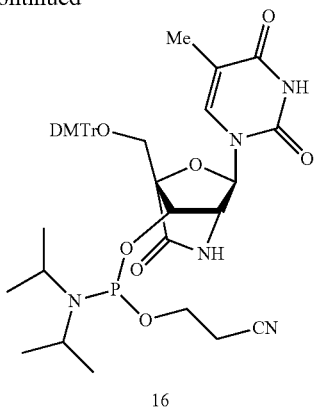

16

Under a nitrogen stream, N,N-diisopropylammoniumtetrazolide (22.2 mg, 0.13 mmol) and 2-cyanoethyl N,N,N',N'-tetraisopropylphosphorodiamidite (54.0 μL, 0.17 mmol) were added to 2.0 mL of an anhydrous acetonitrile-tetrahydrofuran solution (3:1 (v/v)) of compound 15 (100 mg, 0.17 mmol) obtained in (11) above, and stirred. After 1.5 hours, saturated sodium bicarbonate water was added and stirred for several minutes, then the solution was extracted with water/ethyl acetate, and the organic layer was recovered and dried over anhydrous sodium sulfate. After distilling off the solvent, the organic layer was purified by flash column chromatography (dichloromethane:methanol:triethylamine=50:1:1 (v/v/v)). The obtained crude product was dissolved in n-hexane and reprecipitated by addition of dichloromethane, thus giving compound 16 (29.4 mg, 22%) as white powder.

The physical property data of the obtained compound 16 was as follows: melting point: 110-112° C. ($CH_2Cl_2$); $^{31}P$-NMR (202.35 MHz, $CDCl_3$): δ149.74, 150.12; MS (FAB): m/z 786 ($MH^+$), high resolution MS (FAB): calculated $C_{41}H_{49}N_5O_9$ ($MH^+$): 786.3268. measured 786.3266.

Example 2

Selection of Target Region of Oligonucleotide

The base sequence (SEQ ID NO. 1: coding region, 2079 bases) of the human PCSK9 gene was obtained from GenBank (accession number: NM_174936). This base sequence was analyzed by computer software from the following 4 viewpoints, and the base sequence of a region that is suitable as a target of the oligonucleotide was selected.

(1) The folding of the mouse PCSK9 mRNA was calculated using mFold software (M. Zuker, Nucleic Acids Res., 2003, vol. 31, pp. 3406-3415). For the ease of oligonucleotide binding, a region where a stem loop structure is unlikely to be formed on the mRNA was selected.

(2) The base sequences of the human and mouse PCSK9 genes were compared using JustBio software (URL:http://www.justbio.com/). A region where the human and mouse base sequences are identical was selected such that application to a human is possible based on the evaluation results from the mouse.

(3) A region with a large GC content was selected such that a high level of thermal stability was attained when a double-strand nucleic acid was formed from the oligonucleotide and the target.

(4) Whether a base sequence that is similar to the base sequence of the target region was present or not in another region of the genome was determined using Blast software (S. F. Altschul et al., J. Mol. Biol., 1990, vol. 215, pp. 403-410). A region composed of a base sequence with low similarity to the base sequences of other regions of the genome was selected so as not to allow the oligonucleotide to bind to other mRNAs.

Target regions of the oligonucleotide most suitable in regard to the 4 conditions above were selected (SEQ ID NOS. 3 to 18), and oligonucleotides composed of complementary base sequences were designed (Tables 1-1 and 1-2). In Table 1-1, the term "PS backbone" refers to a structure in which the oxygen atom of the phosphate group in the phosphodiester linkage is replaced by a sulfur atom (the group corresponding to the phosphate group is referred to as a phosphorothioate group). Herein, an oligonucleotide in which all phosphate groups of an oligonucleotide are replaced by phosphorothioate groups is particularly referred to as an 5-oligonucleotide. The oligonucleotides in Table 1-1 are all S-oligonucleotides.

TABLE 1-1

| Oligonucleotide name | Base sequence of oligonucleotide | Target region in PCSK9 gene |
|---|---|---|
| PCSK9-0-S | 5'-gggctcatagcacattatcc-3' | 2606-2625 |
| PCSK9-0-BNA | 5'-GggCTCatagcaCaTTaTCc-3' | |
| PCSK9-1-S | 5'-ccaggcctatgagggtgccg-3' | 786-805(SEQ ID NO. 3) |
| PCSK9-1-BNA | 5'-CCaggCCTaTgagggTgCCg-3' | |
| PCSK9-1-BNA-3C | 5'-CCaggCCTaTgagggTgCCg-Ch-3' (Ch: cholesterol modified) | |
| PCSK9-1-NC | 5'-CCaggCCTaTgagggTgCCg-3' | |
| PCSK9-1-BNA-13 | 5'-CCtatgagggTGC-3' | 788-800(SEQ ID NO. 4) |
| PCSK9-2-S | 5'-gcatcccggccgctgaccac-3' | 697-716(SEQ ID NO. 5) |
| PCSK9-2-BNA | 5'-gCaTCCCggccgCTgaCCac-3' | |
| PCSK9-2-NC | 5'-gCaTCCCggccgCTgaCCac-3' | |

TABLE 1-1-continued

| Oligonucleotide name | Base sequence of oligonucleotide | Target region in PCSK9 gene |
|---|---|---|
| PCSK9-2-BNA-13 | 5'-CCggccgctgACC-3' | 699-711(SEQ ID NO. 6) |
| PCSK9-3-S | 5'-gctggggagtagaggcaggc-3' | 964-983(SEQ ID NO. 7) |
| PCSK9-3-BNA | 5'-gCTGgggagTAgAggCAgGc-3' | |
| PCSK9-3-BNA-13 | 5'-AGtagaggcaGGC-3' | 964-976(SEQ ID NO. 8) |
| PCSK9-4-S | 5'-gccacgtgggcagcagcctg-3' | 1159-1178(SEQ ID NO. 9) |
| PCSK9-4-BNA | 5'-gCCaCgTgggcagCAgCCTg-3' | |
| PCSK9-4-BNA(T, C) | 5'-gCCaCgTgggcagCagCCTg-3' | |
| PCSK9-4-NC(T, C) | 5'-gCCaCgTgggcagCagCCTg-3' | |
| PCSK9-4-i-BNA | 5'-gCCaCgtgggcagcagCCTg-3' | |
| PCSK9-4-ii-BNA | 5'-CgTgggcagCagCCTg-3' | 1159-1174 (SEQ ID NO. 10) |
| PCSK9-4-ii-BNA-A | 5'-CgTgggcagcagCCTg-3' | |
| PCSK9-4-ii-NC-A | 5'-CgTgggcagcagCCTg-3' | |
| PCSK9-4-ii-CON-A | 5'-CgTgggcagcagCCTg-3' | |
| PCSK9-4-iii-BNA | 5'-CgTgggcagCagCC-3' | 1161-1174(SEQ ID NO. 11) |
| PCSK9-4-iii-BNA-A | 5'-CgTgggcagcagCC-3' | |
| PCSK9-4-BNA-13 | 5'-ACgtgggcagCAG-3' | 1163-1175(SEQ ID NO. 12) |
| PCSK9-5-S | 5'-ggtcctcagggaaccaggcc-3' | 1278-1297(SEQ ID NO. 13) |
| PCSK9-5-BNA | 5'-ggTCCTCagggaaCCAggCc-3' | |
| PCSK9-5-BNA(T, C) | 5'-ggTCCTCagggaaCCAggCc-3' | |
| PCSK9-5-NC(T, C) | 5'-ggTCCTCagggaaCCAggCc-3' | |
| PCSK9-6-S | 5'-gccaccaggttgggggtcag-3' | 1306-1325(SEQ ID NO. 14) |
| PCSK9-6-BNA | 5'-gCCaCCaggTTgggggTCAg-3' | |
| PCSK9-6-BNA(T, C) | 5'-gCCaCCaggTTgggggTCag-3' | |
| PCSK9-6-NC(T, C) | 5'-gCCaCCaggTTgggggTCag-3' | |
| PCSK9-7-S | 5'-ctggagcagctcagcagctc-3' | 1444-1463(SEQ ID NO. 15) |
| PCSK9-7-BNA | 5'-CTgGagcagCTCagCagCTc-3' | |
| PCSK9-7-BNA(T, C) | 5'-CTggagcagCTCagCagCTc-3' | |
| PCSK9-7-NC(T, C) | 5'-CTggagcagCTCagCagCTc-3' | |
| PCSK9-8-S | 5'-tagacaccctcaccccaaa-3' | 1543-1562(SEQ ID NO. 16) |
| PCSK9-8-BNA | 5'-TagaCaCCCTcaccCCaAa-3' | |
| PCSK9-8-BNA(T, C) | 5'-TagaCaCCCTcaccCCaaa-3' | |
| PCSK9-8-NC(T, C) | 5'-TagaCaCCCTcaccCCaaa-3' | |
| PCSK9-9-S | 5'-cctggggcatggcagcagga-3' | 1795-1814(SEQ ID NO. 17) |
| PCSK9-9-BNA | 5'-CCTggggcaTggCAgCAgGa-3' | |
| PCSK9-10-S | 5'-gccggctccggcagcagatg-3' | 2028-2047(SEQ ID NO. 18) |
| PCSK9-10-BNA | 5'-gCCggCTCCggcagCagATg-3' | |

TABLE 1-1-continued

| Oligonucleotide name | Base sequence of oligonucleotide | Target region in PCSK9 gene |
|---|---|---|
| PCSK9-10-BNA(T, C) | 5'-gCCggCTCCggcagCagaTg-3' | |
| PCSK9-10-NC(T, C) | 5'-gCCggCTCCggcagCagaTg-3' | | all PS backbone, italicized upper-case character: NC, underlined upper-case character: CON, upper-case character: BNA, lower-case character: DNA

TABLE 1-2

| Oligonucleotide name | Base sequence of oligonucleotide | Target region in PCSK9 gene |
|---|---|---|
| PCSK9-4-ii-BNA-A2 | 5'-CgTgsgsgscsasgscsasgsCCTg-3' | 1159-1174 (SEQ ID NO. 10) |
| PCSK9-4-ii-NC-A2 | 5'-CgTgsgsgscsasgscsasgsCCTg-3' | | s: phosphorothioate group, italicized upper-case character: NC, upper-case character: BNA, lower-case character: DNA

Example 3

Synthesis and Purification of Oligonucleotide

BNA monomers (amidites) were synthesized by the methods described in Non Patent Literatures 3 to 7. NC monomers (amidites) were synthesized by the methods described in Non Patent Literatures 8 to 11. Using these and the CON monomer (amidite) synthesized in Example 1 as a monomer for DNA synthesis, 1 to 100 mg (in vivo grade) of oligonucleotides were synthesized as necessary by a DNA synthesizer, and subjected to HPLC purification and lyophilization treatment. The purity and structure of each obtained oligonucleotide were confirmed by HPLC and MALDI-TOF-MS.

As shown in Tables 1-1 and 1-2, the synthesized oligonucleotides (PCSK9 oligonucleotides) were 5-oligonucleotides not containing any sugar-modified nucleoside (DNA-oligonucleotides: PCSK9-1-S and the like), oligonucleotides containing a BNA-nucleoside (BNA-oligonucleotides: PCSK9-1-BNA and the like), oligonucleotides containing an NC-nucleoside (NC-oligonucleotides: PCSK9-1-NC and the like), and oligonucleotides containing a CON-nucleoside (CON-oligonucleotides: PCSK9-4-ii-CON-A and the like).

Example 4

Synthesis and Purification of Oligonucleotide in which Cholesterol is Bound to 3'-End According to a technique of introducing cholesterol as an amidite, oligonucleotide PCSK9-1-BNA-3C was synthesized in large quantities, thus giving 10 mg of an oligonucleotide.

Example 5

Evaluation of Nuclease Resistance of Oligonucleotide in Serum 1 nmol of an oligonucleotide was mixed with 10 μL FBS (fetal bovine serum), and sterilized water was added to the mixture so as to reach 20 μL. After this solution was incubated at 37° C. for a predetermined period of time, 13 μL of formamide was added such that the final formamide concentration was 40%, and the nucleases in FBS were deactivated. This sample was stored at −80° C. until HPLC analysis. For HPLC analysis, 400 μL of buffer A (25 mM Tris-HCl, 0.5% $CH_3CN$, pH 7.0) was added to this sample such that the final formamide concentration was 3%, and the mixture after being filtered twice with a 4 mm Millex®-HV Syringe Driven Filter Unit (pore size of 0.45 μm; manufactured by Millipore) was used as an HPLC analysis sample. The JASCO LC-2000 Plus series (manufactured by Jasco Corporation) was used for HPLC, and TSK-GEL (registered trademark) DNA-NPR (manufactured by Tosoh Corporation) was used as an HPLC column. Buffer A (25 mM Tris-HCl, 0.5% $CH_3CN$, pH 7.0) and buffer B (25 mM Tris-HCl, 0.5% $CH_3CN$, 1 M $NH_4Cl$, pH 7.0) were used. For the first 10 minutes, A was 100% and B was 0%, then for the next 45 minutes, the concentrations were changed from A being 100% and B being 0% to A being 50% and B being 50%, and for the next 10 minutes, A was 0% and B was 100%. The wavelength for detection by the above-described HPLC analysis was 260 nm. The HPLC peak area corresponding to the oligonucleotide was measured both before mixing with FBS and 120 minutes after mixing with FBS, and from the ratio of these areas, the percentage of oligonucleotide 120 minutes after mixing with FBS [% (120 min)] was obtained. Tables 2 and 3 show the results.

TABLE 2

| | n | | | | | | | | | | |
|---|---|---|---|---|---|---|---|---|---|---|---|
| | 0 | 1 | 2 | 3 | 4 | 5 | 6 | 7 | 8 | 9 | 10 |
| % (120 min.) of PCSK9-n-S | 12 | 27.6 | 45.9 | 37 | 47.9 | 44.5 | 25.2 | 29.3 | 42.6 | 36.6 | 34.9 |
| % (120 min.) of PCSK9-n-BNA | 65.2 | 65.9 | 46 | 48.6 | 55.3 | 60.1 | 70.5 | 60.7 | 61.6 | 64.8 | 54.8 |
| Ratio* | 5.43 | 2.39 | 1 | 1.31 | 1.15 | 1.35 | 2.8 | 2.07 | 1.45 | 1.77 | 1.57 |

*Ratio = [% (120 min.) of PCSK9-n-BNA]/[% (120 min.) of PCSK9-n-S]

TABLE 3

| | Oligonucleotide name | | | | | | | | | | | |
|---|---|---|---|---|---|---|---|---|---|---|---|---|
| | PCSK9-1-BNA | PCSK9-1-NC | PCSK9-1-BNA-3C | PCSK9-2-BNA | PCSK9-2-NC | PCSK9-4-BNA | PCSK9-4-BNA (T, C) | PCSK9-4-NC (T, C) | PCSK9-4-i-BNA | PCSK9-4-ii-BNA | PCSK9-4-ii-BNA-A | PCSK9-4-iii-BNA |
| % (120 min.) | 65.9 | 66 | 68.1 | 46 | 75.3 | 55.3 | 61.4 | 63.7 | 34.5 | 39.9 | 31.8 | 35.8 |

| | Oligonucleotide name | | | | | | | | | | |
|---|---|---|---|---|---|---|---|---|---|---|---|
| | PCSK9-4-iii-BNA-A | PCSK9-5-BNA | PCSK9-5-NC (T, C) | PCSK9-6-BNA | PCSK9-6-NC (T, C) | PCSK9-7-BNA | PCSK9-7-NC (T, C) | PCSK9-8-BNA | PCSK9-8-NC (T, C) | PCSK9-10-BNA | PCSK9-10-NC (T, C) |
| % (120 min.) | 29.9 | 60.1 | 63.7 | 70.5 | 70.7 | 60.7 | 66.2 | 61.6 | 87.9 | 54.8 | 59.7 |

As is clear from Tables 2 and 3, the percentages of the BNA-oligonucleotides 120 minutes after mixing with FBS [% (120 minutes)] were markedly higher than those of the DNA-oligonucleotides. Also, the percentages of the NC-oligonucleotides 120 minutes after mixing with FBS [% (120 minutes)] were higher than those of the BNA-oligonucleotides. Accordingly, it was found that the NC-oligonucleotides have the highest resistance to nucleases present in the serum. Moreover, it was found that regarding the BNA-oligonucleotides with the same length, the larger the number of BNA-nucleosides, the higher the nuclease resistance. Regarding the BNA-oligonucleotides with the same number of BNA-nucleosides, there was no correlation between the oligonucleotide length and the nuclease resistance. Accordingly, it was found that the number of BNA-nucleosides is more relevant to the nuclease resistance than the length of BNA-oligonucleotide.

Example 6

Evaluation of Structural Stability of Double-Strand Nucleic Acid Composed of Oligonucleotide and Target RNA Equimolar amounts of an oligonucleotide and a target RNA were mixed in a buffer (8.1 mM $Na_2HPO_4$, 2.68 mM KCl, 1.47 mM $KH_2PO_4$, pH 7.2), and heated at 95° C. for 5 minutes and then annealed to room temperature, thus forming a double-strand nucleic acid. The thermal stability of this double-strand nucleic acid was analyzed using a Peltier UV melting apparatus of a UV/Vis spectrophotometer DU800 (manufactured by Beckman). The temperature of the double-strand nucleic acid was increased from 20° C. to 95° C. at a rate of 0.5° C./min, and the change of the absorbance (A) at 260 nm caused by the increase in the temperature (T) was measured. The concentration of the double-strand nucleic acid was set at 1 μM, and the optical path length of the cell was set at 1 cm. A graph showing dA/dT vs T was drawn from the results of this measurement, and the temperature at which the value of dA/dT was largest, i.e., the temperature at which the change of A caused by T was largest, was regarded as the $T_m$ of the double-strand nucleic acid and used as an indicator of the thermal stability of the double-strand nucleic acid. Tables 4 and 5 show the results.

TABLE 4

| | n | | | | | | | | | | |
|---|---|---|---|---|---|---|---|---|---|---|---|
| | 0 | 1 | 2 | 3 | 4 | 5 | 6 | 7 | 8 | 9 | 10 |
| $T_m$ (° C.) of PCSK9-n-S | 37 | 49.6 | 57.5 | 47.2 | 51.8 | 50.4 | 51.3 | 47.2 | 54.6 | 50.4 | 53.9 |
| $T_m$ (° C.) of PCSK9-n-BNA | 72.1 | 83.2 | 94.1 | 83 | 94 | 84 | 85.5 | 78.6 | 85.6 | 81.2 | 87.7 |
| $T_m$ (° C.)* | 35.1 | 33.6 | 36.6 | 35.8 | 42.2 | 33.6 | 34.2 | 31.4 | 31 | 30.8 | 33.8 |

*$T_m$ (° C.) = [$T_m$ (° C.) of PCSK9-n-BNA] − [$T_m$ (° C.) of PCSK9-n-S]

TABLE 5

| | Oligonucleotide name | | | | | | | | | | | |
|---|---|---|---|---|---|---|---|---|---|---|---|---|
| | PCSK9-1-BNA | PCSK9-1-NC | PCSK9-1-BNA-3C | PCSK9-2-BNA | PCSK9-2-NC | PCSK9-4-BNA | PCSK9-4-BNA (T, C) | PCSK9-4-NC (T, C) | PCSK9-4-i-BNA | PCSK9-4-ii-BNA | PCSK9-4-ii-BNA-A | PCSK9-4-iii-BNA |
| $T_m$(° C.) | 83.2 | 86 | 84.9 | 94.1 | 94.4 | 94 | 87.6 | 88.6 | 74.7 | 71.9 | 65.1 | 64.3 |

| | Oligonucleotide name | | | | | | | | | | |
|---|---|---|---|---|---|---|---|---|---|---|---|
| | PCSK9-4-iii-BNA-A | PCSK9-5-BNA | PCSK9-5-NC (T, C) | PCSK9-6-BNA | PCSK9-6-NC (T, C) | PCSK9-7-BNA | PCSK9-7-NC (T, C) | PCSK9-8-BNA | PCSK9-8-NC (T, C) | PCSK9-10-BNA | PCSK9-10-NC (T, C) |
| $T_m$(° C.) | 54 | 84 | 83.3 | 85.5 | 87.7 | 78.6 | 77.1 | 85.6 | 90.1 | 87.7 | 94.2 |

As is clear from Tables 4 and 5, in many cases, the double-strand nucleic acids composed of BNA-oligonucleotides and target RNAs had $T_m$ at least 30° C. higher than the double-strand nucleic acids composed of DNA-oligonucleotides and target RNAs. Accordingly, it was found that the double-strand nucleic acids composed of BNA-oligonucleotides and target RNAs have a higher structural stability than the double-strand nucleic acids composed of DNA-oligonucleotides and target RNAs. Also, the double-strand nucleic acids composed of BNA-oligonucleotides and target RNAs and the double-strand nucleic acids composed of NC-oligonucleotides and target RNAs had nearly the same $T_m$. Accordingly, it was found that the double-strand nucleic acids composed of BNA-oligonucleotides and target RNAs and the double-strand nucleic acids composed of NC-oligonucleotides and target RNAs had nearly the same structural stability. Moreover, regarding the double-strand nucleic acids composed of target RNAs and BNA-oligonucleotides with the same length, the larger the number of BNA-nucleosides, the higher the $T_m$. Regarding the double-strand nucleic acids composed of target RNAs and BNA-oligonucleotides with the same number of BNA-nucleosides, the larger the oligonucleotide length, the higher the $T_m$. Accordingly, it was found that the number of BNA nucleosides and the length of BNA-oligonucleotide both contribute to the structural stability of the double-strand nucleic acids composed of BNA-oligonucleotides and target RNAs.

Example 7

Evaluation of RNase H Sensitivity of Double-Strand Nucleic Acid Composed of Oligonucleotide and Target RNA The 5'-end of the target RNA was labeled with $\gamma$-$^{32}$P. Specifically, 10 pmol of RNA and [$\gamma$-$^{32}$P]ATP equivalent to 10 pmol (manufactured by PerkinElmer) were reacted using a T4 polynucleotide kinase (manufactured by Toyobo Co., Ltd.). The product containing the [$\gamma$-$^{32}$P]-labeled RNA after the reaction was purified by a spin column to remove the unreacted [$\gamma$-$^{32}$P]ATP. 1 μL of 10 μM complementary-strand oligonucleotide was added to the purified [$\gamma$-$^{32}$P]-labeled RNA, and the mixture was heated at 95° C. for 5 minutes and then annealed to room temperature, thus forming a double-strand nucleic acid.

Next, 1 μL of the [$\gamma$-$^{32}$P]-labeled double-strand nucleic acid was mixed with 9 μL of a reaction buffer (40 mM Tris-HCl, 4 mM $MgCl_2$, 1 mM DTT, 4% glycerol, 0.003% BSA). 1 μL was collected from the mixture, and 9 μL of a stop solution (0.05 M EDTA, 80% formamide, BPB) was added to give an RNase H-untreated sample. 0.6 equivalents of RNase H (0.0006 units) was added to the remaining 9 μL of the reaction solution and incubated at 37° C. for 5 minutes. 1 μL was collected therefrom, and 9 μL of a stop solution was added to give an RNase H-untreated sample. These samples were stored at −20° C. until electrophoresis analysis. Electrophoresis of the samples was carried out at 300 V for 120 minutes using 20% denatured polyacrylamide gel containing 6 M urea. Electrophoresis was carried out at 4° C. for a double-strand nucleic acid composed of a DNA-oligonucleotide and a target RNA, at room temperature for a double-strand nucleic acid composed of a BNA-oligonucleotide and a target RNA, and at 60° C. for a double-strand nucleic acid composed of an NC-oligonucleotide and a target RNA. The gel after electrophoresis was exposed to an imaging plate and then analyzed by an image analyzer. FIGS. 1 to 5 show the results.

As is clear from FIGS. 1 to 5, it was found that in any case the molecular weight of the [$\gamma$-$^{32}$P]-labeled RNA was decreased by addition of RNase H, and thus the [$\gamma$-$^{32}$P]-labeled RNA was decomposed by RNase H occurred. Accordingly, it was found that all double-strand nucleic acids were sensitive to RNase H.

Example 8

In Vitro Expression Inhibitory Effect on PCSK9 Gene by Oligonucleotide 1

Mouse liver cell strain NMuli cells prepared so as to have $4.0 \times 10^5$ cells/mL were seeded onto a 6-well plate in an amount of 2 mL per well, and cultured at 37° C. under 5% $CO_2$ for 24 hours. In order to achieve a final concentration of 1, 3, 10, 30, or 50 nM, 14.3 μL of Lipofectamine 2000 (manufactured by Invitrogen), 2.2 μL of a 1 μM oligonucleotide-containing solution for a final concentration of 1 nM, 6.6 μL for 3 nM, 22 μL for 10 nM, 66 μL for 30 nM, or 110 μL for 50 nM; and 533.5 μL of Opti-MEM (manufactured by Invitrogen) in the case of having a final concentration of 1 nM, 529.1 μL for 3 nM, 513.7 μL for 10 nM, 469.7 μL for 30 nM, or 425.7 μL for 50 nM were mixed. The mixed solution was incubated at room temperature for 20 minutes, and then 500 μL of the mixed solution and 1500 μL of Opti-MEM were added to each well. The culture medium was replaced 4 hours after oligonucleotide addition. Cells were collected after an additional 20 hours and disrupted by ISOGEN (manufactured by Nippon Gene Co., Ltd.), and total RNA was extracted from the collected cells. The concentration of the extracted total RNA was quantified by a spectrophotometer, and the RNA length was analyzed by agarose gel electrophoresis.

1 μL of 0.5 μg/μL oligo dT (5'-TTTTTTTTTTTTTTTTTT-3') and 1 μL of 10 mM dNTP were added to the total RNA prepared so as to have 4 μg/10 μL. The mixture was incubated at 65° C. for 5 minutes, and then rapidly cooled on ice. 1 μL of 40 U/μL RNase OUT (registered trademark) (manufactured by Invitrogen), 4 μL of 5×First Strand Buffer (manufactured by Invitrogen), and 2 μL of 0.1 M DTT (Wako Pure Chemical Industries, Ltd.) were added to the mixture, and the mixture was incubated at 42° C. for 2 minutes. 1 μL of SuperScript II Solution (a solution in which 2 μL of 200 U/μL SuperScript II (manufactured by Invitrogen) and 6 μL of distilled water were mixed) was further added to the mixture, and the mixture was incubated at 42° C. for 50 minutes to carry out a reverse transcription reaction. After the reaction, the mixture was incubated at 70° C. for 15 minutes to deactivate SuperScript II. 1 μL of 2 U/μL of RNase H (manufactured by Invitrogen) was added to the mixture, and the mixture was incubated at 37° C. for 20 minutes to give cDNA. Using the obtained cDNA, Fast SYBR (registered trademark) Green Master Mix (manufactured by Applied Biosystems) and SYBR (registered trademark) Green Realtime PCR Master Mix (Toyobo Co., Ltd.), real-time PCR was carried out by a Mini Opticon (registered trademark) real-time PCR analysis system (Bio-Rad Laboratories, Inc.) to quantify the PCSK9 mRNA level. In the real-time PCR, the GAPDH mRNA level of the housekeeping gene was also quantified at the same time, and the PCSK9 mRNA level relative to the GAPDH mRNA level was evaluated.

The oligonucleotides and the primers used are as follows:

```
PCSK9-0-BNA
PCSK9 Fw primer 0:
5'-TCAGTTCTGCACACCTCCAG-3' (SEQ ID NO. 19)

PCSK9 Rv primer 0:
5'-GGGTAAGGTGCGGTAAGTCC-3' (SEQ ID NO. 20)

PCSK9-1-BNA, PCSK9-2-BNA, PCSK9-1-NC,
PCSK9-2-NC, PCSK9-1-BNA-3C
PCSK9 Fw primer 1:
5'-CACGCTTCCACAGACAGGCG-3' (SEQ ID NO. 21)

PCSK9 Rv primer 1:
5'-CGTTGAGGATGCGGCTATAC-3' (SEQ ID NO. 22)

PCSK9-3-BNA
PCSK9 Fw primer 2:
5'-GCCGGCACCTGGCGAGGACT-3' (SEQ ID NO. 23)

PCSK9 Rv primer 2:
5'-CCACTCTGTGACATGAAGCA-3' (SEQ ID NO. 24)

PCSK9-4-BNA, PCSK9-4-BNA(T, C),
PCSK9-5-BNA, PCSK9-6-BNA, PCSK9-4-NC(T, C),
PCSK9-5-NC(T, C), PCSK9-6-NC(T, C),
PCSK9-4-i-BNA, PCSK9-4-ii-BNA,
PCSK9-4-ii-BNA-A, PCSK9-4-iii-BNA,
PCSK9-4-iii-BNA-A
```

```
GAPDH Rv primer:
5'-GACAAGCTTCCCATTCTCGG-3' (SEQ ID NO. 34)
```

Figure 6B:
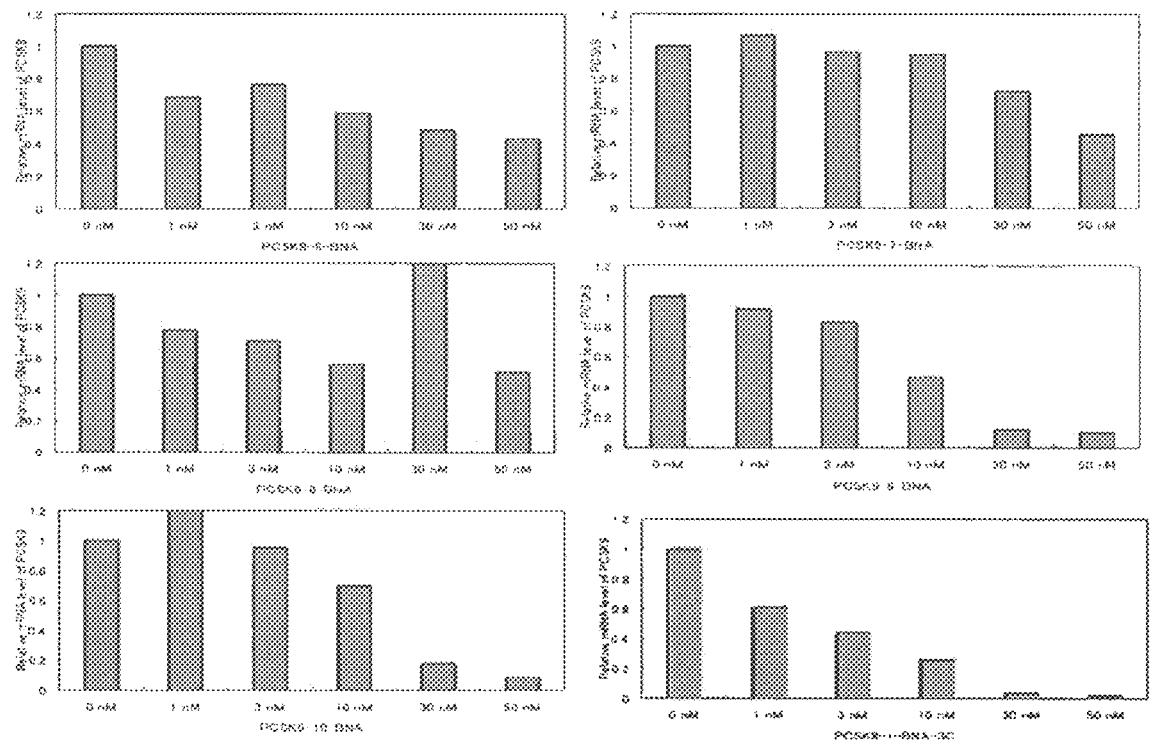
FIG. 6B includes graphs showing the PCSK9 mRNA expression levels of NMuLi cells treated with BNA-oligonucleotide.
Figure 6C:
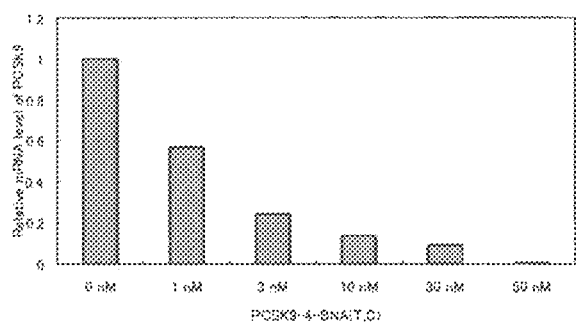
FIG. 6C is a graph showing the PCSK9 mRNA expression levels of NMuLi cells treated with BNA-oligonucleotide.
Figure 7:
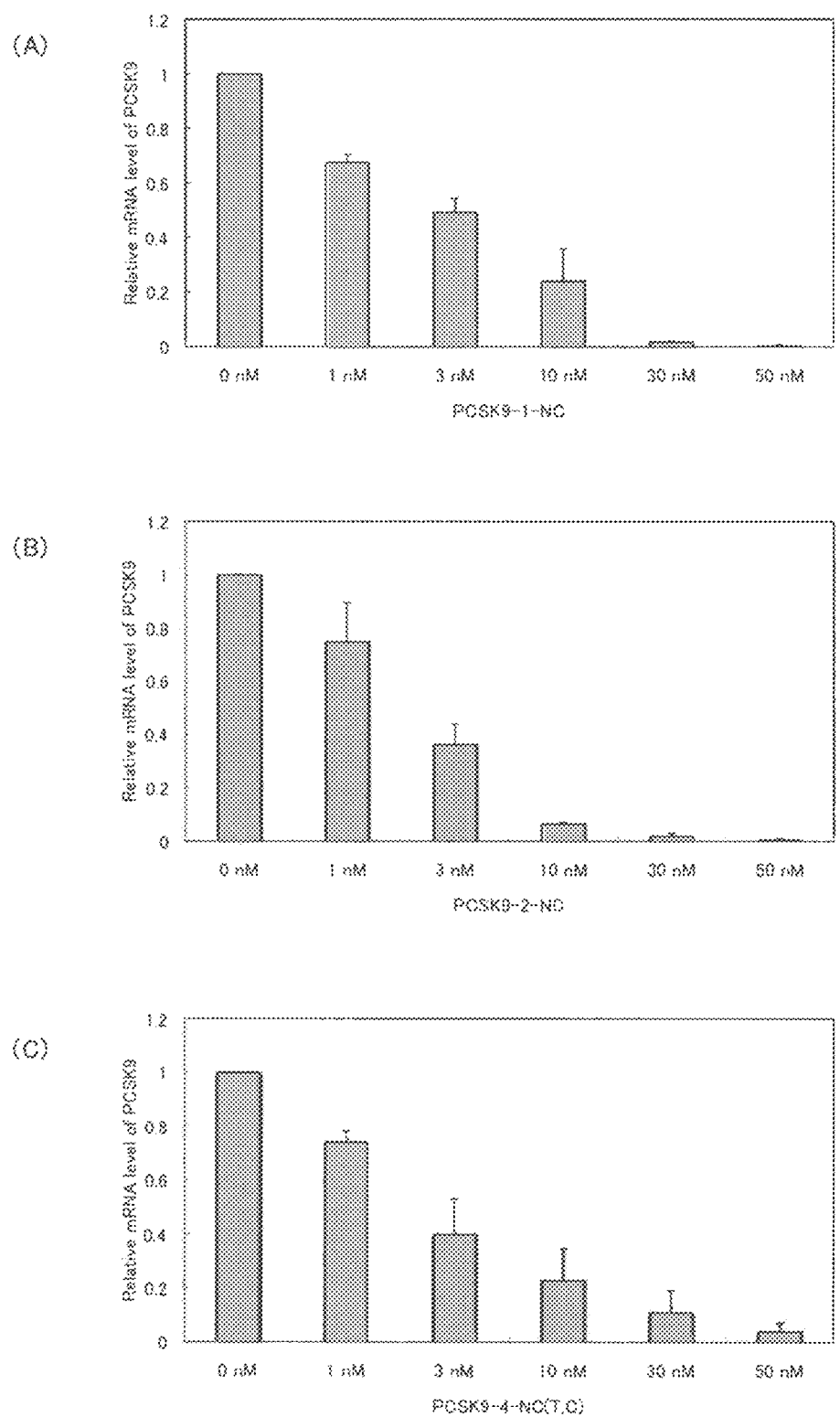
FIG. 7 includes graphs showing the PCSK9 mRNA expression levels of NMuLi cells treated with NC-oligonucleotide.
Figure 8:
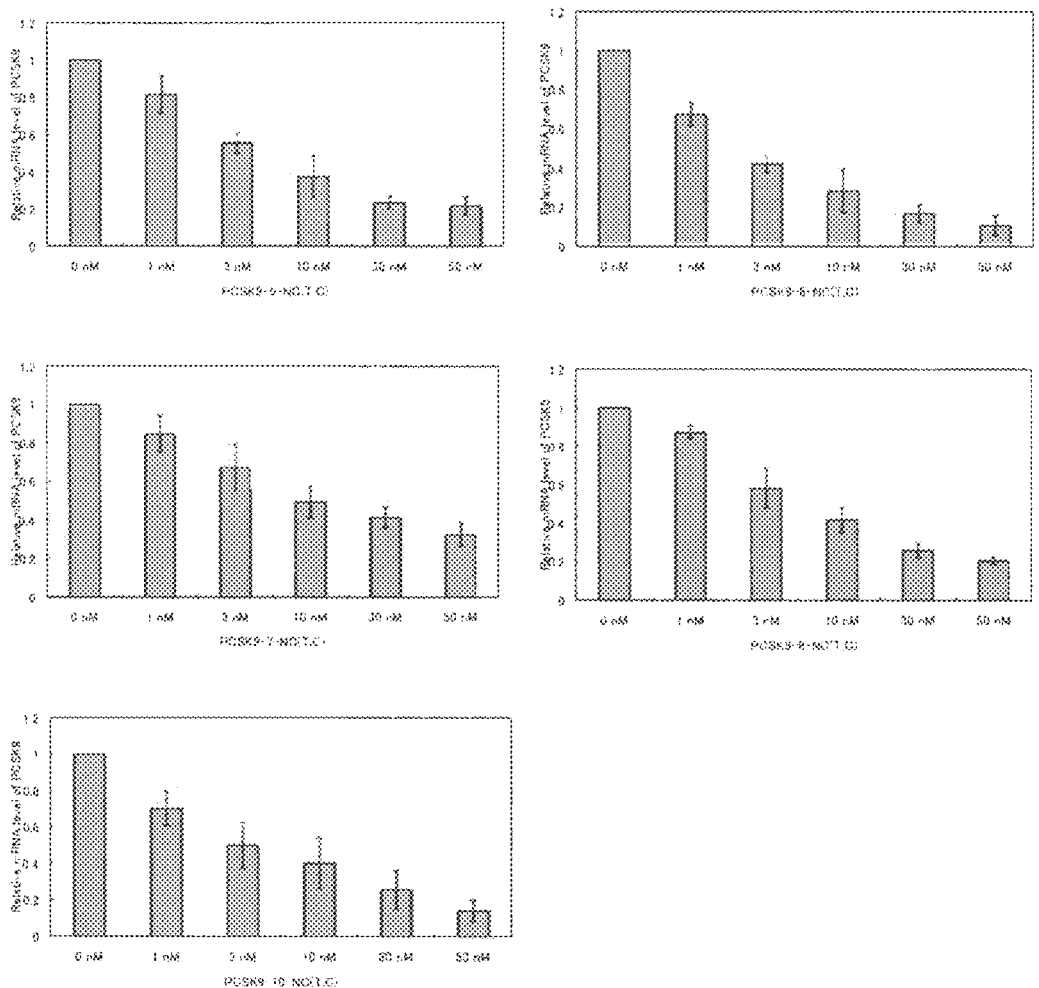
FIG. 8 includes graphs showing the PCSK9 mRNA expression levels of NMuLi cells treated with NC-oligonucleotide.

FIGS. 6 to 8 show the results of the PCSK9 mRNA expression levels obtained in the NMuli cells treated with the respective oligonucleotides. FIG. 6 shows the results in the case of BNA-oligonucleotide treatment (FIG. 6A: PCSK9-O-BNA, PCSK9-1-BNA, PCSK9-2-BNA, PCSK9-3-BNA, PCSK9-4-BNA, PCSK9-5-BNA; FIG. 6B: PCSK 9-6-BNA, PCSK9-7-BNA, PCSK9-8-BNA, PCSK9-9-BNA, PCSK9-10-BNA, PCSK9-1-BNA-3C; and FIG. 6C: PCSK9-4-BNA (T, C)), and FIGS. 7 and 8 show the results in the case of NC-oligonucleotide treatment (FIG. 7: PCSK9-1-NC, PCSK9-2-NC, and PCSK9-4-NC (T, C); FIG. 8: PCSK9-5-NC (T, C), PCSK9-6-NC (T, C), PCSK9-7-NC (T, C), PCSK9-8-NC (T, C), and PCSK9-10-NC (T, C)). As is clear from FIGS. 6 to 8, in the many cases of the oligonucleotide treatment, the PCSK9 mRNA expression levels were lowered in an oligonucleotide concentration-dependent manner.

Table 6 shows the results of the PCSK9 mRNA expression levels attained when treated with 50 nM PCSK9-4-BNA, PCSK9-4-1-BNA, PCSK9-4-ii-BNA, PCSK9-4-ii-BNA-A, PCSK9-4-iii-BNA, or PCSK9-4-iii-BNA-A relative to the PCSK9 mRNA expression level attained when not treated with an oligonucleotide being 1.

TABLE 6

| | Oligonucleotide name | | | | | |
|---|---|---|---|---|---|---|
| | PCSK9-4-BNA | PCSK9-4-i-BNA | PCSK9-4-ii-BNA | PCSK9-4-ii-BNA-A | PCSK9-4-iii-BNA | PCSK9-4-iii-BNA-A |
| Relative mRNA level | 0.259 ± 0.036 | 0.205 ± 0.043 | 0.189 ± 0.015 | 0.309 ± 0.046 | 0.290 ± 0.019 | 0.194 ± 0.076 |

```
-continued
PCSK9 Fw primer 3:
5'-GTGACTGCAGCACATGCTTC-3' (SEQ ID NO. 25)

PCSK9 Rv primer 3:
5'-CGTCCTACAGAGCAGCTGCC-3' (SEQ ID NO. 26)

PCSK9-7-BNA, PCSK9-8-BNA,
PCSK9-7-NC(T, C), PCSK9-8-NC(T, C),
PCSK9 Fw primer 4:
5'-GCTCTGTAGGACGGTGTGGT-3' (SEQ ID NO. 27)

PCSK9 Rv primer 4:
5'-GGTGTTGTGGATGCTGCAGT-3' (SEQ ID NO. 28)

PCSK9-9-BNA
PCSK9 Fw primer 5:
5'-CCAGAAGGACCATGTTCTCA-3' (SEQ ID NO. 29)

PCSK9 Rv primer 5:
5'-GCACATTGCATCCAGTCAGG-3' (SEQ ID NO. 30)

PCSK9-10-BNA, PCSK9-10-NC(T, C)
PCSK9 Fw primer 6:
5'-GGATCTCAGGTCCTTCAGAG-3' (SEQ ID NO. 31)

PCSK9 Rv primer 6:
5'-GCCTGAGGCTGTCACTGAAC-3' (SEQ ID NO. 32)
```

For quantification of GAPDH

```
GAPDH Fw primer:
5'-GTGTGAACGGATTTGGCCGT-3' (SEQ ID NO. 33)
```

As is clear from Table 6, PCSK9-4-1-BNA and, among the shorter sequences, PCSK9-4-ii-BNA and PCSK9-4-iii-BNA-A demonstrated a superior PCSK9 gene expression inhibitory effect.

Example 9

In Vitro Expression Inhibitory Effect on PCSK9 Gene by Oligonucleotide 2

The in vitro expression inhibitory effect on the PCSK9 gene by an oligonucleotide was investigated in the same manner as in Example 8 except that human hepatoma-derived cell strain Huh-7 was used in place of NMuli.

The oligonucleotides and the primers used are as follows:

```
PCSK9-1-BNA, PCSK9-1-BNA-13,
PCSK9-2-BNA-13
PCSK9 Fw primer 1:
5'-CACGCTTCCACAGACAGGCG-3' (SEQ ID NO. 21)

PCSK9 Rv primer 1:
5'-CGTTGAGGATGCGGCTATAC-3' (SEQ ID NO. 22)

PCSK9-3-BNA-13
PCSK9 Fw primer 2:
5'-GCCGGCACCTGGCGAGGACT-3' (SEQ ID NO. 23)

PCSK9 Rv primer 2:
5'-CCACTCTGTGACATGAAGCA-3' (SEQ ID NO. 24)
```

```
PCSK9-4-BNA-13
PCSK9 Fw primer 3:
5'-GTGACTGCAGCACATGCTTC-3'    (SEQ ID NO. 25)

PCSK9 Rv primer 3:
5'-CGTCCTACAGAGCAGCTGCC-3'    (SEQ ID NO. 26)
```

Figure 9:
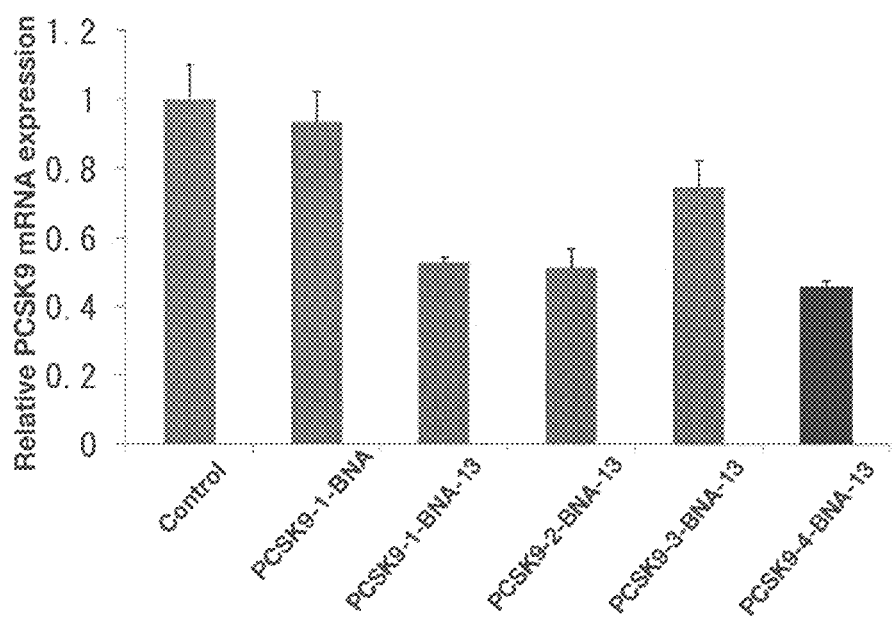
FIG. 9 is a graph showing the PCSK9 mRNA expression levels of Huh-7 cells treated with BNA-oligonucleotide (13 bases).

FIG. 9 shows the results obtained when 50 nM oligonucleotides were used. As is clear from FIG. 9, it was found that short oligonucleotides (13 bases) such as PCSK9-4-BNA-13 all have a greater PCSK9 gene expression inhibitory effect than PCSK9-1-BNA (20 bases).

Example 10

In Vivo Oligonucleotide Administration Experiment 1

Five 6-week old C57BL6/J mice (male: CLEA Japan) were provided as test animals for each administration group. After 2 weeks of a high-fat load diet (F2HFD1, manufactured by Oriental Yeast Co., Ltd.), the blood was collected on day 0, and a BNA-oligonucleotide or NC-oligonucleotide was intraperitoneally administered (10 mg/kg/time). Administration was carried out twice per week for 2 weeks to 6 weeks, during which the blood was collected several times from the caudal vein. 3 weeks or 6 weeks later, the blood was collected from the caudal vein in a fasting state. Next, the mice were anesthetized with diethyl ether and then subjected to perfusion with PBS from the superior mesenteric vein, and the liver was collected, washed with PBS, cut into small pieces, flash-frozen with liquid nitrogen, and then stored at −80° C.

(Extraction and Quantification of mRNA from Liver: Real-Time PCR)

The frozen liver sections were homogenized in 1 mL of TRIzol Regent (manufactured by Invitrogen), and 200 μL of chloroform was added thereto. Then, the sections were centrifuged at 13,200 rpm at 4° C. for 15 minutes. 220 μL of supernatant was added to 400 μL of isopropanol, mixed by inversion, and centrifuged at 13,200 rpm at 4° C. for 15 minutes, and then isopropanol was removed. Next, 800 μL of 75% ethanol was added, and then the mixture was centrifuged at 13,200 rpm at 4° C. for 5 minutes. The precipitate containing total RNA was dissolved in 80 μL of RNA-free water (Water, DEPC treated, RNase tested; Nacalai Tesque, Inc.). The extracted total RNA was quantified by a spectrophotometer, and the length of the RNA was confirmed by agarose gel electrophoresis.

cDNA was prepared from 10 μg of the total RNA using a High Capacity cDNA Reverse Transcription Kit (manufactured by Applied Biosystems). Using the obtained cDNA and Fast SYBR (registered trademark) Green Master Mix (manufactured by Applied Biosystems), real-time PCR was carried out, and the PCSK9 mRNA level was quantified. In the real-time PCR, the GAPDH mRNA level of the housekeeping gene was also quantified at the same time, and the PCSK9 mRNA level relative to the GAPDH mRNA level was evaluated.

The oligonucleotides and the primers used are as follows:

```
PCSK9-1-BNA, PCSK9-1-NC
PCSK9 Fw primer 7:
5'-GCTCAACTGTCAAGGGAAGG-3'    (SEQ ID NO. 35)

PCSK9 Rv primer 1:
5'-CGTTGAGGATGCGGCTATAC-3'    (SEQ ID NO. 22)

PCSK9-2-BNA, PCSK9-2-NC
PCSK9 Fw primer 1:
5'-CACGCTTCCACAGACAGGCG-3'    (SEQ ID NO. 21)

PCSK9 Rv primer 1:
5'-CGTTGAGGATGCGGCTATAC-3'    (SEQ ID NO. 22)

PCSK9-4-BNA, PCSK9-4-BNA(T, C),
PCSK9-4-NC(T, C)
PCSK9 Fw primer 3:
5'-GTGACTGCAGCACATGCTTC-3'    (SEQ ID NO. 25)

PCSK9 Rv primer 3:
5'-CGTCCTACAGAGCAGCTGCC-3'    (SEQ ID NO. 26)
```

For quantification of GAPDH

```
GAPDH Fw primer:
5'-GTGTGAACGGATTTGGCCGT-3'    (SEQ ID NO. 33)

GAPDH Rv primer:
5'-GACAAGCTTCCCATTCTCGG-3'    (SEQ ID NO. 34)
```

Figure 10:
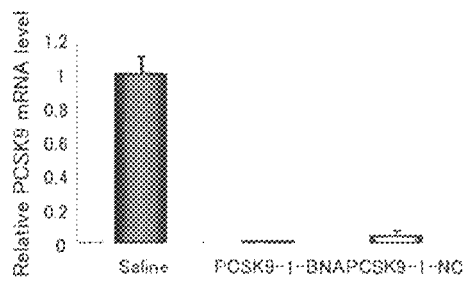
FIG. 10 is a graph showing the PCSK9 mRNA expression levels in the liver after 6-week mouse intraperitoneal administration of PCSK9-1-BNA or PCSK9-1-NC.
Figure 11:
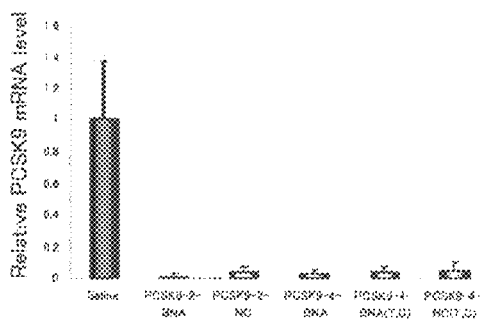
FIG. 11 is a graph showing the PCSK9 mRNA expression levels in the liver after 3-week mouse intraperitoneal administration of PCSK9 oligonucleotide.

FIGS. 10 and 11 show the results of determining the PCSK9 mRNA expression level in the liver obtained by mouse intraperitoneal administration of each oligonucleotide (FIG. 10: PCSK9-1-BNA, PCSK9-1-NC; FIG. 11: PCSK9-2-BNA, PCSK9-2-NC, PCSK9-4-BNA, PCSK9-4-BNA (T, C), PCSK9-4-NC (T, C)). As is clear from FIGS. 10 and 11, the PCSK9 mRNA expression levels in all oligonucleotide-administered groups were lowered to no greater than 5% of that of the saline-administered group.

(Quantification of Serum Total Cholesterol Level and Lipoprotein Fraction Cholesterol Level)

The blood was collected from the mouse caudal vein, left to stand still for 20 minutes at room temperature, and then centrifuged at 5000 rpm at 4° C. for 20 minutes to separate the serum. The serum total cholesterol level of each serum sample was quantified using Cholesterol E-Test Wako (manufactured by Wako Pure Chemical Industries, Ltd.). 1.5 mL of a color-producing reagent was added to 10 μL of the serum, the mixture was warmed at 37° C. for 5 minutes, and the absorbance at 600 nm was measured using a spectrophotometer. A value was calculated using the calibration curve of a standard reagent.

Figure 12:
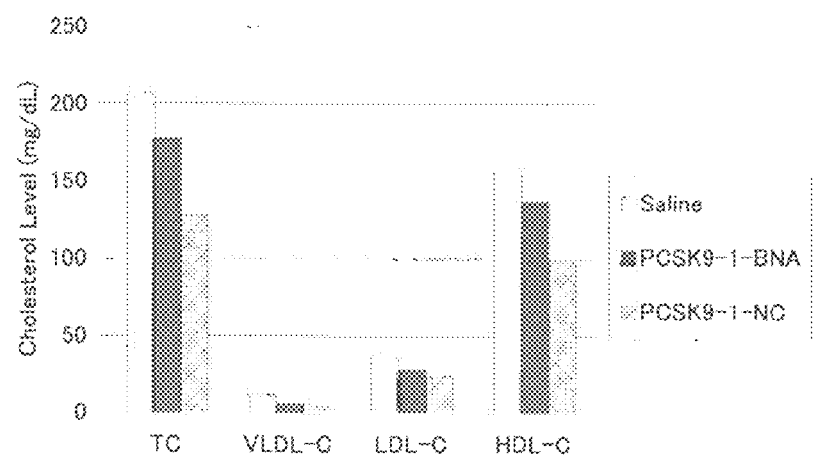
FIG. 12 is a graph showing the serum total cholesterol levels and the cholesterol levels in the lipoprotein fraction after 6-week mouse intraperitoneal administration of PCS9-1-BNA or PCS9-1-NC.

For lipoprotein analysis, at Skylight Biotech Inc., lipoprotein was fractionated into 3 fractions (VLDL: very low density lipoprotein, LDL: low density lipoprotein, and HDL: high density lipoprotein) according to the molecular weight by gel filtration using HPLC, and the cholesterol level of each fraction was quantified using Cholesterol E-Test Wako. FIG. 12 shows the results.

As is clear from the FIG. 12, the serum total cholesterol level (TC), cholesterol level in the VLDL fraction (VLDL-C), cholesterol level in the LDL fraction (LDL-C), and cholesterol level in the HDL fraction (HDL-C) of all PCSK9-1-BNA and PCSK9-1-NC oligonucleotide-administered groups were lower than that of the saline-administered group.

(Quantification of LDL Receptor Protein: Western Blotting)

The frozen liver sections (50 mg) were added to 500 μL of a RIPA buffer for homogenization and subjected to refrigerated centrifugation at 10,000 rpm for 3 minutes, and the supernatant was subjected to protein quantification using Bio-Rad DC (manufactured by Bio-Rad Laboratories, Inc.). 7 μg of protein was applied to the respective lanes on polyacrylamide gel ReadyGel J (4%) (manufactured by Bio-Rad Laboratories, Inc.), and electrophoresis was carried out at 200

Figure 13:
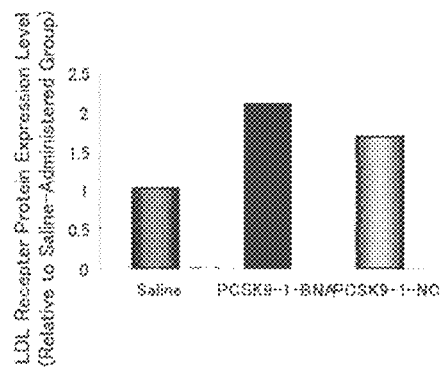
FIG. 13 is a graph showing the LDL receptor protein expression levels in the liver after 6-week mouse intraperitoneal administration of PCSK9-1-BNA or PCSK9-1-NC.

V for 40 minutes. Blotting was carried out at 180 mA for 90 minutes using Immun-Blot (registered trademark) PVDF Membrane (manufactured by Bio-Rad Laboratories, Inc.), and then blocking was carried out for 1 hour using Blocking One (Nacalai Tesque, Inc.). The obtained membrane was reacted with a goat anti-LDL receptor polyclonal antibody (LDLR M-20, Santa Cruz Biotechnology Inc.) as a primary antibody, and reacted with an anti-goat polyclonal antibody (Donkey anti goat IgG HRP, Santa Cruz Biotechnology Inc.) as a secondary antibody. Next, the membrane was allowed to develop a color using ECL plus (Western Blotting Detection System, GE Healthcare), and the level of color development was quantified. FIG. 13 shows the results.

As is clear from FIG. 13, the LDL receptor protein expression levels of all PCSK9-1-BNA and PCSK9-1-NC oligonucleotide-administered groups were increased 1.7 to 2 fold relative to that of the saline-administered group.

(Histopathological Observation of Liver Tissue)

Figure 14:
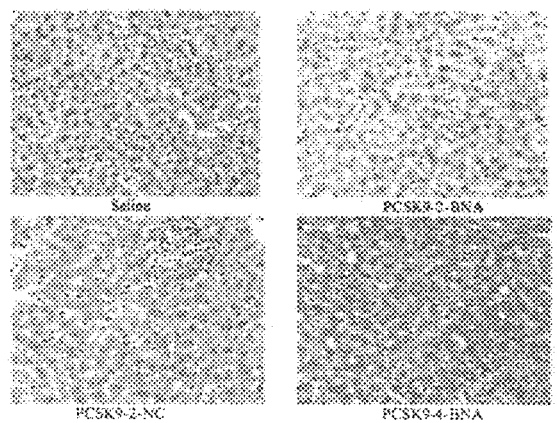
FIG. 14 shows pathological images (HE staining, 40-fold magnification) of the liver after 3-week mouse intraperitoneal administration of PCSK9-2-BNA, PCSK9-2-NC, or PCSK9-4-BNA.

An experiment of administering an oligonucleotide into a mouse was carried out in the same manner as above except that PCSK9-2-BNA, PCSK9-2-NC, or PCSK9-4-BNA was used as an oligonucleotide and intraperitoneally administered 6 times in 3 weeks (20 mg/kg/time). In the same manner as above, the liver tissue was collected, fixed by being immersed in a 10% formalin buffer for 24 hours, then washed with running water for 6 hours, and paraffin-embedded. A thin section (5 μm) was prepared, hematoxylin-stained, observed under a microscope, and photographed. FIG. 14 shows the results (40-fold magnification).

As is clear from FIG. 14, none of the oligonucleotide-administered groups showed hepatotoxicity compared with the saline-administered group.

(Toxicity Evaluation)

Figure 15:
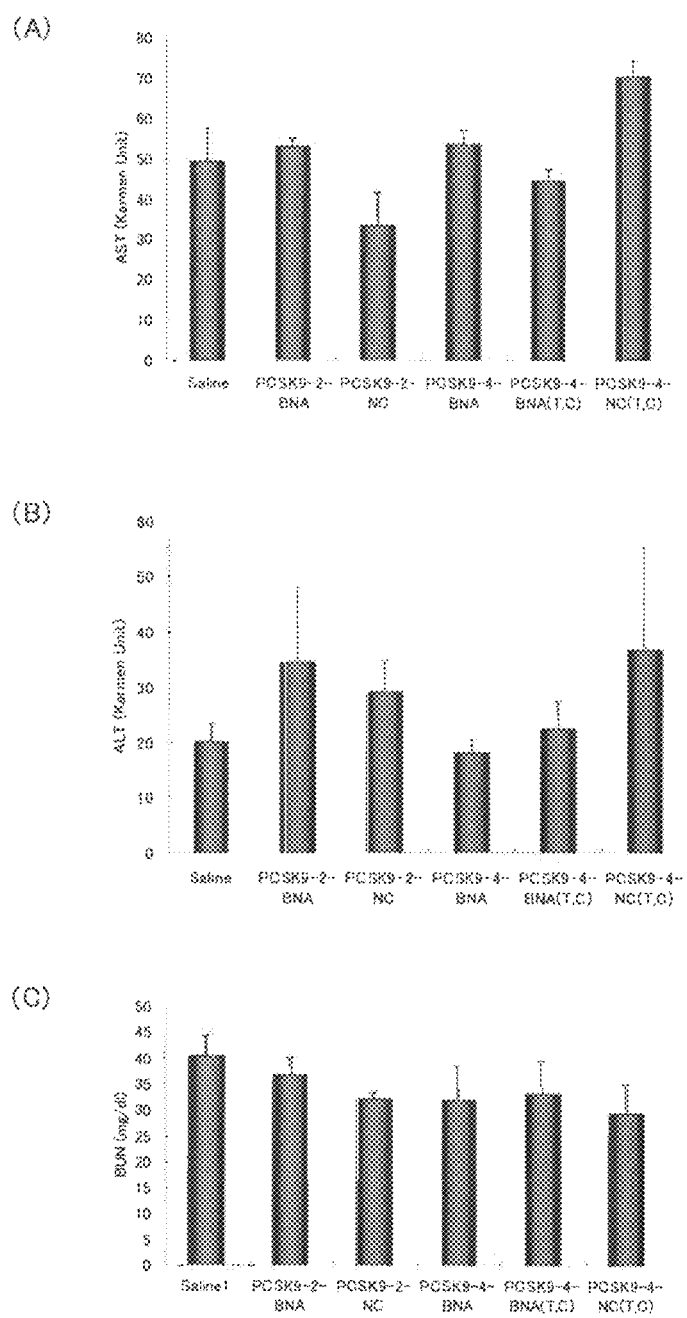
FIG. 15 includes graphs showing serum AST levels (A), serum ALT levels (B), and serum BUN levels (C) after 2-week mouse intraperitoneal administration of PCSK9 oligonucleotide.

Using the mouse serum after administration of an oligonucleotide (PCSK9-2-BNA, PCSK9-2-NC, PCSK9-4-BNA, PCSK9-4-BNA (T, C), or PCSK9-4-NC (T, C)), the AST level, the ALT level, and the BUN level were quantified. The AST level and the ALT level were quantified using Transaminase CII-Test Wako (manufactured by Wako Pure Chemical Industries, Ltd.). 250 μL of a substrate enzyme liquid for AST level measurement or ALT level measurement was added to 10 μL of the serum, and the mixture was warmed at 37° C. for 5 minutes. 250 μL of a color-producing reagent was added, and the mixture was warmed at 37° C. for 20 minutes. Next, after adding 1 mL of a reaction stop solution, the absorbance at 555 nm was measured using a spectrophotometer. The respective levels were calculated using the calibration curve of a standard reagent. For the BUN level, 1 mL of a color-producing reagent A was added to 10 μL of the serum, the mixture was warmed at 37° C. for 15 minutes, 1 mL of a color-producing reagent B was added, the mixture was warmed at 37° C. for 10 minutes, and the absorbance at 570 nm was measured using a spectrophotometer. The levels were calculated using the calibration curve of a standard reagent. FIG. 15 shows the results (A: AST level, B: ALT level, C: BUN level).

As is clear from FIG. 15, none of the oligonucleotide-administered groups showed a significant change in AST level or ALT level compared with the saline-administered group, thus not showing hepatotoxicity.

Example 11

In Vivo Oligonucleotide Administration Experiment 2

Figure 16:
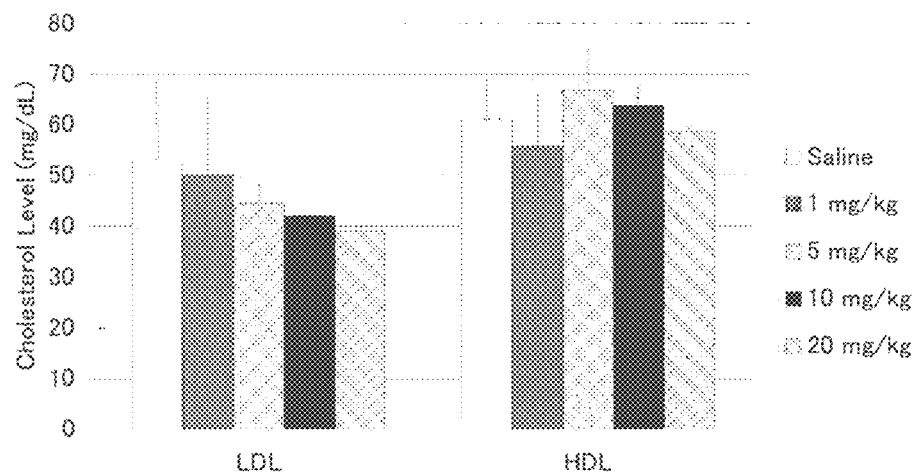
FIG. 16 is a graph showing serum cholesterol levels (according to the fraction) after 6-week mouse intraperitoneal administration of PCSK9-1-BNA.

Five 6-week old C57BL6/J mice (male: CLEA Japan) were provided as test animals for each administration group. After 2 weeks of a high-fat load diet (F2HFD1, Oriental Yeast Co., Ltd.), the blood was collected on day 0, and an oligonucleotide (PCSK9-1-BNA) was intraperitoneally administered. The dosage was 0, 1, 5, 10, or 20 mg/kg. Administration was carried out twice per week for 6 weeks, and 6 weeks later, the blood was collected from the caudal vein in a fasting state. The serum total cholesterol level and the lipoprotein fraction cholesterol level were quantified in the same manner as in Example 10. FIG. 16 shows the results of determining the cholesterol levels in the LDL fractions and the cholesterol levels in the HDL fractions ("LDL" indicates the cholesterol levels in the LDL fractions, and "HDL" indicates the cholesterol levels in the HDL fractions).

As is clear from FIG. 16, although the HDL-C of the oligonucleotide PCSK9-1-BNA-administered groups was not different from that of the saline-administered group, the LDL-C was reduced in a dose-dependent manner.

Example 12

In Vivo Oligonucleotide Administration Experiment 3

Figure 17:
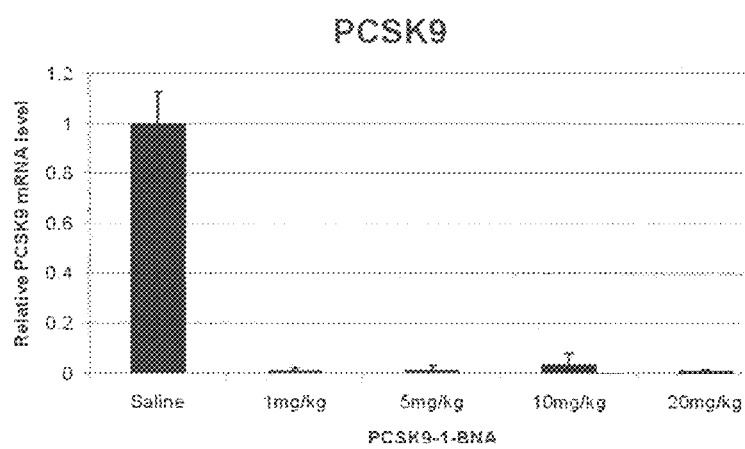
FIG. 17 is a graph showing the PCSK9 mRNA expression levels in the liver after 6-week mouse intraperitoneal administration of PCSK9-1-BNA.

Five 6-week old C57BL6/J mice (male: CLEA Japan) were provided as test animals for each administration group. After 2 weeks of a high-fat load diet (F2HFD1, Oriental Yeast Co., Ltd.), the blood was collected on day 0, and PCSK9-1-BNA was intraperitoneally administered. The dosage was 0, 1, 5, 10, or 20 mg/kg. Administration was carried out twice per week for 6 weeks, and 6 weeks later, the blood was collected from the caudal vein in a fasting state. Next, the mice were anesthetized with diethyl ether and then subjected to perfusion with PBS from the heart, and the liver was collected, washed with PBS, cut into small pieces, flash-frozen with liquid nitrogen, and then stored at −80° C. The PCSK9 mRNA level was quantified in the same manner as in Example 10. FIG. 17 shows the results.

As is clear from FIG. 17, the PCSK9 mRNA expression in the liver of the oligonucleotide PCSK9-1-BNA-administered groups was nearly completely suppressed (>97%) with the respective dosages compared with the saline-administered group.

Example 13

In Vivo Oligonucleotide Administration Experiment 4

Using the mouse serum after administration of PCSK9-1-BNA of Example 12, the AST level, the ALT level, and the BUN level were quantified in the same manner as in Example 10. FIG. 18 shows the results (A: AST level, B: ALT level, C: BUN level).

As is clear from FIG. 18, the PCSK9 mRNA expression levels in the liver in all oligonucleotide-administered groups were markedly lower than that of the saline-administered group. Also, although no marked increase of an acute-phase toxicity marker of the liver or the kidney was observed, the BUN level was slightly increased in a dose-dependent manner.

Example 14

In Vivo Oligonucleotide Administration Experiment 5

Figure 19:
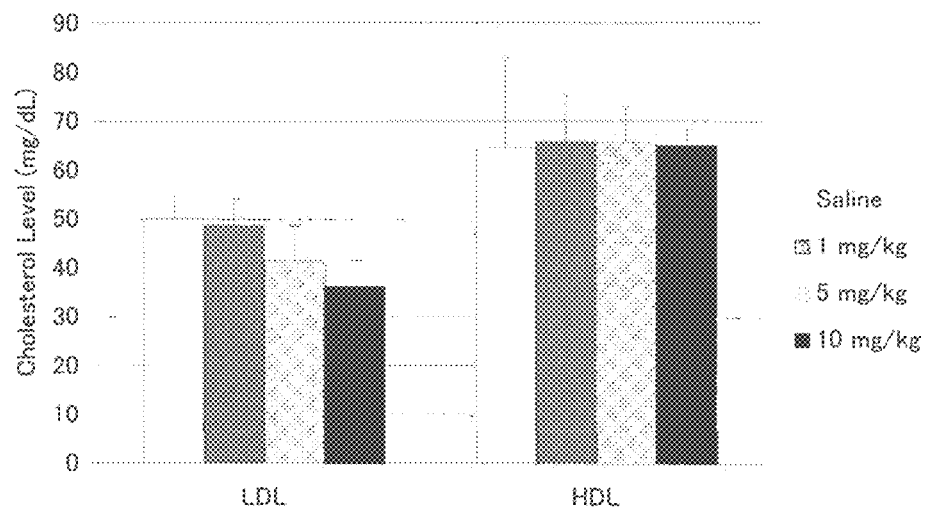
FIG. 19 is a graph showing serum cholesterol levels (according to the fraction) after 4-week mouse intraperitoneal administration of PCSK9-1-NC.

Five 6-week old C57BL6/J mice (male: CLEA Japan) were provided as test animals for each administration group. After 2 weeks of a high-fat load diet (F2HFD1, Oriental Yeast Co., Ltd.), the blood was collected on day 0, and PCSK9-1-NC was intraperitoneally administered. The dosage was 0, 1, 5, or 10 mg/kg. Administration was carried out twice per week for 6 weeks, and 4 weeks later or 6 weeks later, the blood was collected from the caudal vein in a fasting state. The serum total cholesterol level and the lipoprotein fraction cholesterol level were quantified in the same manner as in Example 10. FIG. 19 shows the results of determining the cholesterol levels in the LDL fractions and the cholesterol levels in the HDL fractions ("LDL" indicates the cholesterol levels in the LDL fractions, and "HDL" indicates the cholesterol levels in the HDL fractions).

As is clear from FIG. 19, although the HDL-C of the oligonucleotide PCSK9-1-NC-administered groups was not different from that of the saline-administered group, the LDL-C was reduced in a dose-dependent manner.

Example 15

In Vivo Oligonucleotide Administration Experiment 6

Figure 20:
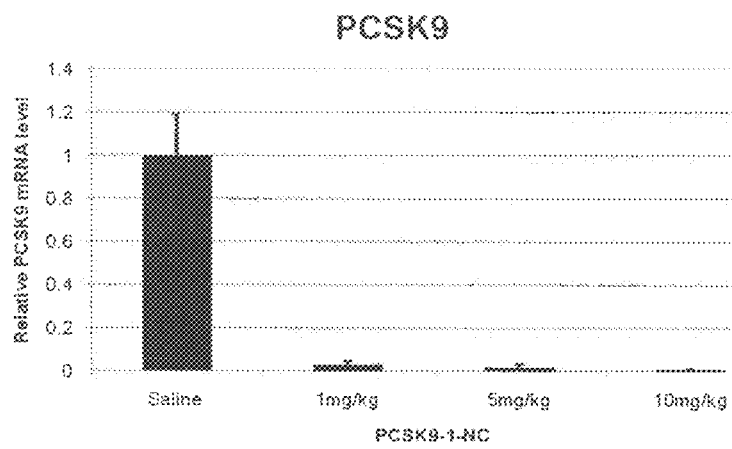
FIG. 20 is a graph showing the hepatic PCSK9 mRNA expression levels after 4-week mouse intraperitoneal administration of PCSK9-1-NC.

Five 6-week old C57BL6/J mice (male: CLEA Japan) were provided as test animals for each administration group. After 2 weeks of a high-fat load diet (F2HFD1, Oriental Yeast Co., Ltd.), the blood was collected on day 0, and PCSK9-1-NC was intraperitoneally administered. The dosage was 0, 1, 5, 10, or 20 mg/kg. Administration was carried out twice per week for 6 weeks, and 4 weeks later or 6 weeks later, the blood was collected from the caudal vein in a fasting state. Next, the mice were anesthetized with diethyl ether and then subjected to perfusion with PBS from the heart, and the liver was collected, washed with PBS, cut into small pieces, flash-frozen with liquid nitrogen, and then stored at −80° C. The PCSK9 mRNA level was quantified in the same manner as in Example 10. FIG. 20 shows the results.

As is clear from FIG. 20, the PCSK9 mRNA expression in the liver of the oligonucleotide PCSK9-1-NC-administered groups was highly efficiently suppressed (>97%) in a dose-dependent manner compared with the saline-administered group.

Example 16

In Vivo Oligonucleotide Administration Experiment 7

Using the mouse serum after administration of PCSK9-1-NC of Example 15, the AST level, the ALT level, and the BUN level were quantified in the same manner as in Example 10. FIG. 21 shows the results.

As is clear from FIG. 21, no marked increase of an acute-phase toxicity marker of the liver or the kidney was observed in the oligonucleotide PCSK9-1-NC-administered groups compared with the saline-administered group.

Example 17

In Vivo Oligonucleotide Administration Experiment 8

Figure 22:
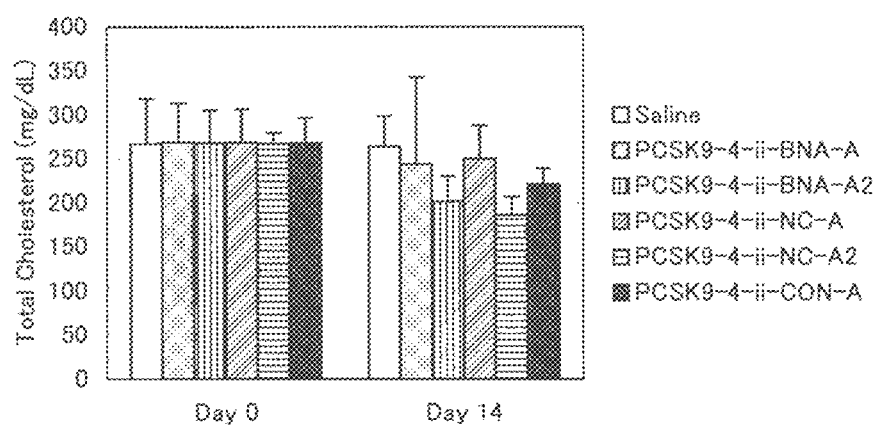
FIG. 22 is a graph showing serum total cholesterol levels before and after mouse caudal vein administration of BNA-oligonucleotide, NC-oligonucleotide, or CON-oligonucleotide.

Three 6-week old C57BL6/J mice (male: CLEA Japan) were provided as test animals for each administration group. After 3 weeks of a high-fat load diet (F2HFD1, Oriental Yeast Co., Ltd.), the blood was collected on day 0, and an oligo-nucleotide (PCSK9-4-ii-BNA-A, PCSK9-4-ii-BNA-A2, PCSK9-4-ii-NC-A, PCSK9-4-ii-NC-A2, or PCSK9-4-ii-CON-A) was intraperitoneally administered from the tail vein 9 days later and 12 days later (35 mg/kg). 14 days later, the blood was collected from the caudal vein in a fasting state. The serum total cholesterol level was quantified in the same manner as in Example 10. FIG. 22 shows the results.

As is clear from FIG. 22, although the serum total cholesterol level did not change in the saline-administered group, the serum total cholesterol levels of all BNA-oligonucleotide, NC-oligonucleotide, and CON-oligonucleotide-administered groups were lowered.

Example 18

In Vivo Oligonucleotide Administration Experiment 9

Figure 23:
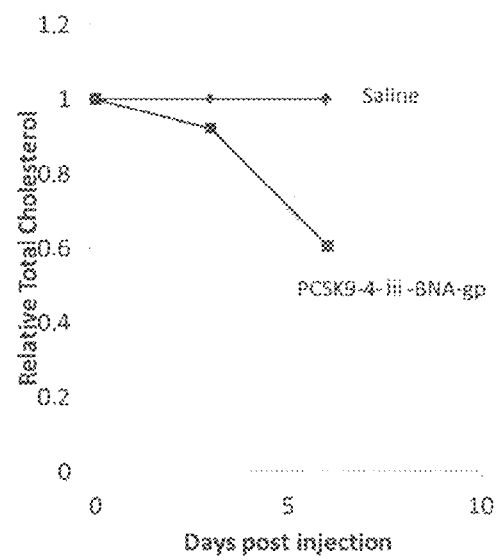
FIG. 23 is a graph showing the change over time of the serum total cholesterol level after 3-day guinea pig intraperitoneal administration of PCSK9-4-iii-BNA-gp.

One 3-week old guinea pig Hartley (male: Japan SLC Inc.) was provided as a test animal for each administration group. After 2 weeks of a high-fat load diet (F2HFD1, manufactured by Oriental Yeast Co., Ltd.), the blood was collected on day 0, and PCSK9-4-iii-BNA-gp (5'-CATgggcagccgCC-3'; all PS skeleton, lower-case character: DNA, upper-case character: BNA, a region in the guinea pig corresponding to the human target region composed of the base sequence of SEQ ID NO. 11 was regarded as a target) was intraperitoneally administered in a continuous manner for 3 days. The dosage was 0, 20, or 25 mg/kg per day. After administration, the blood was collected from one guinea pig from each administration group 3 days later and 7 days later. The serum total cholesterol level was quantified in the same manner as in Example 10. FIG. 23 shows the results.

As is clear from FIG. 23, as a result of administering the oligonucleotide PCSK9-1-iii-BNA-gp, the serum total cholesterol level was lowered by 8% 3 days later and lowered by 40% 7 days later.

Example 19

In Vivo Oligonucleotide Administration Experiment 10

Figure 24:
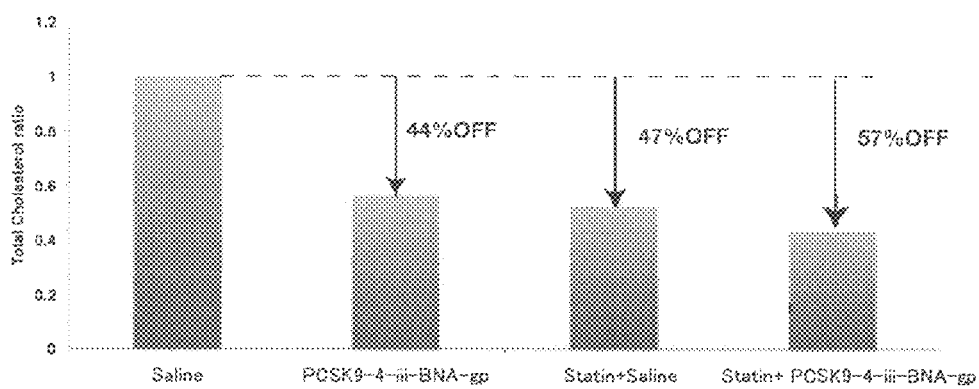
FIG. 24 is a graph showing decreases of serum total cholesterol levels after guinea pig intraperitoneal administration of PCSK9-4-iii-BNA-gp and/or lovastatin.

One 3-week old guinea pig Hartley (male: Japan SLC Inc.) was provided as a test animal for each administration group. After 2 weeks of a high-fat load diet (F2HFD1, manufactured by Oriental Yeast Co., Ltd.), the blood was collected on day 0, and saline, PCSK9-4-iii-BNA-gp, lovastatin+saline, or lovastatin+PCSK9-4-iii-BNA-gp was intraperitoneally administered. The dosage was configured such that lovastatin was continuously administered in an amount of about 30 mg/kg/day for 9 days, and PCSK9-4-iii-BNA-gp was administered in an amount of 20 mg/kg 3 times in 9 days. After administration, the blood was collected from one guinea pig from each administration group 7 days later. The serum total cholesterol level was quantified in the same manner as in Example 10. FIG. 24 shows the results.

As is clear from FIG. 24, the serum total cholesterol levels of the PCSK9-4-iii-BNA-gp-administered group, the lovastatin-administered group, and lovastatin+PCSK9-4-iii-BNA-gp-administered group were lowered by 44%, 47%, and 57%, respectively, relative to the saline administered group. PCSK9-4-iii-BNA-gp showed a cholesterol reducing effect despite its lower dosage than lovastatin, and showed an even greater effect when used in combination. When the blood was collected 3 days after the termination of lovastatin administration, the serum total cholesterol level of the lovastatin-administered group was recovered to the same level as the saline-administered group, but the serum total cholesterol level of the lovastatin+PCSK9-4-iii-BNA-gp-administered group was lowered by about 50% relative to the saline-administered group, continuously showing a cholesterol reducing effect.

Example 20

In Vivo Oligonucleotide Administration Experiment 11

Figure 25:
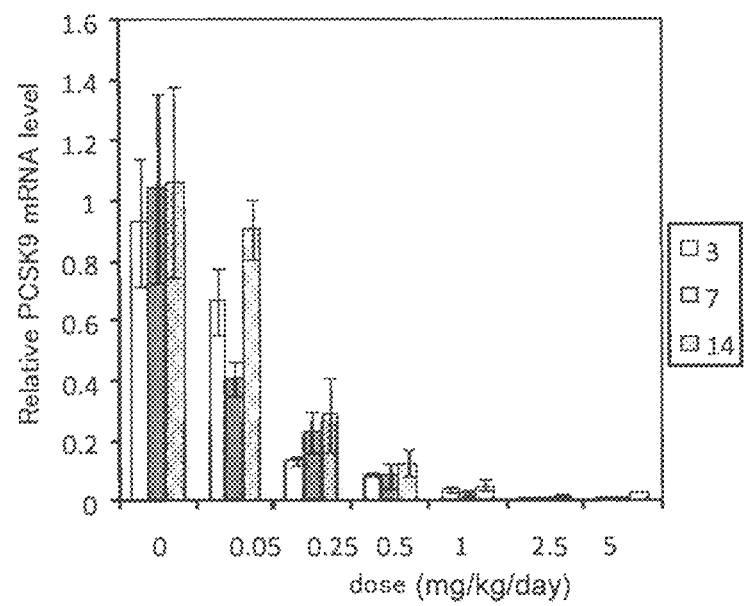
FIG. 25 is a graph showing the PCSK9 mRNA expression levels in the liver after single mouse intraperitoneal administration of PCSK9-1-BNA.

Nine 5-week old C57BL6/J mice (male: Japan SLC Inc.) were provided as test animals for each administration group. PCSK9-1-BNA dissolved in PBS was intraperitoneally administered. The dosage was 0, 0.05, 0.25, 0.5, 1, 2.5, or 5 mg/kg. After administration, 3 mice from each administration group were anesthetized with a mixed solution of anesthetic agents Vetorphale (manufactured by Meiji Seika Co., Ltd.), Domitor (Nippon Zenyaku Kogyo Co., Ltd.), and Dormicum (manufactured by Astellas Pharma, Inc.) 3 days later, 7 days later, and 14 days later, and then the blood was collected. Hepatic perfusion was carried out with PBS and the liver was collected and washed with PBS, and then the liver was entirely dissolved in 4 mL of a tissue lysis solution included in a QuickGene Kit (manufactured by FUJIFILM Corporation), and stored at −80° C. The mRNA was extracted from the thawed liver lysate using the QuickGene Kit. The subsequent cDNA preparation and real-time PCR were carried out in the same manner as in Example 10, and the PCSK9 mRNA level was quantified. FIG. 25 shows the results.

As is clear from FIG. 25, the PCSK9 mRNA expression level in the liver was lowered in a manner dependent on the dosage of PCSK9-1-BNA. Also, it recovered as the days passed.

Example 21

In Vivo Oligonucleotide Administration Experiment 12

Figure 26:
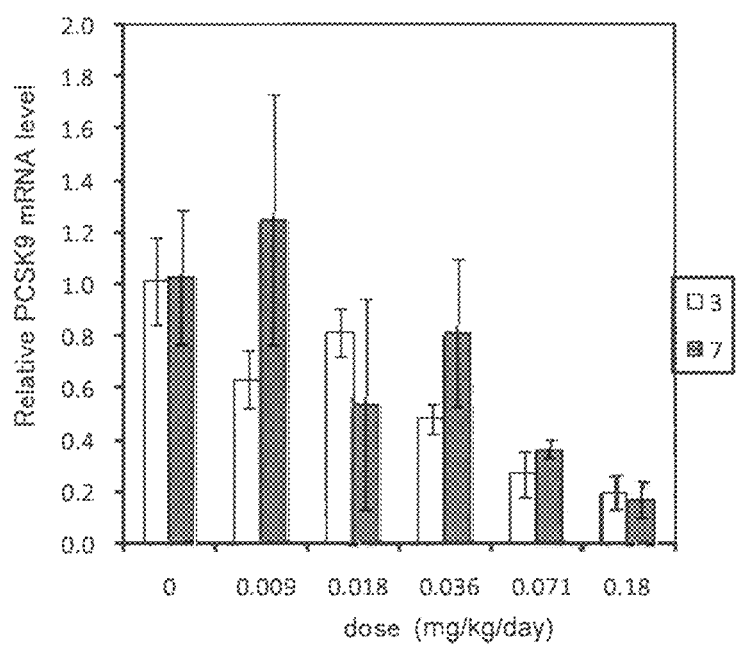
FIG. 26 is a graph showing the PCSK9 mRNA expression levels in the liver after continuous mouse intraperitoneal administration of PCSK9-1-BNA.

Nine 5-week old C57BL6/J mice (male: Japan SLC Inc.) were provided as test animals for each administration group. PCSK9-1-BNA dissolved in PBS was intraperitoneally administered in a continuous manner daily. The dosage was 0, 0.009, 0.018, 0.036, 0.071, or 0.18 mg/kg. This is the value with which the total dosage after 2 weeks of continuous administration reaches 0, 0.125, 0.25, 0.5, 1, or 2.5 mg/kg. After administration, 3 mice from each administration group were anesthetized with a mixed solution of anesthetic agents Vetorphale, Domitor, and Dormicum 3 days later and 7 days later, and then the blood was collected. Hepatic perfusion was carried out with PBS and the liver was collected and washed with PBS, and then the liver was entirely dissolved in 4 mL of a tissue lysis solution and stored at −80° C. The mRNA was extracted from the thawed liver lysate using a QuickGene Kit. The subsequent cDNA preparation and real-time PCR were carried out in the same manner as in Example 10, and the PCSK9 mRNA level was quantified. FIG. 26 shows the results.

As is clear from FIG. 26, the PCSK9 mRNA expression in the liver in the case of continuous administration as well was inhibited in a manner dependent on the dosage of PCSK9-1-BNA as in the case of single administration in Example 20. With the smallest dosage (a dosage of 0.027 mg/kg in 3 days), no clear inhibition was observed from single administration in Example 20, but inhibition was observed from continuous administration. This suggests that PCSK9-1-BNA formulated into a sustained-release preparation enhances the mRNA inhibitory effect.

Example 22

In Vivo Oligonucleotide Administration Experiment 13

Figure 27:
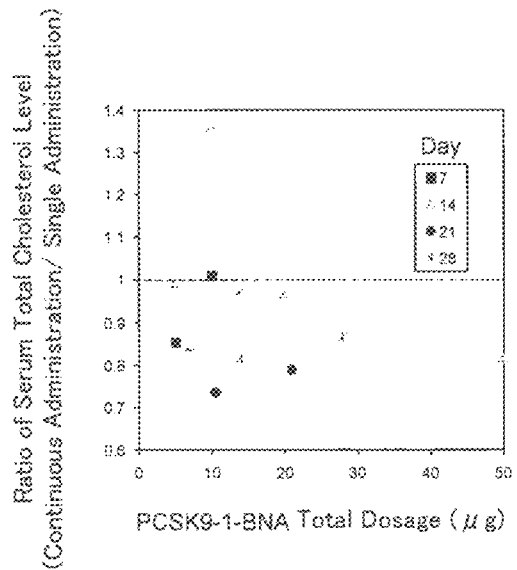
FIG. 27 is a graph showing the dosage of PCSK9-1-BNA and the ratio of the serum total cholesterol levels (continuous administration/single administration) in accordance with the number of days elapsed after administration until blood collection.

An experiment of single administration of PCSK9-1-BNA into a mouse was carried out in the same manner as in Example 20 except that the dosage of PCSK9-1-BNA and the number of days elapsed from administration until blood collection were changed so as to meet the conditions shown in Table 7. Also, an experiment of continuous administration of PCSK9-1-BNA into a mouse was carried out in the same manner as in Example 21 except that the dosage of PCSK9-1-BNA and the number of days elapsed from administration until blood collection were changed so as to meet the conditions shown in Table 7. The serum total cholesterol level was quantified in the same manner as in Example 10. FIG. 27 shows the ratios of the serum total cholesterol levels obtained in the continuous-administration experiment relative to the serum total cholesterol levels obtained in the single-administration experiment at predetermined days elapsed after administration of PCSK9-1-BNA.

TABLE 7

| | | Total dosage (µg) | | | | | | |
|---|---|---|---|---|---|---|---|---|
| | | 5 | 7 | 10 | 14 | 20 | 21 | 28 | 50 |
| Days after administration (days) | 7 | ○ | | ○ | | | | | |
| | 14 | ○ | ○ | ○ | ○ | ○ | | | ○ |
| | 21 | | | | | | ○ | | |
| | 28 | | | | ○ | | | ○ | |

As is clear from FIG. 27, many results obtained 7 days and 14 days after administration show that the ratios (continuous administration/single administration) of the serum total cholesterol levels are about 1.0 or exceed 1.0. This means that, from the comparison of the cholesterol reducing effects obtained from the same dosage, a sufficient effect is not obtained from about 2 weeks of sustained release. On the other hand, the results obtained 21 days and 28 days after administration show that the ratios (continuous/single) of the serum total cholesterol levels are greatly lower than 1.0. A comparison of FIGS. 25 and 26 shows that single administration and continuous administration of PCSK9-1-BNA in the same dosage do not result in a largely different PCSK9 mRNA inhibitory effect in the liver, but in regard to the cholesterol reducing effect, the effect of sustained release for prolonged exposure to low-concentration PCSK9-1-BNA can be greatly expected.

Example 23

Experiment of Treating Hyperlipidemic Rat by Embedding PCSK9-1-BNA-Containing Atelocollagen Gel 0.1 mg of PCSK9-1-BNA was kneaded into 0.1 mL of 3% by weight atelocollagen (Koken atelocollagen implant manufactured by Koken Co., Ltd.), the mixture was left to stand still at 37° C. for 24 hours, and thus a PCSK9-1-BNA-containing atelocollagen gel was prepared.

Two to five weeks old C57BL6/J mice (male: Japan SLC Inc.) were provided as test animals for each administration group. After 2 weeks of a high-fat load diet (F2HFD1, Oriental Yeast Co., Ltd.), the PCSK9-1-BNA-containing atelocollagen gel was intraperitoneally (I.P.) or subcutaneously (S.C.) embedded under anesthesia (BNA-in-Gel group). For comparison, an untreated group (control group), a group whose members were embedded with a PBS-containing gel (PBS-in-Gel group), and a group whose members were embedded with a gel and separately administered with PCSK9BNA (Gel+BNA group) were provided.

Figure 28:
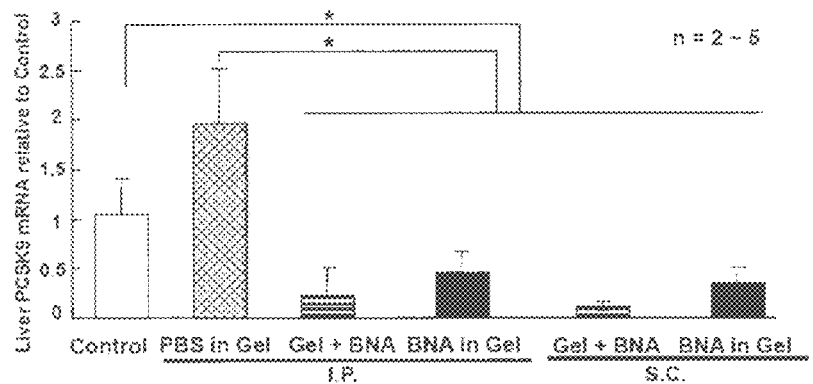
FIG. 28 is a graph showing the PCSK9 mRNA expression levels in the liver 3 days after mouse intraperitoneal administration of PCSK9-1-BNA-containing gel.
Figure 29:
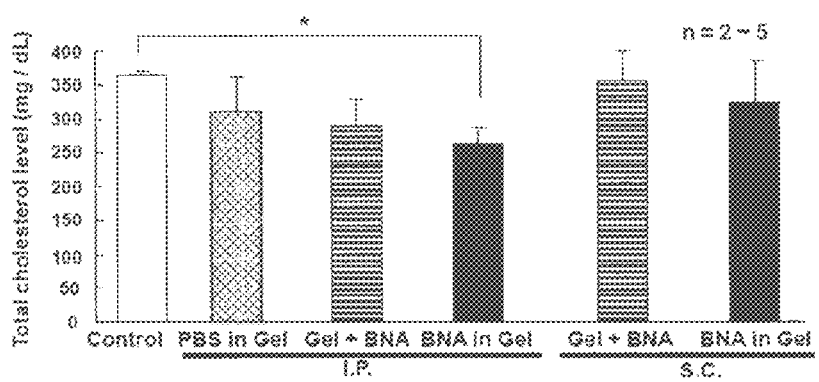
FIG. 29 is a graph showing the serum total cholesterol levels 3 days after mouse intraperitoneal administration of PCSK9-1-BNA-containing gel.
Figure 30:
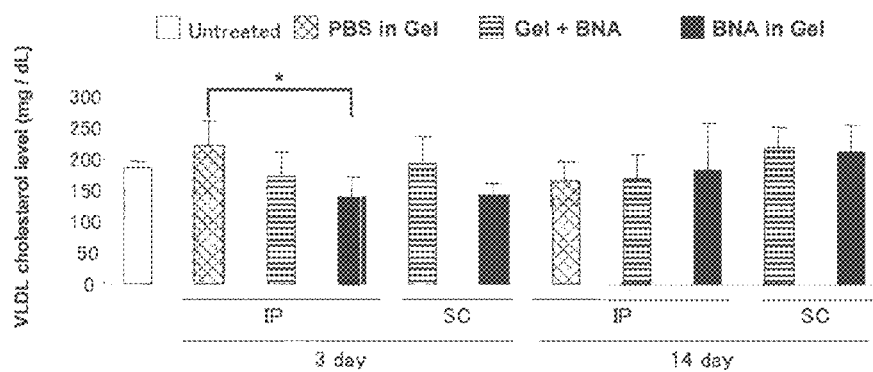
FIG. 30 is a graph showing the cholesterol levels in the VLDL fraction 3 days after and 14 days after mouse intraperitoneal administration of PCSK9-1-BNA-containing gel.

After embedding or administration, a high-fat load diet was further given for 3 days and for 14 days, and then the blood was collected from the tail. Next, the mice were anesthetized with a mixed solution of anesthetic agents Vetorphale, Domitor, and Dormicum, and then the gel was collected. Hepatic perfusion was carried out with PBS and the liver was collected, washed with PBS, then homogenized, and stored at −80° C. The mRNA was extracted from the thawed liver using a QuickGene Kit. The subsequent cDNA preparation and real-time PCR were carried out in the same manner as in Example 10, and the mRNA level of PCSK9 was quantified. Also, the serum total cholesterol level and VLDL-C was quantified in the same manner as in Example 10. FIG. 28 shows the results of determining the mRNA levels 3 days later, FIG. 29 shows the results of determining the serum total cholesterol levels 3 days later. Also, FIG. 30 shows the results of determining VLDL-C 3 days later and 14 days later.

As is clear from FIG. 28, regardless of whether PCSK9-1-BNA was intraperitoneally administered or subcutaneously administered, the level of PCSK9 mRNA expression was markedly lowered. On the other hand, as is clear from FIG. 29, a markedly lowered serum total cholesterol level was observed only in the group for which a PCSK9-1-BNA-containing atelocollagen gel was used (BNA-in-Gel group). It was thus shown that an administration method that involves sustained release of PCSK9-1-BNA from an atelocollagen gel may demonstrate a more efficient treatment effect than an administration method that directly administers PCSK9-1-BNA. As is clear from FIG. 30, VLDL-C was markedly lowered 3 days later, but it was recovered to the same level as that of the untreated group 14 days later.

Example 24

Experiment of Sustained-Release Treatment of PCSK9-1-BNA from Peptidic Injectable Hydrogel Peptidic injectable hydrogels composed of peptide sequences mimicking 2-microglobulin shown in Table 8 were used as carriers for sustained release of PCSK9-1-BNA (the amino acid sequences of peptides 1 to 4 in Table 8 correspond to SEQ ID NOS. 36 to 39, respectively). The peptides were synthesized by the Fmoc solid-phase method, and dissolved in DMSO/H$_2$O in a concentration of 1% by weight to complex with oligonucleotides. Peptides 3 and 4 formed uniform gels when 10% DMSO/H$_2$O was used as a solvent. In particular, the hydrogel of peptide 4 showed prompt gelating properties of forming a gel within 5 minutes, and as shown in Table 9, demonstrated a high elastic modulus in a concentration-dependent manner.

TABLE 8

| | Peptide sequence | Gelation behavior in 10%-DMSO |
|---|---|---|
| Peptide 1 | Ac-(RVDI)$_4$-CONH$_2$ | No gelation |
| Peptide 2 | Ac-(RVEI)$_4$-CONH$_2$ | No gelation |
| Peptide 3 | Ac-(RVKVEIDI)$_2$-CONH$_2$ | Gelation |
| Peptide 4 | Ac-(RVEIKVDI)$_2$-CONH$_2$ | Gelation |

TABLE 9

| Peptide concentration (mass %) | Modulus (loss modulus G″) (Pa) |
|---|---|
| 0.5 | 148 |
| 1 | 407 |
| 2 | 1250 |

3 μg of PCSK9-1-BNA was mixed with 0.1 mL of an aqueous peptide 4 solution (peptide concentration of 1% by weight; DMSO concentration of 10 (v/v)%) and left to stand at room temperature, and thus a PCSK9-1-BNA-containing injectable hydrogel was prepared.

Figure 31:
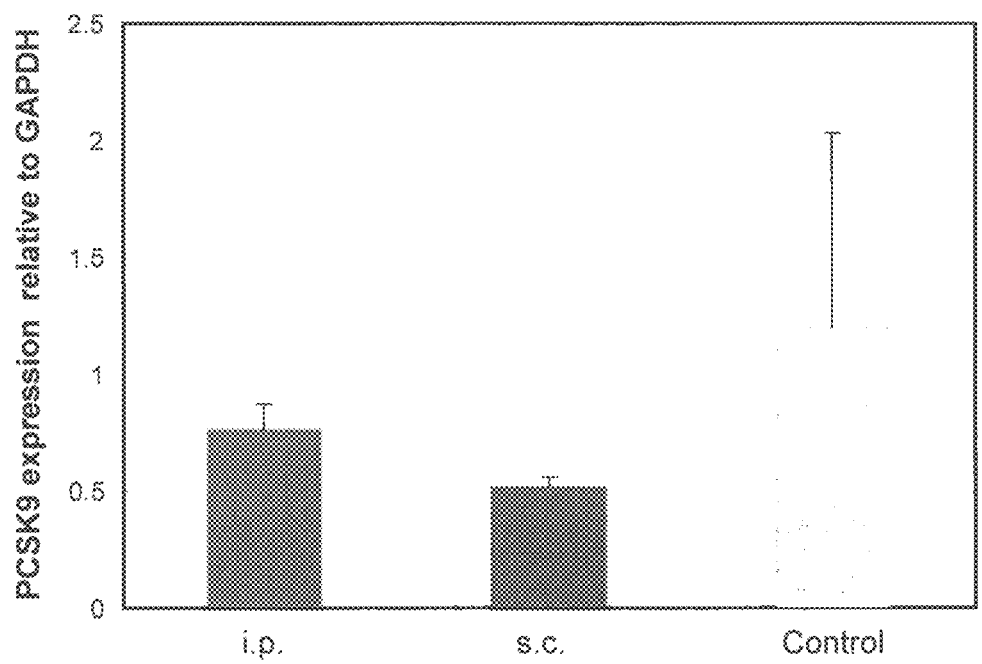
FIG. 31 is a graph showing the PCSK9 mRNA expression levels in the liver 3 days after mouse intraperitoneal or subcutaneous administration of peptidic injectable hydrogel.

5-week old C57BL6/J mice (male: Japan SLC Inc.) were used as test animals. The PCSK9-1-BNA-containing peptidic injectable hydrogel was embedded intraperitoneally (i.p.) or subcutaneously (s.c.). After embedding, the mice were anesthetized with a mixed solution of anesthetic agents Vetorphale, Domitor, and Dormicum 3 days after. Hepatic perfusion was carried out with PBS, and the liver was collected, washed with PBS, then entirely dissolved in 4 ml of a tissue lysis solution, and stored at −80° C. The mRNA was extracted from the thawed liver lysate using a QuickGene Kit. The subsequent cDNA preparation and real-time PCR were carried out in the same manner as in Example 10, and the mRNA level of PCSK9 was quantified. FIG. 31 shows the results.

As is clear from FIG. 31, in both cases, the PCSK9 mRNA expression in the liver was significantly inhibited.

It seems that a peptidic injectable hydrogel that gelates in several minutes and completely disappears in 2 weeks in the living body is useful as a carrier of a sustained-release preparation for dyslipidemia that contains an oligonucleotide as an active ingredient.

Example 25

Sustained-Release Behavior of PCSK9-1-BNA from Peptidic Injectable Hydrogel 20 mg of PCSK9-1-BNA labeled with a fluorescent dye Alexa 750 (manufactured by Molecular Probes) (Alexa 750-PCSK9-1-BNA) was mixed with 100 mL of an aqueous peptide 4 solution (peptide concentration of 1% by weight; DMSO concentration of 10 (v/v) %) and left to stand at room temperature, and thus a PCSK9-1-BNA-containing peptidic injectable hydrogel was prepared.

Figure 32:
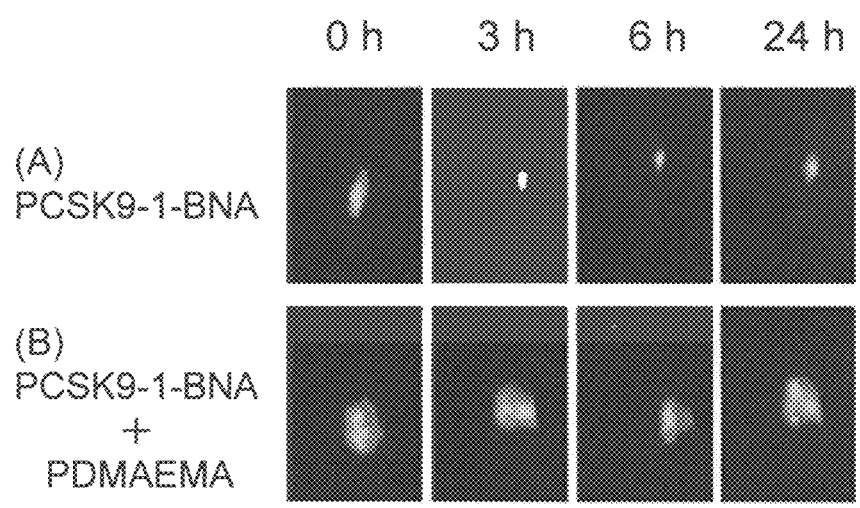
FIG. 32 includes images showing the results of analyzing by an in vivo imager over time Alexa 750-PCSK9-1-BNA remaining after mouse subcutaneous administration of peptidic injectable hydrogel.

5-week old C57BL6/J mice (male: Japan SLC Inc.) were used as test animals. The Alexa 750-PCSK9-1-BNA-containing peptidic injectable hydrogel was embedded subcutaneously (s.c.). After embedding, using an in vivo imager (Maestro), Alexa 750-PCSK9-1-BNA remaining in the gel was quantified over time. FIG. 32(A) shows the results.

As is clear from FIG. 32(A), a large amount of Alexa 750-PCSK9-1-BNA locally disappeared immediately after being embedded, and a sufficient sustained-release effect was not obtained.

Therefore, in order to retain Alexa 750-PCSK9-1-BNA in the gel for a long period of time, a complex between Alexa 750-PCSK9-1-BNA and a polycation (poly[2-(diethylamino) ethyl methacrylate]: PDMAEMA; Mn=86000, Mw/Mn=1.9) ([number of nitrogen atoms of PDMAEMA]:[number of phosphorus atoms of Alexa 750-PCSK9-1-BNA]=48:1, prepared by being mixed at room temperature for 30 minutes) was used in place of Alexa 750-PCSK9-1-BNA, and a PCSK9-1-BNA-containing peptidic injectable hydrogel was prepared in the same manner. Then, after the gel was embedded in a mouse in the same manner, the Alexa 750-PCSK9-1-BNA remaining in the gel was evaluated over time using an in vivo imager. FIG. 32(B) shows the results.

As is clear from FIG. 32(B), it was possible to greatly inhibit the local disappearance of Alexa 750-PCSK9-1-BNA.

INDUSTRIAL APPLICABILITY

According to the present research, an oligonucleotide useful as a therapeutic agent for dyslipidemia that has excellent binding affinity to the PCSK9 gene as well as stability and safety can be provided. The oligonucleotide of the present invention is expected to be used as a therapeutic drug effective against familial hypercholesterolemia as well as hyperlipidemia, which causes cardiac infarction and apoplexy.

The invention claimed is:

1. An oligonucleotide comprising a sugar-modified nucleoside, the sugar-modified nucleoside having a bridging structure between 4'-position and 2'-position, and the oligonucleotide being capable of binding to human PCSK9 gene, wherein the bridging structure is represented by —CO—NR$^1$—, —CH$_2$—CO—NR$^1$—, —(CH$_2$)$_2$—CO—NR$^1$—, —CO—NR$^1$—X—, or —CH$_2$—CO—NR$^1$—X—, wherein R$^1$ is a hydrogen atom;

a C$_{1-7}$ alkyl group that may form a branch or ring;

a C$_{2-7}$ alkenyl group that may form a branch or ring;

a C$_{3-12}$ aryl group that may have any one or more substituents selected from an α group consisting of a hydroxyl group, C$_{1-6}$ linear alkyl group, C$_{1-6}$ linear alkoxy group, mercapto group, C$_{1-6}$ linear alkylthio group, amino group, C$_{1-6}$ linear alkylamino group, and halogen atom, and that may contain a hetero atom; or an aralkyl group having a C$_{3-12}$ aryl portion that may have any one or more substituents selected from the α group and that may contain a hetero atom; and X is an oxygen atom, sulfur atom, amino group, or methylene group.

2. The oligonucleotide according to claim 1, wherein the human PCSK9 gene is a DNA or RNA composed of a base sequence containing any of the following base sequences: base sequence of SEQ ID NO. 3; base sequence of SEQ ID NO. 4; base sequence of SEQ ID NO. 5; base sequence of SEQ ID NO. 6; base sequence of SEQ ID NO. 7; base sequence of SEQ ID NO. 8; base sequence of SEQ ID NO. 9; base sequence of SEQ ID NO. 10; base sequence of SEQ ID NO. 11; base sequence of SEQ ID NO. 12; base sequence of SEQ ID NO. 13; base sequence of SEQ ID NO. 14; base sequence of SEQ ID NO. 15; base sequence of SEQ ID NO. 16; base sequence of SEQ ID NO. 17; base sequence of SEQ ID NO. 18; or base sequences complementary to these.

3. The oligonucleotide according to claim 1, wherein the oligonucleotide has a base sequence length of 10 to 25 bases.

4. The oligonucleotide according to claim 1, wherein at least one selected from the group consisting of an intercalator, reporter molecule, polyamine, polyamide, polyethylene glycol, thioether, polyether, cholesterol, thiocholesterol, cholic acid portion, folic acid, lipid, phospholipid, biotin, phenazine, phenanthridine, anthraquinone, adamantane, acridine, fluorescein, rhodamine, coumarin, and pigment is bound to a 5'-end or 3'-end of the oligonucleotide.

5. A therapeutic agent for dyslipidemia, comprising an oligonucleotide of claim 1 as an active ingredient.

6. The therapeutic agent according to claim 5, which is a sustained-release preparation comprising a bioabsorbable material as a carrier.

7. The therapeutic agent according to claim 6, wherein the bioabsorbable material is atelocollagen or peptide gel.

8. A therapeutic agent for dyslipidemia, comprising an oligonucleotide of claim 2 as an active ingredient.

9. The therapeutic agent according to claim 8, which is a sustained-release preparation comprising a bioabsorbable material as a carrier.

10. The therapeutic agent according to claim 9, wherein the bioabsorbable material is atelocollagen or peptide gel.

* * * * *